US006063763A

United States Patent [19]

Light et al.

[11] Patent Number: 6,063,763

[45] Date of Patent: May 16, 2000

[54] PROTEASE-RESISTANT THROMBOMODULIN ANALOGS

[75] Inventors: David Richard Light; William H. Andrews, both of San Mateo; Jeffrey Homer Clarke, Pacifica; Robert Michael Wydro, Foster City; Patricia Ann Young, San Rafael, all of Calif.

[73] Assignee: Schering Aktiengesellschaft, Berlin, Germany

[21] Appl. No.: 08/197,576

[22] Filed: Feb. 16, 1994

Related U.S. Application Data

[63] Continuation of application No. 07/830,577, Feb. 5, 1992, abandoned, which is a continuation-in-part of application No. 07/568,456, Aug. 15, 1990, abandoned, which is a continuation-in-part of application No. 07/506,325, Apr. 9, 1990, Pat. No. 5,256,770, which is a continuation-in-part of application No. 07/406,941, Sep. 13, 1989, abandoned, which is a continuation-in-part of application No. 07/345,372, Apr. 28, 1989, abandoned.

[51] Int. Cl.[7] .......................... A61K 38/00; A61K 35/14; C12P 21/06; C12P 21/04

[52] U.S. Cl. .......................... 514/12; 435/69.1; 435/69.6; 530/380; 530/402

[58] Field of Search .............................. 514/12; 530/402, 530/412, 417, 380; 435/69.1, 69.6

[56] References Cited

U.S. PATENT DOCUMENTS

| | | | |
|---|---|---|---|
| 4,740,461 | 4/1988 | Kaufman | 435/68 |
| 4,748,156 | 5/1988 | Aoki et al. | 514/21 |
| 4,752,585 | 6/1988 | Koths et al. | 435/256 |
| 4,835,260 | 5/1989 | Shoemaker | 530/397 |
| 5,043,425 | 8/1991 | Aoki et al. | 530/350 |
| 5,047,503 | 9/1991 | Aoki et al. | 530/350 |
| 5,256,770 | 10/1993 | Glaser et al. | 530/381 |

FOREIGN PATENT DOCUMENTS

| | | |
|---|---|---|
| 0 290 419 | 11/1988 | European Pat. Off. . |
| 0 312 598 | 4/1989 | European Pat. Off. . |
| 0 474 273 | 3/1992 | European Pat. Off. . |
| 88/09811 | 12/1988 | WIPO . |
| 90/00955 | 2/1990 | WIPO . |
| 90/10081 | 9/1990 | WIPO . |
| 91/15514 | 10/1991 | WIPO . |
| 92/03149 | 3/1992 | WIPO . |

OTHER PUBLICATIONS

Glaser et al., J. Clin. Invest., 90:2565–2573 (1992).

Bowie et al., Science, 247:1306–1310 (1990).

Hayashi et al., J. Biol. Chem., 265(33):20156–20159 (1990).

Zushi et al., J. Biol. Chem., 266(30):19886–19889 (1991).

Tsiang et al., J. Biol. Chem., 267(9):6164–6170 (1992).

Proteolytic Formation and Properties of Functional Domains of Thrombomodulin, Shinichiro Kurosawa et al., vol. 262, No. 5, The Journal of Biological Chemistry, pp. 2206–2212, 1987.

Soluble Thrombomodulin antigen in Conditioned Medium is Increased by Damage of Endothelial Cells, Hidemi Ishii et al., Thrombosis and Haemostasis, vol. 65, pp. 618–623, 1991.

The Glycosaminoglycan of Recombinant Human Soluble Thrombomodulin Affects Antithrombotic Activity in a Rat Model of Tissue Factor–Induced Disseminated Intravascular Coagulation, Katsuhiko Nawa et al., Thrombosis and Haemostasis, vol. 67, pp. 366–370, 1992.

Umezawa, Methods of Enzymology, 55:678–695 (1976).

Emson et al., J. of Biol. Chem., 257:859–864 (1982).

Jackman et al., PNAS, 83:8834–8838 (1986).

Jackman et al., PNAS, 84:6425–6429 (1987).

Wen et al., Biochem., 26:4350–4357 (1987).

Kurosawa et al., J. of Biol. Chem., 263:5993–5996 (1988).

Zushi et al., J. of Biol. Chem., 264:10351–10353 (1989).

Bourin et al., PNAS, 83:5924–5928 (1986).

Ishii et al., J. Clin. Inv., 76:2178–2181 (1985).

Stearns et al., J. of Biol. Chem., 264:3352–3356 (1989).

Yost et al., Cell, 34:759–766 (1983).

Parkinson et al., J. of Biol. Chem., 265:12602–12610 (1990).

Salem et al., J. of Biol. Chem., 259:12246–12251 (1984).

Preissner et al., J. of Biol. Che., 265(9):4915–4922 (1990).

"Prevention of Venous Thrombosis and Pulmonary Embolism," Consensus Development Conference Statement, NIH, 6(2):1–23 (Mar. 1986).

Dayhoff et al., Atlas of Protein Sequence and Structures, 5:89–99 (1972).

Holmes et al., Biochemistry, 26:5133–5140 (1987).

Suzuki et al., The EMBO Journal, 6(7):1891–1897 (1987).

Suzuki et al., J. Biol. Chem., 264(9):4872–4876 (Mar. 25, 1989).

Galvin et al., J. Biol. Chem., 262:2199–2205 (1987).

Maruyama et al., J. Clon, Invest., 75:987–991 (1985).

Suzuki et al., J. Biochem., 104:628–632 (1988).

Kurosawa et al., J. Biol. Chem., 262:2206–2212 (1987).

Otani et al., Circulation Research, 55(2):168–175 (1984).

Saldeen et al., Surgical Clinics of N. America, 63(2):285–304 (1983).

Idell et al., J. Clin. Invest., 84:695–705 (1989).

Clark et al., The Mol & Cell. Biol. of Wound Repair, 4:87–114 (1988).

Brot et al., Archives of Biochem. and Biophys., 223(1):271–281 (May 1983).

(List continued on next page.)

*Primary Examiner*—Charles L. Patterson, Jr.
*Assistant Examiner*—Einar Stole
*Attorney, Agent, or Firm*—Millen, White, Zelano & Branigan, P.C.

[57] ABSTRACT

The present invention relates to the single-chain thrombomodulin ("TM") and analogs thereof that are not susceptible to cleavage by proteases and retain the biological activity of thrombomodulin, as well as methods of use in, for example, antithrombotic therapy. Novel proteins, nucleic acid gene sequences, pharmaceuticals and methods of inhibiting thrombotic activity are disclosed.

18 Claims, 4 Drawing Sheets

OTHER PUBLICATIONS

Nexoe et al., Chem. Abstracts, 111(25):226607a (Dec. 18, 1989).

Nagashima et al., J. of Biol. Chem., 268(4):2888–2893 (Feb. 5, 1993).

Clarke et al., J. of Biol. Chem., 268(9):6309–6315 (Mar. 25, 1993).

Parkinson et al., Biochem. and Biophys. Research Communications, 185(2):567–576 (Jun. 15, 1992).

Dittman et al., J. of Biol. Chem., 263(30):15815–15822 (1988).

Isolation of a Membrane–bound Cofactor for Thrombin–catalyzed Activation of Protein C, Naomi L. Esmon, The Journal of Biological Chemistry, vol. 251, No. 2, pp. 859–864, 1982.

Characterization of a thrombomodulin cDNA reveals structural similarity to the low density lipoprotein receptor, Robert W. Jackman et al., Proc. Natl. Acad. Sci., vol. 83, pp. 8834–8838, 1986.

Human thrombomodulin gene is intron depleted: Nucleic acid sequences of the cDNA and gene predict protein structure and suggest sites of regulatory control, Proc. Natl. Acad. Sci., vol. 84, pp. 6425–6429, 1987.

Human Thrombomodulin: Complete cDNA Sequence and Chromosome Localization of the Gene, Duanzhi Wen et al., Biochemistry, vol. 26, pp. 4350–4357, 1987.

A 10–kDa Cyanogen Bromide Fragment from the Epidermal Growth Factor Homology Domain of Rabbit Thromobomodulin Contains the Primary Thrombin Binding Site, Shinichiro Kurosawa et al., The Journal of Biological Chemistry, vol. 263, No. 13, pp. 5993–5996, 1988.

The Last Three Consecutive Epidermal Growth Factor–like Structures of Human Thrombomodulin Comprise the Minimum Functional Domain for Protein C–activating Cofactor Activity and Anti–coagulant Activity, Michitaka Zushi et al., The Journal of Biological Chemistry, vol. 264, No. 18, pp. 10351–10353, 1989.

Functional domains of rabbit thrombomodulin, Marie–Claude Bourin et al., Proc. Natl. Acad. Sci., vol. 83, pp. 5924–5928, 1986.

Thrombomodulin Is Present in Human Plasma and Urine, Hidemi Ishii et al., J. Clin. Invest., vol. 76, pp. 2178–2181, 1985.

Microthrombomodulin, Deborah J. Stearns et al., The Journal of Biological Chemistry, vol. 264, No. 6, pp. 3352–3356, 1989.

Stable Expression of a Secretable Deletion Mutant of Recombinant Human thrombomodulin in Mammalian Cells, John F. Parkinson et al., The Journal of Biological Chemistry, vol. 283, No. 21, pp. 12602–12610, 1990.

Isolation and Characterization of Thrombomodulin from Human Placenta, Hatem H. Salem et al., The Journal of Biological Chemistry, vol. 259, No. 19, pp. 12246–12251, 1984.

A Stop Transfer Sequence Confers Predictable transmembrane Orientation to a Previously Secreted Protein in Cell–Free Systems, C. Spencer Yost et al., Cell, vol. 34, pp. 759–766, 1983.

Umezawa. (1976) Methods in Enzymology 55:678–695.

PROTEASE-RESISTANT THROMBOMODULIN ANALOGS

This application is a continuation of application Ser. No. 07/830,577, filed Feb. 5, 1992, now abandoned, which is a continuation-in-part of Ser. No. 07/568,456 filed Aug. 15, 1990, now abandoned, which is a continuation-in-part of Ser. No. 07/506,325 filed Apr. 9, 1990, now U.S. Pat. No. 5,256,770, which is a continuation-in-part of Ser. No. 07/406,941 filed Sep. 13, 1989, now abandoned, which is a continuation-in-part of Ser. No. 07/345,372 filed Apr. 28, 1989, now abandoned.

BACKGROUND OF THE INVENTION

The present invention relates to single-chain thrombomodulin polypeptides, including analogs of thrombomodulin ("TM") that are less susceptible to cleavage by proteases. These analogs are useful in, for example, antithrombotic therapy. Novel proteins, nucleic acid gene sequences, pharmaceuticals, and methods of inhibiting thrombotic activity are disclosed.

There are many disease states that would benefit from treatment with a safe and effective anticoagulant/antithrombotic. The nature of these conditions varies. For example, anticoagulant therapy is useful in acute conditions such as during thrombolytic therapy in myocardial infarction or in treatment of disseminated intravascular coagulation (DIC) associated with, for example, septicemia. Anticoagulants are also useful for less acute conditions, such as chronic use in patients that have received heart valve implants or prophylactic use in surgery patients to reduce the risk of deep venous thrombosis (DVT).

Thrombomodulin is a membrane protein that has demonstrated anticoagulant properties. Its physiological importance has been studied. (See, for example, N. Esmon, et al., (1982) *J. Biol. Chem.* 257:859–864, H. Salem, et al., (1983) *J. Biol. Chem.* 259:12246–12251).

The gene encoding native thrombomodulin has been isolated and sequenced from several species, both in its genomic form and as a cDNA clone (Jackman, R., et al., (1986) *Proc. Natl. Acad. Sci. U.S.A.* 83:8834–8838 and (1987) 84:6425–6429, both of which are herein incorporated by reference). Comparisons with known proteins, such as the LDL receptor, have suggested functional domains (Wen, D., et al., (1987) *Biochemistry* 26:4350–4357). One study has suggested that the fifth and sixth epidermal growth factor (EGF)-like domains have the capacity to bind thrombin (Kurosawa, S., et al., (1988) *J. Biol. Chem.* 263:5993–5996); another suggests that EGF-like domains 4, 5, and 6 are sufficient to act as a cofactor for thrombin-mediated protein C activating activity. (Zushi, et al., (1989) *J. Biol. Chem.* 264:10351–10353). Inhibition of thrombin's direct procoagulant activity (conversion of fibrinogen to fibrin) has been attributed in part to glycosaminoglycan substituents on the thrombomodulin molecule. (Bourin, M. C. et al., (1986) *Pro. Natl. Acad. Sci. U.S.A.* 83:5924–5928.) The O-linked glycosylation domain has potential sites for the addition of these types of sulfated sugars.

Thrombomodulin analogs, including soluble molecules, having various modifications are known. There are, for example, modifications to oxidation-sensitive amino acid residues in thrombomodulin which render the molecule resistant to oxidation. There are also modifications to thrombomodulin, e.g., by elimination of sulfated o-linked carbohydrates through enzymatic removal or modification of glycosylation sites on the peptide, which decrease the inhibition of thrombin-mediated platelet aggregation and thrombin-mediated conversion of fibrinogen to fibrin, which is an important property of thrombin. These modifications are disclosed in U.S. Ser. No. 07/568,456, filed Aug. 15, 1990, which is incorporated herein by reference.

Anticoagulants currently approved for use in humans are not uniformly effective and a need exists for more efficacious compounds (See, for example, Prevention of Venous Thrombosis and Pulmonary Embolism, Consensus Development Conference Statement, NIH, 1986, 6(2):1–23).

Thrombomodulin in its native form is not suitable for anticoagulant therapy as it is membrane-bound, due to its inherent amino acid sequence, and is insoluble without detergent treatment. It is present in such small amounts (about 300 mg thrombomodulin/person) that purification from autopsy or biopsy samples is impractical.

Soluble thrombomodulin-like molecules have been detected at very low amounts in human plasma and urine. These molecules have a reduced ability to promote protein C activation, and it is possible that they have been rendered at least partially inactive, due at least in part, to oxidation. It has been suggested that these molecules are degradation products of the membrane bound molecule (Ishii, H. and Majerus, P., (1985) *J. Clin. Inv.* 76:2178–2181), but they are present in such low amounts that they have been difficult to characterize (~0.8 mg/adult male). Proteolytic fragments of the purified native molecule have been produced using trypsin or elastase. (See, Ishii, supra, Kurosawa, et al., (1988) *J. Biol. Chem.* 263:5593–5996 and Stearns, et al., (1989) *J. Biol. Chem.* 264:3352–3356). Some of these fragments retain the ability to promote thrombin-mediated activation of protein C in vitro.

The production of TM and TM analogs by recombinant techniques in heterologous cells, e.g., in cell culture, has encountered numerous problems in achieving acceptable products for use in in vivo applications. For example, the N-terminal end of TM is imprecisely cleaved in cells containing the recombinant gene as well as in native cells, resulting in a product that has a non-unique N-terminus. This causes, among other difficulties, a problem in providing proof of purity of the isolated polypeptide, e.g., for regulatory purposes. Glycosylation of recombinantly produced TM has also proved to be a problem, in that some of the glycosylation sites are apparently involved in maximizing biological activity, while other sites are apparently recognized as signals in vivo to clear the bloodstream of TM, thus reducing the circulating half-life of a TM so glycosylated. Other, less well defined problems also are known to exist which interfere with the production of a maximally useful recombinantly produced TM polypeptide.

Thus, there is a need for new compositions that exhibit the anticoagulant properties of thrombomodulin and are easily produced in large quantities, but without the problems encountered in recombinant production of TM by heterologous cells. The present invention fulfills these and other needs.

SUMMARY OF THE INVENTION

This invention provides single-chain thrombomodulin (TM) substantially devoid of two-chain TM. This TM is provided by removal of two-chain TM from preparations which contain it, or by preventing cleavage of single-chain TM.

In another embodiment, this invention provides TM having a single N-terminus. This TM is provided by the absence of two-chain TM, and/or by the elimination of the natural, heterogeneous N-terminal signal sequence processing site.

In another embodiment, this invention provides TM having a single C-terminus. This TM is provided by the absence of a C-terminus which is sensitive to exocarboxypeptidase.

In another embodiment, this invention provides single-chain TM which can be expressed in eukaryotic cells, e.g., animal cells, vertebrate cells, insect cells mammalian cells, human cells, etc., e.g., in CHO or CHL1 cells.

This invention provides methods for treating thrombotic disease by administering an effective dose of a single-chain thrombomodulin or analog thereof, typically one which is resistant to protease cleavage and which retains the biological activity of thrombomodulin. In some preferred aspects, the polypeptide composition exhibits only a single N-terminus and a single C-terminus, has at least approximately native ability to potentiate thrombin-mediated activation of protein C, and/or has a reduced ability to inactivate thrombin-mediated conversion of fibrinogen to fibrin. It is preferred in some embodiments that the analog is soluble in aqueous solution and/or has a long circulating half-life, e.g., is oxidation and/or protease resistant.

In other embodiments, it is preferred that the analog be modified in the sugar residues of the O-linked glycosylation domain. By modified it is meant that the O-linked glycosylation domain has an altered glycosylation pattern. This can encompass substitution, and total or partial deletion of native sugar residues. This modification can be achieved by deleting the amino acid residues that are recognized by cells as glycosylation sites e.g., by site directed mutagenses. Alternatively the sugars can be chemically removed, either partially or totally. In another modification the sugars can be enzymatically treated to remove sulfate substituents. In yet another modification the entire glycosylation domain can be deleted.

Some preferred analogs for use in the method will retain the capacity to potentiate the thrombin-mediated activation of protein C and/or have 80% or less of the capacity of native thrombomodulin to inactivate thrombin-mediated conversion of fibrinogen to fibrin. More specifically, these TM analogs, when standardized to have an equal activity in a standard protein C activation assay compared to native detergent-solubilized rabbit thrombomodulin, will have only 80% or less of the activity of the same amount (mass) of native thrombomodulin in a standard assay measuring thrombin-mediated conversion of fibrinogen to fibrin. One preferred analog of this invention has 50% or less of the activity of the same amount of native thrombomodulin in the fibrin assay. These capacities are measured using standard assays described herein.

This invention further provides for sterile compositions for treating thrombotic disease in mammals comprising a unit dosage of a thrombomodulin analog having one or more of the above-noted properties. The preferred analogs are as described above for various methods.

This invention further provides for methods of increasing the in vivo circulating half-life of a thrombomodulin analog comprising removing all or most of the sugar moieties, e.g., in the 6 EGF-like domains.

DETAILED DESCRIPTION OF THE INVENTION

Figure 1:
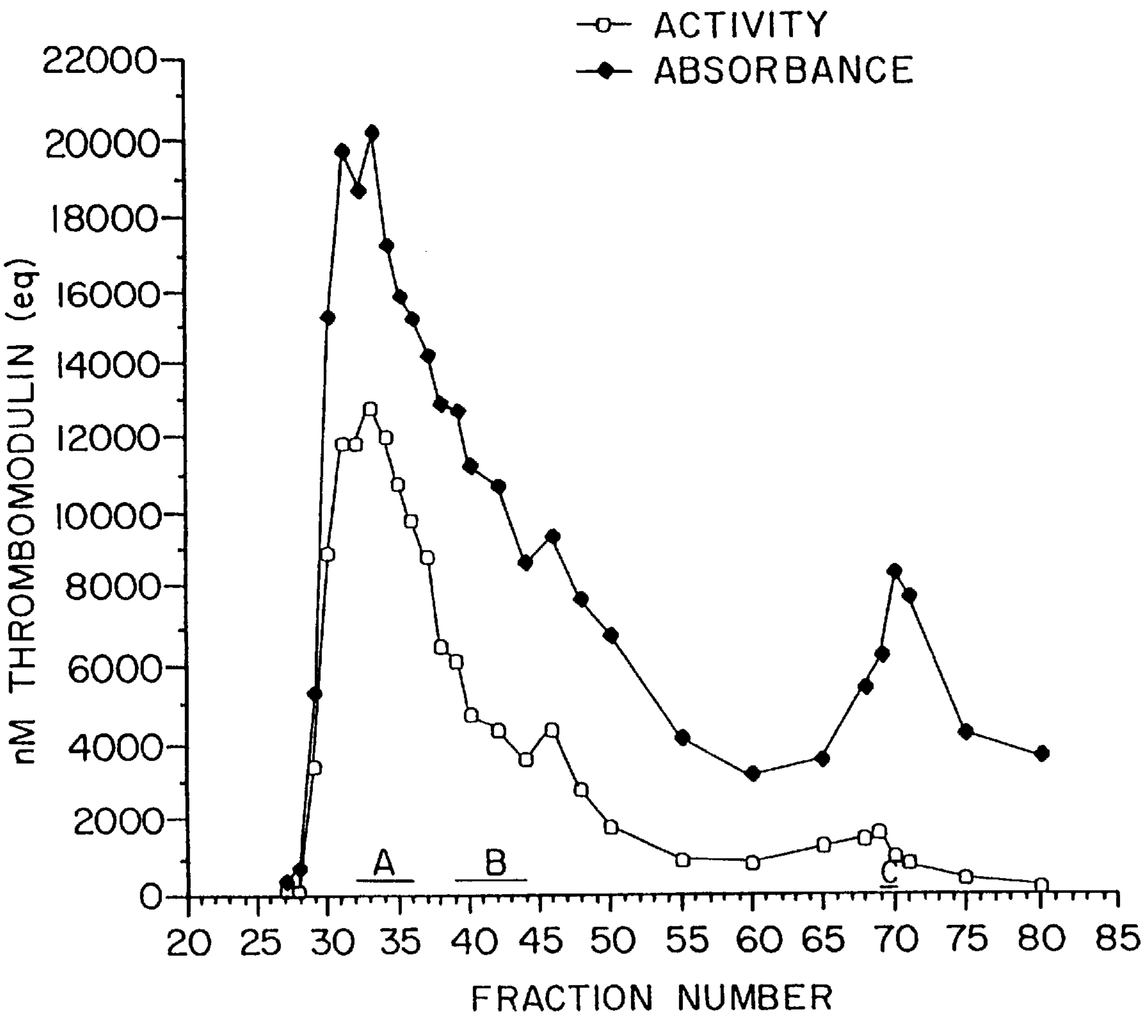
FIG. 1 shows an elution and activity profile of a soluble $TM_E$ (Sf9) preparation resolved on a Mono Q column.
Figure 2A:
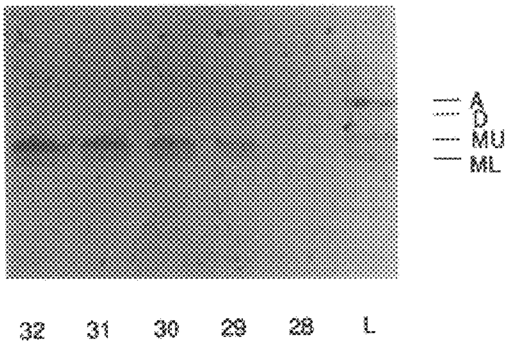
FIG. 2 shows SDS-PAGE analysis of samples from the column profile shown in FIG. 1.
Figure 2B:
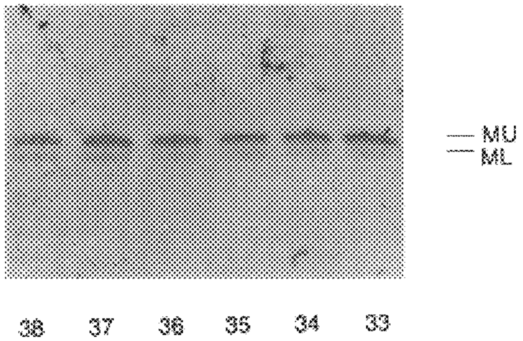
Figure 2C:
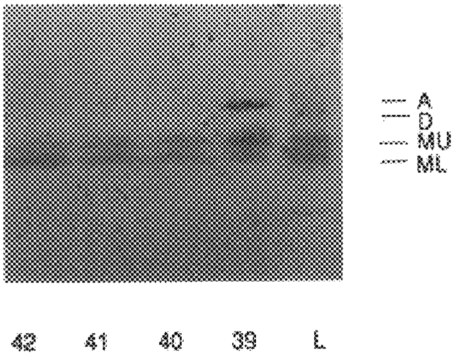
Figure 2D:
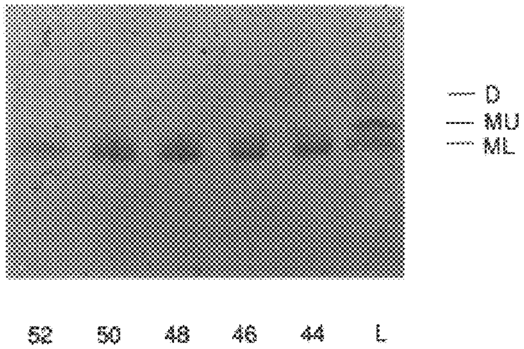

In accordance with the present invention, new TM analogs, methods, and compositions are provided which can treat thrombotic disease. They are based on a single-chain thrombomodulin (TM) or thrombomodulin analog which is resistant to protease cleavage. In addition, other modifications can be introduced which result in other improved properties of an antithrombotically effective pharmaceutical, e.g., wherein the TM exhibits a reduced capacity to inhibit the direct procoagulant activities of thrombin or exhibits other properties such as thrombin-mediated conversion of fibrinogen to fibrin, oxidation resistance, glycosylation resistance, increased in vivo half-life, etc. Pharmacologists prefer drugs which contain a single therapeutically effective homogeneous composition. Such drugs are preferred because they are less likely to induce undesired side effects than drugs containing multiple species, including species containing undefined biological effectiveness. This invention has the advantage of containing a more biologically pure species, often also being chemically pure, which does not have the disadvantages of prior art products.

The prior art thrombomodulin compositions, particularly those produced by recombinant techniques in heterologous cells, have been studied extensively by the present inventors in order to determine parameters for the structure of the polypeptide which provide optimal pharmaceutical utility. In the course of these investigations, it was found that, surprisingly, thrombomodulin preparations previously thought to contain pure, single-chain polypeptides were, in fact, heavily contaminated with thrombomodulin polypeptides having an internal peptide cleavage, but wherein the polypeptide continued to copurify with single-chain forms of TM, because the cysteine bonding between the separate chains caused the two-chain form of the TM to behave similarly to a single-chain form under purification conditions. This would apply both to full-length native TM, as well as to soluble TM molecules.

This previously unappreciated problem was discovered, in part, by careful analysis of these preparations, which revealed that the recombinantly produced thrombomodulin demonstrated two-phase non-linear binding properties double-reciprocal plot analysis indicated the presence of two species with different binding affinities in the composition. This led to further investigations as to the nature of the different species. Careful analysis of TM preparations using sodium dodecyl sulfate-polyacrylamide gel electrophoresis (SDS-PAGE) run under reducing, non-reducing, or native conditions and employing sensitive detection techniques, e.g., silver or immunological staining, led to the discovery that there was a second immunoreactive band having an apparent molecular weight of about 80 kilodaltons, in addition to the expected 94 kilodalton band of particular soluble TM analogs, on such gels. This composition was then shown to have a second N-terminal amino acid sequence consistent with the presence of an internal N-terminus. This is likely the result of a protease cleavage, at a location within the TM sequence, indicating that the apparently single-chain form of TM was contaminated with a cleaved two-chain species. This species is cleaved rear or within the thrombin binding site of the TM. Thus, while the physical characteristics of the two-chain form were so similar to the single-chain form as to result in copurification, in fact the biological activity, e.g., the binding properties, of the mixture appears to be affected by this previously unrealized distinct species. The present invention provides thrombomodulin analog compositions substantially free of such two-chain contaminants.

In another aspect of this invention, there are provided other improved compositions of thrombomodulin. For example, it has also been discovered that TM analogs, especially those produced by heterologous cells under recombinant conditions have an N-terminus produced by signal sequence processing of the amino acid sequences upstream of the mature N-terminus. In fact, the product exhibits heterogeneity at the amino terminus. There are two processing sites, one which provides the native N-terminal amino acid 1, and a second site which, when used, produces a cleavage product containing two more amino acids at the N-terminus, e.g., starting at amino acid −2. By modification of the DNA sequence encoding the N-terminus of the TM polypeptide, the signal sequence processing site can be modified to provide a single N-terminal processing site, and therefore a single N-terminus for the resultant TM analogs. Thus, a TM analog which deletes the first three amino acids of the native molecule provides a signal sequence processing site which is unique, thereby producing a polypeptide composition with a single N-terminal sequence.

Still further, the elimination of internal cleavages to produce a single-chain TM analog results in a composition having a homogeneous carboxy terminus. Constructs which are resistant to protease or other proteolytic cleavage are made so as to provide single C-termini as well. This can be accomplished by removal or modification of protease cleavage sites. For example, by deleting a portion of the C-terminal region of the polypeptide which is not critical to biological function in pharmaceutical applications, a polypeptide can be provided which terminates in a -Pro-Pro sequence at amino acids 489–490, which sequence is especially resistant to exocarboxypeptidase activity.

In another embodiment, this invention also provides for methods of increasing the in vivo half-life of TM analogs by modifying or deleting particular native glycosylation patterns, or removing protease-sensitive sequences. Our early studies have indicated that the proteolysis-resistant form of soluble TM has a longer circulating half-life in an animal. Thus, it is likely that a physiological mechanism which contributes to TM inactivation is proteolysis at, or near, the identified region of the protein. By modifying this segment of the sequence to avoid inactivation, a much more effective therapeutic agent is produced. Increased half-life is advantageous for TM therapy because it permits administration of lesser amounts of TM to achieve equivalent pharmacological effect compared to the native drug a biological half-life which is at least greater than a few minutes provides for a more predictable therapeutic regimen.

In addition, these soluble thrombomodulin analogs can be produced economically and are easily purified and administered. A variety of therapeutic uses are anticipated, particularly with respect to anticoagulant and/or antithrombotic therapies. In order to fully appreciate the invention, the following detailed description is set forth.

I. Biological Activity of Thrombomodulin

The underlying pathology of thrombotic disorders is that a clot forms in response to a stimulus such as, for example, a damaged vessel wall. This stimulus triggers the coagulation cascade and thus generates thrombin which has the ability to convert fibrinogen to fibrin, the matrix of the clot. Thrombomodulin is an endothelial cell membrane protein that acts as a receptor for thrombin. In humans it is distributed on the endothelium of the blood vessels and lymphatics of all organs except the central nervous system. Thrombin has the ability to bind reversibly to thrombomodulin. When bound to thrombomodulin, thrombin is converted from a procoagulant enzyme to an anticoagulant enzyme. The thrombin/thrombomodulin complex inhibits the coagulation cascade in at least two distinct ways. First, thrombin's binding to thrombomodulin potentiates thrombin-mediated activation of protein C. Activated protein C inactivates other procoagulant components of the coagulation cascade, such as Factors Va and VIIIa, which in turn inhibits the conversion of more prothrombin to thrombin. Thrombin-mediated activation of protein C is greatly enhanced when thrombin is bound to thrombomodulin, i.e., the rate of protein C activation increases at least 1000-fold. Secondly, binding to thrombomodulin has direct anticoagulant effects such as the inhibition of thrombin-mediated conversion of fibrinogen to fibrin and thrombin-mediated activation and aggregation of platelets. Although normally an integral component of the endothelial cell membrane, thrombomodulin can be released from the membrane in the presence of sufficient detergent and retains the ability to bind to thrombin when in solution.

The preferred thrombomodulin analogs of this invention will protect against thrombus formation when administered systemically because they will inhibit the generation of thrombin without disturbing other coagulation parameters, e.g., the activation and aggregation of platelets. Thus the use of soluble thrombomodulin analogs will be effective at preventing thrombus formation, yet is safer than native thrombomodulin and other antithrombotics known in the art.

Diseases in which thrombus formation plays a significant etiological role include myocardial infarction, disseminated intravascular coagulation, deep vein thrombosis, pulmonary embolism, septic shock, acute respiratory distress syndrome, unstable angina, and other arterial or venous occlusive conditions. The thrombomodulin analogs of this invention are useful in all of these, as well as in other diseases in which thrombus formation is pathological. By useful it is meant that the compounds are useful for treatment, either to prevent the disease or to prevent its progression to a more severe state. The compounds of this invention also provide a safe and effective anticoagulant, for example, in patients receiving bioprostheses, such as heart valves. These compounds may replace heparin and warfarin in the treatment of, for example, pulmonary embolism or acute myocardial infarction.

In particular these compounds would find a role in the prevention of deep vein thrombosis (DVT), for instance after surgery. The formation of blood clots in the leg is itself a non-fatal condition but is very closely tied to the development of pulmonary embolism (PE), which is difficult to diagnose and can be fatal. Despite the investigation and clinical use of several prophylactic regimens, DVT and the resulting PE remain a significant problem in many patient populations and particularly in patients undergoing orthopedic surgery. Existing prophylactic treatments such as heparin, warfarin, and dextran typically reduce the incidence of DVT in orthopedic surgery patients from more than 50% in patients at risk receiving no prophylaxis to 25–30% among treated patients. There are serious side effects, primarily bleeding complications. Currently, daily laboratory tests and adjustments in dosage are required to minimize bleeding episodes while retaining some efficacy. Based on the shortcomings of existing prophylactics, an antithrombotic which is effective at preventing DVT without predisposing the patient to bleeding could make a significant impact on patient recovery and well-being.

Angioplasty is a procedure frequently used for restoring patency in occluded arteries. Although patency may be restored, it is inherent in an angioplasty procedure that the endothelial lining of the artery is severely damaged, and blood clots frequently begin to form. Soluble thrombomodulin analogs administered in conjunction with angioplasty will prevent this deleterious side effect.

Many acute thrombotic and embolic diseases are currently treated with fibrinolytic therapy in order to remove the thrombus. The condition that has been most investigated is acute myocardial infarction (heart attack). Agents currently in use for treating acute myocardial infarction include streptokinase, tissue plasminogen activator, and urokinase. Use of these agents can lead to serious bleeding complications. Patients who have had a thrombus removed by fibrinolytic therapy and in whom the blood flow has been restored frequently reocclude the affected vessel, i.e., a clot reforms. Attempts have been made to prevent the reocclusions by increasing the dose or time of treatment with a thrombolytic agent, but the incidence of bleeding then increases. Thus the therapeutic index for these drugs is narrow.

The use of thrombomodulin analogs provides protection against reocclusion, in part, because its action is local, i.e., where thrombin is being generated or being released from a clot. Therefore, when used in combination with a thrombolytic agent whose dose can then be decreased, the risk of bleeding can be substantially reduced.

Administration of single-chain thrombomodulin or TM analogs can be accomplished by a bolus intravenous injection, by a constant intravenous infusion, or by a combination of both routes. Also, soluble thrombomodulin mixed with appropriate excipients may be taken into the circulation from an intramuscular site. Systemic treatment with thrombomodulin analogs can be monitored by determining the activated partial thromboplastin time (APTT) on serial samples of blood taken from the patient. The coagulation time observed in this assay is prolonged when a sufficient level of thrombomodulin is achieved in the circulation. However, this is a systemic measurement of efficacy, and the inventors have discovered that an effective dose of soluble TM analog does not necessarily affect the APTT. As used herein, a therapeutically effective dose is defined as that level of TM analog sufficient to prevent formation of pathological clots. Dosing levels and regimens can be routinely adjusted by one of ordinary skill in the art so that an adequate concentration of thrombomodulin is maintained as measured by, for example, the activated partial thromboplastin clotting time (APTT), the thrombin clotting time (TCT), or conversion of protein C to activated protein C (APC) assays.

Several methods are known for the detection and monitoring of thrombotic disease. Deep venous thrombosis can be detected, for example, by contrast venography, (Kerrigan, G. N. W., et al., (1974) *British Journal of Hematology* 26:469), Doppler ultrasound (Barnes, R. W. (1982) *Surgery Clinics in North America* 62:489–500), $^{125}$I-labeled fibrinogen uptake scanning (Kakkar, V. V., et al., (1972) *Archives of Surgery* 104:156 Kakkar, V. V., et al., (1970) *Lancet* i:540–542), impedance plethysmography (Bynum, L. J. et al., (1978) *Annals of Internal Medicine* 89:162), and thromboscintoscan (Ennis, J. T. and Elmes, R. J. (1977) *Radiology* 125:441). These methods are useful to monitor the efficacy of the methods and compositions described herein.

II. TM analogs

A DNA sequence encoding the full-length native human thrombomodulin protein has been isolated (European Patent Application No. 88870079.6, which is incorporated herein by reference). The cDNA sequence encodes a 60.3 kDa protein of 575 amino acids, which includes a signal sequence of about 18 amino acids.

The sequences for bovine, mouse, and human thrombomodulin exhibit a high degree of homology with one another. By analogy with other proteins, the structure of thrombomodulin can be presumptively divided into domains. The term "domain" refers to a discrete amino acid sequence that can be associated with a particular function or characteristic. Typically, a domain exhibits a characteristic tertiary structural unit. The full-length thrombomodulin gene encodes a precursor peptide containing the following domains:

| Approximate Amino Acid Position | Domain |
|---|---|
| −18—1 | Signal sequence |
| 1–226 | N-terminal domain (lectin domian; L |
| 227–462 | 6'EGF-like domains (E) |
| 463–497 | O-linked Glycosylation (O) |
| 498–521 | Stop Transfer Sequence (transmembrane domain) |
| 522–557 | Cytoplasmic domain |

See C. S. Yost et al., (1983) *Cell,* 34:759–766 and D. Wen et al., (1987) *Biochemistry,* 26:4350–4357, both incorporated herein by reference.

In the nomenclature used here, the subscript refers to the domains contained in the TM analog: L=the lectin domain, E=the 6 EGF-like domains, O=the O-linked glycosylation domain, M=the transmembrane domain, and C=the cytoplasmic domain. Thus, TM analog 6h/227–462, corresponds to a $TM_E$ analog $TM_E$(Sf9) indicates that it is expressed in insect cells, $TM_{LEO}$(CHO) indicates that it is expressed in CHO cells, and TMD123 (Zushi, M., Gomi, K., Yamamoto, S., Maruyama, I., Hayashi, T., and Suzuki, K. (1989) *J. Biol. Chem.* 264, 10351–10353) and TMD1 (Parkinson, J. F., Grinnell, B. W., Moore, R. E., Hoskins, J., Vlahos, C. J., and Bang, N. U. (1990) *J. Biol. Chem.* 265, 12602–12610) corresponds to $TM_{LEO}$ analogs.

Particularly preferred single-chain TM analog compositions are those that have one or more of the following characteristics:

(i) they exhibit protease resistance, (ii) they have homogeneous N- or C-termini, (iii) they have been post-translationally modified, e.g., by glycosylation of at least some of the glycosylation sites of native thrombomodulin, (iv) they have linear double-reciprocal thrombin binding properties, (v) they are soluble in aqueous solution in relatively low amounts of detergents and typically lack a stop transfer (transmembrane) sequence, (vi) they retain activity after exposure to oxidants, (vii) when bound to thrombin, they potentiate the thrombin-mediated activation of protein C but have a reduced ability to inhibit the direct pro-coagulant activities of thrombin such as the conversion of fibrinogen to fibrin or the activation and aggregation of platelets.

Assays for the last two characteristics can be run on an automatic coagulation timer according to the manufacturer's specifications; Medical Laboratory Automation Inc. distributed by American Scientific Products, McGaw Park, Ill. (See also H. H. Salem et al., (1984) *J. Biol. Chem.,* 259:12246–12251, which is incorporated herein by reference). In comparison to native thrombomodulin, preferred TM analogs have been modified to embrace the 6 epidermal growth factor [EGF]-like domains and may also contain the O-linked glycosylation and/or lectin domains.

In a preferred embodiment, soluble TM analogs are oxidation resistant. This refers to analogs that retain activity after exposure to oxidants. Such analogs are described in detail in co-pending co-assigned U.S. application Ser. No. 07/506,325, filed Apr. 9, 1990, incorporated herein by reference.

For purposes of the present invention, the following terms are defined:

"Protease site" as used herein refers to an amino acid or series of amino acids in a TM polypeptide which define a recognition, binding, cleavage, or other site susceptible to the activity of a protease. For example, when one or more amino acid residues encompassed by this site are substituted by another amino acid residue(s) or are deleted the protease is no longer able to cleave the TM at that site. This term also encompasses regions of the TM molecule which are inherently susceptible to proteases, e.g., by being conformationally exposed and available to a protease activity.

"Protease cleavage site" as used herein refers to the precise location at which a protease cleaves the TM polypeptide analog.

"Single N-terminus" and "single C-terminus" are used herein to have their literal meanings which functionally refer to the property of the composition, e.g., wherein, upon conventional sequential amino acid sequence analysis, each degradation cycle results in the removal of an amino acid residue which is essentially devoid of a different amino acid residue. Thus, after several cycles, e.g., 10 cycles, of step-wise removal of the N-terminal amino acids, essentially only one amino acid is recovered at each cycle. In particular, no more heterogeneity in sequence is detected than would be statistically expected from a completely pure single-chain polypeptide according to the analytic procedure used.

"Single-chain TM" refers to a composition of TM which contains substantially all uncleaved peptide chains. The polypeptides in a single-chain composition need not all exhibit identical amino or carboxy terminal ends.

"Two-chain TM" refers to a composition containing physically detectable amounts, typically in excess of about 0.5–3%, of polypeptide which has a broken peptide bond.

"Devoid of two-chain thrombomodulin" as used herein means that the composition comprises essentially all single-chain TM. Typically, the amount of two-chain TM is less than about 25% by molar amount, more typically less than 15%, preferably less than about 10%, more preferably less than 5%, and in particularly preferred embodiments, less than 3%. Alternatively, the amount of two-chain TM in a composition is less than that which would cause a significant decrease in the specific activity of pure single-chain TM, e.g., the amount of two-chain TM is less than the amount which alters a linear double reciprocal plot defined herein. Thus, two-chain TM molecules are present in the form of a polypeptide chain having at least one scission which results in the production of additional N- and/or C-termini.

"Substantially retains the biological activity of native thrombomodulin" and similar terms, as used herein, means that the thrombomodulin shares biological activities with a native membrane bound TM molecule. Generally, the activity in units per milligram of protein is at least about 50%, ordinarily 75%, typically 85%, more typically 95%, preferably 100% and more preferably over 100% of the activity of native thrombomodulin. This biological activity can be that of thrombin-mediated activation of protein C (APC) of activated partial thromboplastin clotting time (APTT), of thrombin clotting time (TCT), or of any of TM's biological, preferably therapeutic, activities. The native standard of comparison is a full-length membrane bound version of TM, but in many cases, a soluble TM comprising the lectin/EGF/O-linked domain ($TM_{LEO}$) can be used as a more convenient standard.

"Glycosylation sites" refer to amino acid residues which are recognized by a eukaryotic cell as locations for the attachment of sugar residues. The amino acids where sugars are attached are typically Asn (for N-linked sugars), threonine or serine (for O-linked sugars) residues. The specific site of attachment is typically signaled by a sequence of amino acids, e.g., Asn-X-(Thr or Ser) for most N-linked attachment and (Thr or Ser)-X-X-Pro for most O-linked attachment, where X is any amino acid. The recognition sequence for glycosaminoglycans (a specific type of sulphated sugar) is generally Ser-Gly-X-Gly, but can also be X-Ser-Gly-X-Val. The terms N-linked and O-linked refer to the chemical group that serves as the attachment site between the sugar moiety and the amino acid residue. N-linked sugars are attached through an amido group; O-linked sugars are attached through an hydroxyl group.

"In vivo circulating half-life" refers to the average time it takes an administered plasma activity in a mammal to decrease by one half.

"Native thrombomodulin" refers to the full length protein as it occurs in nature. When biological activities are described with reference to the native TM, the term embraces a detergent solubilized aqueous form. Often, in the context of comparison to an activity, a transfected soluble polypeptide may exhibit substantially identical properties.

"O-linked glycosylation domain" refers to the sequence of amino acids numbered from 463 through 485 of the native thrombomodulin sequence as depicted in Table 1.

"Oxidation resistant analogs" refers to analogs of thrombomodulin which are able to maintain a substantial amount of biological activity after exposure to oxidizing agent such as oxygen radicals, Chloramine T, hydrogen peroxide, or activated neutrophils.

"Pharmaceutical excipients" refers to non-toxic, medically-acceptable materials which are used to complete a medical therapeutic. These materials can be inert, such as water and salt, or biologically active, such as an antibiotic or analgesic.

"Reduced ability" refers to a statistically meaningful lowering of a biological property. The property is unlimited and the measurement or quantification of the property is by standard means.

"Sugar residues" refers to hexose and pentose carbohydrates including glucosamines and other carbohydrate derivatives and moieties which are covalently linked to a protein.

"Sulfate substituents" are sulfur-containing substituents on pentose or hexose sugars.

"Thrombin-mediated conversion of fibrinogen to fibrin" refers to the enzymatic activity by which thrombin cleaves the precursor protein fibrinogen to make fibrin monomer, which subsequently polymerizes to form a blood clot.

"Thrombotic disease" refers to a pathogenic condition in a mammal characterized by the formation of one or more thrombi that are or can be detrimental to the health of the mammal.

"Thrombomodulin analogs" are peptides which substantially retain the biological activity of natural TM, as discussed above, and which have a molecular structure different from that of a natural version TM. For example, the term refers to proteins having an amino acid sequence identical or homologous with that of native thrombomodulin, to insoluble and soluble thrombomodulin peptides or fragments, and to oxidation resistant TM species, all having thrombomodulin-like activity. These compounds also include derivatives and molecules comprising amino acid changes which do not significantly decrease the protein C activation cofactor properties of the protein when compared with native TM.

"Transfer vector" refers to a vector cotransfected into another cell, e.g., an insect cell, with, e.g., a wild-type baculovirus. The transfer vector is constructed in such a way as to encourage a recombination between a viral, e.g., the baculovirus, genome and the transfer vector, e.g., replacing the baculovirus polyhedron gene with a heterologous target gene. Where a vector is being maintained by a host cell, the vector may either be stably replicated by the cells during mitosis as an autonomous structure, or is incorporated within the host's genome.

As used herein, a "soluble TM analog" is a TM analog which is soluble in an aqueous solution, and typically can be secreted by a cell. For pharmacological administration, the soluble TM analog or an insoluble analog comprising the native cytoplasmic domain, or analog may optionally be combined with phospholipid vesicles, detergents, or other similar compounds well known to those skilled in the art of pharmacological formulation. The preferred TM analogs of the present invention are soluble in the blood stream, making the analogs useful in various anticoagulant and other therapies. These modifications typically do not significantly affect many activities relative to native thrombomodulin, e.g., affinity for thrombin or activity in protein C activation.

Two preferred analogs encompass the 6 EGF-like domains and are 4t/227–462 where the analog has the last four residues of the human tissue plasminogen activator signal peptide and 6h/227–462 where the 6h represents the last six residues of the hypodermin A signal sequence. More preferred are these analogs rendered oxidation resistant by substitution of the methionine at position 388 with leucine.

Another preferred embodiment is an analog corresponding to amino acids 3–490, with modifications to Met388, Arg456, HIS457, Ser474, and deletions at the N- and C-termini. This embodiment is particularly useful when expressing the gene in eukaryotic cells, e.g., in animal cells, vertebrate cells, insect cells mammalian cells, human cells, etc., in particular, CHO and CHL1 cells.

A. General Methods For Making TM Analogs

This invention embraces molecular genetic manipulations that can be achieved in a variety of known ways. The recombinant cells, plasmids, and DNA sequences of the present invention provide a means to produce pharmaceutically useful compounds wherein the compound, secreted from recombinant cells, is a soluble derivative of thrombomodulin.

Generally, the definitions of nomenclature and descriptions of general laboratory procedures used in this application can be found in J. Sambrook et al., *Molecular Cloning, A Laboratory Manual,* (1989) Cold Spring Harbor Laboratory, Cold Spring Harbor, N.Y. The manual is hereinafter referred to as Sambrook and is hereby incorporated by reference. In addition, Ausubel et al., eds., *Current Protocols in Molecular Biology,* (1987 and periodic updates) Greene Publishing Associates, Wiley-Interscience, New York, discloses methods useful in the present application.

All enzymes are used according to the manufacturer's instructions.

Oligonucleotides that are not commercially available can be chemically synthesized according to the solid phase phosphoramidite triester method first described by S. L. Beaucage and M. H. Caruthers, (1981) *Tetrahedron Letts.,* 22(20):1859–1862 using an automated synthesizer, as described in D. R. Needham-VanDevanter et al., (1984) *Nucleic Acids Res.,* 12:6159–6168. Purification of oligonucleotides was by either native acrylamide gel electrophoresis or by anion-exchange HPLC as described in Pearson, J. D., and Regnier, F. E. (1983) *J. Chrom.,* 255:137–149. Nucleotide sizes are given in either kilobases (kb) or base pairs (bp). These are estimates derived from agarose or acrylamide gel electrophoresis or from published DNA sequences.

The sequence of the cloned genes and synthetic oligonucleotides can be verified using the chemical degradation method of Maxam, A. M., et al., (1980) *Methods in Enzymology,* 65:499–560, or similar methods. The sequence can be confirmed after the assembly of the oligonucleotide fragments into the double-stranded DNA sequence using the method of Maxam and Gilbert, supra, or the chain termination method for sequencing double-stranded templates of Wallace, R. B., et al., (1981) *Gene,* 16:21–26. Southern Blot hybridization techniques were carried out according to Southern et al., (1975) *J. Mol. Biol.,* 98:503.

Embodiments of this invention often involve the creation of novel peptides and genes by in vitro mutagenesis. Target genes are isolated in intermediate vectors and cloned for amplification in prokaryotes such as *E. coli,* Bacillus, or Streptomyces. Most preferred is *E. coli* because that organism is easy to culture and more fully understood than other species of prokaryotes. The Sambrook manual contains methodology sufficient to conduct all subsequently described clonings in *E. coli.* Strain MH-1 is preferred unless otherwise stated. All *E. coli* strains are grown on Luria broth (LB) with glucose, or M9 medium supplemented with glucose and acid-hydrolyzed casein amino acids. Strains with resistance to antibiotics were maintained at the drug concentrations described in Sambrook. Transformations were performed according to the method described by Morrison, D. A. (1977) *J. Bact.,* 132:349–351 or by Clark-Curtiss, J. E., and Curtiss, R. (1983) *Methods in Enzymology,* 101:347–362, Eds. R. Wu et al., Academic Press, New York. Representative vectors include pBR322 and the pUC series which are available from commercial sources.

B. Gene Synthesis

The gene encoding native thrombomodulin has been isolated and sequenced from several species, both in its genomic form and as a cDNA (Jackman, R., et al., (1986) *Proc. Natl. Acad. Sci. U.S.A.* 83:8834–8838 and (1987) 84:6425–6429, both of which are herein incorporated by reference).

Publication of the full length DNA sequence encoding human thrombomodulin and thrombin facilitates the preparation of genes and is used as a starting point to construct DNA sequences encoding TM peptides. See, e.g., Genbank Register c/o IntelliGenetics, Inc., Mountain View, Calif. The peptides of the present invention are preferably soluble derivatives which lack the stop transfer sequence of TM in addition to having internal amino acid substitutions. Furthermore, these analogs are secreted from eukaryotic cells which have been transfected or transformed with plasmids containing genes which encode these polypeptides. Methods for making modifications, such as amino acid substitutions, deletions, or the addition of signal sequences to cloned genes are known. Specific methods used herein are described below.

The full-length gene for thrombomodulin can be prepared by several methods. Human genomic libraries are commercially available. oligonucleotide probes, specific to these genes, can be synthesized using the published gene sequence. Methods for screening genomic libraries with oligonucleotide probes are known. The publication of the gene sequence for thrombomodulin demonstrates that there are no introns within the coding region. Thus a genomic clone provides the necessary starting material to construct an expression plasmid for thrombomodulin using known methods.

A thrombomodulin encoding DNA fragment can be retrieved by taking advantage of restriction endonuclease sites which have been identified in regions which flank or are internal to the gene. (Jackman, R. W., et al., (1987) *Proc. Natl. Acad. Sci. U.S.A.,* 84:6425–6429).

Alternatively, the full length genes can also be obtained from a cDNA library. For example, messenger RNA prepared from endothelial cells provides suitable starting material for the preparation of cDNA. A cDNA molecule containing the gene encoding thrombomodulin is identified as described above. Methods for making cDNA library are well known (See Sambrook, supra).

Genes encoding TM peptides may be made from wild-type TM genes first constructed using the gene encoding full length thrombomodulin. A preferred method for producing wild-type TM peptide genes for subsequent mutation combines the use of synthetic oligonucleotide primers with polymerase extension on a mRNA or DNA template. This polymerase chain reaction (PCR) method amplifies the desired nucleotide sequence. U.S. Pat. Nos. 4,683,195 and 4,683,202 describe this method. Restriction endonuclease sites can be incorporated into the primers. Genes amplified by the PCR reaction can be purified from agarose gels and cloned into an appropriate vector. Alterations in the natural gene sequence can be introduced by the techniques of in vitro mutagenesis or by use of the polymerase chain reaction with primers that have been designed to incorporate appropriate mutations. See Innis, M. et al., eds. (1990), PCR Protocols: A Guide to Methods and Applications, Academic Press.

The TM peptides described herein are typically secreted when expressed in eukaryotic cell culture. Secretion may be obtained by the use of the native signal sequence of the thrombomodulin gene. Alternatively, genes encoding the TM peptides of the present invention may be ligated in proper reading frame to a signal sequence other than that corresponding to the native thrombomodulin gene. For example, the signal sequence of t-PA, (see WO 89/00605 incorporated herein by reference) or of hypodermin A or B (see EP 326,419 which is incorporated hereby by reference) can be linked to the polypeptide (See Table 2). In one preferred embodiment of the present invention, use is made of the signal sequence of t-PA which contains the second intron of the human t-PA gene. The inclusion of the intron enhances the expression level of the adjacent structural gene.

With some analogs of this invention, those portions of the gene encoding the stop transfer and cytoplasmic domains of the carboxyl terminal region of the native thrombomodulin gene are deleted. Therefore, it is necessary to add a stop codon so that translation will be terminated at the desired position. Alternatively, a stop codon can be provided by the desired expression plasmid. Additionally, a polyadenylation sequence can be utilized to ensure proper processing of the mRNA in eukaryotic cells encoding the TM analog. Also, it may be useful to provide an initiation codon, if one is not present, for expression of the TM peptides. Such sequences may be provided from the native gene or by the expression plasmid.

Cloning vectors suitable for replication and integration in prokaryotes or eukaryotes and containing transcription and translation terminators, initiation sequences, and promoters useful for regulation of the expression of TM peptides are described herein. The vectors are comprised of expression cassettes containing at least one independent terminator sequence, sequences permitting replication of the plasmid in both eukaryotes and prokaryotes, i.e., shuttle vectors, and selection markers for both prokaryotic and eukaryotic systems.

C. Expression of TM Peptides in Prokaryotic Cells

In addition to the use of cloning methods in *E. coli* for amplification of nucleic acid sequences it may be desirable to express TM analogs in prokaryotes. As discussed in greater detail below, the carbohydrate moieties of the mature protein are not essential for activity as a cofactor for the activation of protein C but do have an effect on the direct anticoagulant properties of the TM analogs as well as the molecule's half-life in circulation. Expression of thrombomodulin analogs in *E. coli* has provided a useful tool for analysis of this issue. It is possible to recover a therapeutically functional protein from *E. coli* transformed with an expression plasmid encoding a soluble TM analog.

Methods for the expression of cloned genes in bacteria are well known. To obtain high level expression of a cloned gene in a prokaryotic system, it is often essential to construct expression vectors which contain, at the minimum, a strong promoter to direct mRNA transcription termination. Examples of regulatory regions suitable for this purpose are the promoter and operator region of the *E. coli* β-galactosidase gene, the *E. coli* tryptophan biosynthetic pathway, or the leftward promoter from the phage lambda. The inclusion of selection markers in DNA vectors transformed in *E. coli* are useful. Examples of such markers include the genes specifying resistance to ampicillin, tetracycline, or chloramphenicol.

See Sambrook, supra, for details concerning selection markers and promoters for use in *E. coli.* In one described embodiment of this invention, pUC19 is used as a vector for the subcloning and amplification of desired gene sequences.

D. Expression of TM Peptides in Eukaryotic Cells

It is expected that those of skill in the art are knowledgeable in the expression systems chosen for expression of the desired TM peptides and no attempt to describe in detail the various methods known for the expression of proteins in eukaryotes will be made.

The DNA sequence encoding a soluble TM analog can be ligated to various expression vectors for use in transforming host cell cultures. The vectors typically contain marker genes and gene sequences to initiate transcription and translation of the heterologous gene.

The vectors preferably contain a marker gene to provide a phenotypic trait for selection of transformed host cells such as dihydrofolate reductase, metallothionein, hygromycin, or neomycin phosphotransferase. The nuclear polyhedral viral protein from *Autographa californica* is useful to screen transfected insect cell lines from *Spodoptera frugiperda* and *Bombyx mori* to identify recombinants. For yeast, Leu-2, Ura-3, Trp-1, and His-3 are known selectable markers (*Gene* (1979) 8:17–24). There are numerous other markers, both known and unknown, which embody the above scientific principles, all of which would be useful as markers to detect those eukaryotic cells transfected with the vectors embraced by this invention.

Of the higher eukaryotic cell systems useful for the expression of TM analogs, there are numerous cell systems to select from. Illustrative examples of mammalian cell lines include RPMI 7932, VERO, and HeLa cells, Chinese hamster ovary (CHO) cell lines, W138, BHK, COS-7, C127, or MDCK cell lines. A preferred mammalian cell line is CHL-1 or CHO. When CHL-1 is used, hygromycin is included as a eukaryotic selection marker. CHL-1 cells are derived from RPMI 7932 melanoma cells, a readily available human cell line. The CHL-1 cell line has been deposited with the ATCC according to the conditions of the Budapest Treaty and has been assigned #CRL 9446, deposited Jun. 18, 1987. Cells suitable for use in this invention are commercially available from the American Type Culture Collection. Illustrative insect cell lines include *Spodoptera frugiperda* (fall Armyworm) and *Bombyx mori* (silkworm).

As indicated above, the expression vector, e.g., plasmid, which is used to transform the host cell, preferably contains gene sequences to initiate the transcription, and sequences to control the translation of the TM peptide gene sequence. These sequences are referred to as expression control sequences. When the host cell is of insect or mammalian origin, illustrative expression control sequences include but are not limited to the following: the retroviral long terminal repeat promoters ((1982) *Nature,* 297:479–483), SV40 promoter ((1983) *Science,* 222:524–527, thymidine kinase promoter (Banerji, J., et al., (1982) *Cell,* 27:299–308), or the beta-globin promoter (Luciw, P. A., et al., (1983) *Cell,* 33:705–716). The recipient vector nucleic acid containing the expression control sequences is cleaved using restriction enzymes and adjusted in size as necessary or desirable. This segment is ligated to a DNA sequence encoding TM peptide by means well known in the art.

When higher animal host cells are employed, polyadenylation or transcription termination sequences normally need to be incorporated into the vector. An example of a polyadenylation sequence is the polyadenylation sequence from SV40, which may also function as a transcription terminator.

Genes incorporated into the appropriate vectors can be used to direct synthesis of proteins in either transient expression systems or in stable clones. In the former case yields are low, but the experiments are quick. In the latter case it takes more time to isolate high producing clones. Different vectors may be used for the two different types of experiments. In particular, in the case of transient expression, sequences may be included within the plasmid that allow the plasmid to replicate to a high copy number within the cell. These sequences may be derived from a virus such as SV40 (e.g., Doyle, C. et al., (1985) *J. Cell Biol.,* 100:704–714) or from chromosomal replicating sequences such as murine autonomous replicating sequences (Weidle et al., (1988) *Gene,* 73:427–437). The vector for use in transient expression will also often contain a strong promoter such as the SV40 early promoter (e.g., van Zonnenfeld, A. et al., (1987) *Proc. Natl. Acad. Sci. U.S.A.,* 83:4670–4674) to control transcription of the gene of interest. While transient expression provides a rapid method for assay of gene products, the plasmid DNA is not incorporated into the host cell chromosome. Thus, use of transient expression vectors does not provide stable transfected cell lines. A description of a plasmid suitable for transient expression is provided by Aruffo, A., and Seed, B. (1987) *Proc. Natl. Acad. Sci. U.S.A.,* 84:8573–8577.

TM analogs may alternatively be produced in the insect cell lines described above using the baculovirus system. This system has been described by Luckow, V. A., and Summers, M. D. (1988) *Bio/Technology,* 6:47–55. Generally, this expression system provides for a level of expression higher than that provided by most mammalian systems. The baculovirus infects the host insect cells, replicates its genome through numerous cycles, and then produces large amounts of polyhedron crystals. The polyhedron gene can be replaced with a TM peptide gene. The polyhedron promoter will then make large amounts of analog protein following infection of the culture host cell and replication of the baculovirus genome. The non-secreted gene product is harvested from the host 3–7 days post infection. Alternatively, the TM peptide may be secreted from the cells if appropriate signal sequences are present on the protein. The host cells are competent or rendered competent for transfection by various means. There are several well-known methods of introducing DNA into animal cells. These include: calcium phosphate precipitation, DEAE-dextran technique, fusion of the recipient cells with bacterial protoplasts containing the DNA, treatment of the recipient cells with liposomes containing the DNA, electroporation, and microinjection of the DNA directly into the cells. See, Perbal, B. "*Practical Guide to Molecular Cloning,*" 2nd edition, John Wiley & Sons, New York and Wigler, et al., (1987) *Cell,* 16:777–785, which are each incorporated herein by reference.

E. Culturing Cells

It is preferred that the host cell is capable of rapid cell culture and able to appropriately glycosylate expressed gene products. Cells known to be suitable for dense growth in tissue culture are particularly desirable and a variety of invertebrate or vertebrate cells, both normal and transformed cell lines have been employed in the art. In particular, cells which are suitable hosts for recombinant TM expression and which produce or contain, under culturing conditions, a protease which results in the cleavage of native thrombomodulin now pose no problem in cleaving the mutated protease insensitive TM analog. Examples of such cells include CHO, CHL-1 (characterized as a human melanoma cell), Sf9 cells, etc., which are publicly available from the ATCC.

The transfected cells are grown up by means well known in the art. For examples, see Kuchler et al. (1977) *Biochemical Methods in Cell Culture and Virology.* The expression products are harvested from the cell medium in those systems where the protein is secreted from the host cell or from the cell suspension after disruption of the host cell system by, e.g., mechanical or enzymatic means, which are well known in the art.

F. Purification of TM Analogs

It is preferred that the TM peptides of this invention be secreted by cultured recombinant eukaryotic cells. The TM analogs are produced in serum-free or serum supplemented media and are secreted intact. If prokaryotic cells are used, the TM analogs may be deposited intracellularly. The peptides may be fully or partially glycosylated or non-glycosylated. Following the growth of the recombinant cells and concomitant secretion of TM analogs into the culture media, this "conditioned media" is harvested. The conditioned media is then clarified by centrifugation or filtration to remove cells and cell debris. The proteins contained in the clarified media are concentrated by adsorption to any suitable resin such as, for example, Q Sepharose or metal chelators, or by use of ammonium sulfate fractionation, polyethylene glycol precipitation, or by ultrafiltration. Other means known in the art may be equally suitable. Further purification of the TM analogs can be accomplished in the manner described in Galvin, J. B., et al., (1987) *J. Biol. Chem.,* 262:2199–2205 and Salem, H. H. et al., (1984) *J. Biol. Chem.,* 259:12246–12251 and in the manner described in the embodiment disclosed herein. The purification of TM analogs secreted by cultured cells may require the additional use of, for example, affinity chromatography, ion exchange chromatography, sizing chromatography, or other conventional protein purification techniques. See, e.g., Deutscher (ed.), "Guide to Protein Purification" in *Methods in Enzymology,* Vol. 182 (1990).

Recombinant TM analogs may be found in different forms which are distinguishable under nonreducing chromatographic conditions. Removal of those species having a low specific activity is desirable and is achieved by a variety of chromatographic techniques including anion exchange or size exclusion chromatography. Recombinant TM analogs may be concentrated by pressure dialysis and buffer exchanged directly into volatile buffers (e.g., N-ethylmorpholine (NEM), ammonium bicarbonate, ammonium acetate, and pyridine acetate). In addition, samples can be directly freeze-dried from such volatile buffers resulting in a stable protein powder devoid of salt and detergents. In addition, freeze-dried samples of recombinant analogs can be efficiently resolubilized before use in buffers compatible with infusion (e.g., phosphate buffered saline). Other suitable salts or buffers might include hydrochloride, hydrobromide, sulfate acetate, benzoate, malate, citrate, glycine, glutamate, and aspartate.

G. Oxidation Resistant TM analogs

Native thrombomodulin is susceptible to oxidation and when oxidized loses its ability to promote the activation of protein C. Many of the disease conditions requiring anticoagulation are also associated with high levels of toxic oxygen radicals, which can inactivate biomolecules and cause significant tissue damage. Examples of these conditions are reperfusion injury associated with myocardial infarction, DIC associated with septicemia, and alveolar fibrosis associated with adult respiratory distress syndrome. (See, Otani, H., et al., (1984) *Circ. Res.* 55:168–175, Saldeen, T., (1983) *Surg. Clin. N.A.* 63(2):285–304, and Idell, S., et al., (1989) *J. Clin. Inv.* 84:695–705.) In addition, any wound, such as occurring in surgical procedures, involves the influx of activated monocytes, polymorphonuclear leukocytes, etc., which can create toxic oxygen species as well as releasing a host of proteolytic enzymes, such as elastase. The connection between endothelial cell damage, inflammation, and thrombosis has long been recognized (see *The Molecular and Cellular Biology of Wound Repair,* ed. Clark, R. A. F. and P. M. Henson (1988), for example). Thrombomodulin is subject to inactivation by exposure to toxic oxygen species and this is expected to have a significant role in many pathogenic states.

Methods for rendering amino acids, specifically methionines, resistant to oxidation are well known in the art. It is possible to chemically modify thiol ether groups with iodoacetic acid, for example, to form oxidation resistant sulphonium groups (Gundlach, H. G., et al., (1959) *J. Biol. Chem.* 234:1754). A preferred method is by removing the susceptible amino acid or replacing it with one or more different amino acids that will not react with oxidants. The amino acids leucine, alanine, and glutamine would be particularly preferred amino acids because of their size and neutral character. Four methionines of soluble thrombomodulin may be subject to oxidation, particularly those located at residue 291 and 388. If only one methionine is to be blocked or eliminated, it is preferred that it be the residue at position 388.

Methods by which amino acids can be removed or replaced in the sequence of a protein are well known. See, e.g., Sambrook et al., supra; Ausubel et al., supra; U.S. Pat. Nos. 4,737,462; 4,588,585; EP-0285 123; and references cited therein. Genes that encode a peptide with an altered amino acid sequence can be made synthetically, for example. A preferred method is the use of site-directed in vitro mutagenesis. Site-directed mutagenesis involves the use of a synthetic oligodeoxyribonucleotide containing a desired nucleotide substitution, insertion, or deletion designed to specifically alter the nucleotide sequence of a single-strand target DNA. Hybridization of this oligonucleotide, also called a primer, to the single-strand template and subsequent primer extension produces a heteroduplex DNA which, when replicated in a transformed cell, will encode a protein sequence with the desired mutation.

To determine the resistance to loss of thrombomodulin activity due to oxidation, the test material (100–250 μg/ml) is first incubated with an oxidant such as, for example, chloramine-T, hydrogen peroxide at 5–10 mM chloramine-T, or 200–1000 mM hydrogen peroxide in a buffer of 0.2% N-ethylmorpholine and 0.008% Tween 80 at pH 7.0, for 20 minutes at room temperature. A buffer of PBS with 0.1% BSA may also be used. After such oxidant exposure, the test material is evaluated using one of the bioactivity assays, e.g., that described below specifically for the ability to act as a cofactor for the activation of protein C. Those mutant TM analogs that retain at least 60%, ordinarily 70%, more normally 80%, and preferably 90%, of activity they had prior to exposure to oxidants are considered to be oxidation resistant as compared to a wild-type (non-mutant) TM analog or native thrombomodulin.

H. Laboratory Assays for Measuring TM Activity

A number of laboratory assays for measuring TM activity are available. Protein C cofactor activity can be measured in the assay described by Salem, et al., (1984) *J. Biol. Chem.* 259(19):12246–12251 and Galvin, et al., (1987) *J. Biol. Chem.* 262(5):2199–2205. In brief, this assay consists of two steps. The first is the incubation of the test TM analog with thrombin and protein C under defined conditions (see Examples below). In the second step, the thrombin is inactivated with hirudin or antithrombin III and heparin, and the activity of the newly activated protein C is determined by the use of a chromogenic substrate, whereby the chromophore is released by the proteolytic activity of activated protein C. This assay is carried out with purified reagents.

Alternatively the effect of a TM analog can be measured using plasma in clotting time assays such as the activated partial thromboplastin time (APTT), thrombin clotting time (TCT), and/or prothrombin time (PT). The APTT assay is dependent on both the activating of protein C, as well as the direct inhibition of thrombin, while the TCT and PT assays are dependent only on the inhibition of thrombin. Prolongation of the clotting time in any one of these assays demonstrates that the molecule can inhibit coagulation in plasma.

The above assays are used to identify soluble TM analogs that are able to bind thrombin and to activate protein C in both purified systems and in a plasma milieu. Further assays are then used to evaluate other activities of native thrombomodulin such as inhibition of thrombin catalyzed formation of fibrin from fibrinogen (Jakubowski, et al., (1986) *J. Biol. Chem.* 261(8):3876–3882), inhibition of thrombin activation of Factor V (Esmon, et al., (1982) *J. Biol. Chem.* 257:7944–7947), accelerated inhibition of thrombin by antithrombin III and heparin cofactor II (Esmon, et al., (1983) *J. Biol. Chem.* 258:12238–12242), inhibition of thrombin activation of Factor XIII (Polgar, et al., (1987) *Thromb. Haemostas.* 58:140), inhibition of thrombin mediated inactivation of protein S (Thompson and Salem, (1986) *J. Clin. Inv.* 78(1):13–17) and inhibition of thrombin mediated platelet activation and aggregation (Esmon, et al., (1983) *J. Biol. Chem.* 258:12238–12242).

In the present invention, the TM analogs do not necessarily have all activities equal to that of native thrombomodulin. For example, if one compares an amount of a TM analog of the present invention with an equivalent amount of native chondroitin sulfonated membrane bound thrombomodulin (as measured in units of protein C cofactor activity, defined below) the TM analog will usually have at least a 20% reduction, and preferably a 50% reduction in its ability to inhibit thrombin-mediated conversion of fibrinogen to fibrin compared to the native thrombomodulin.

I. Methods for Altering the Glycosylation of TM Analogs

Carbohydrate substituents on proteins can affect both biological activity and circulating half-life. In order to make some TM analogs of the present invention, O-linked glycosaminoglycan carbohydrate such as is found in the native thrombomodulin protein, should be eliminated. There are numerous ways of accomplishing this objective. One method would be the treatment of the O-linked carbohydrate containing protein with a glyconalase known to specifically degrade sulfated glycosaminoglycans, such as chondroitinase ABC or hyaluronidase. This method is described in Bourin, M. et al., (1988) *J. Biol. Chem.* 263(17):8044–8052, which is herein incorporated by reference.

A second method for eliminating the O-linked carbohydrate is by introducing site directed mutations into the protein. The attachment of glycosaminoglycans is typically directed by a consensus recognition sequence of amino acids X-serine-glycine-X-glycine-X (Bourdon, M. A., et al., (1987) *Proc. Natl. Acad. Sci. U.S.A.* 84:3194–3198) where X is any amino acid. The recognition sequence for other types of O-linked sugars is generally threonine/serine-X-X-proline. The O-linked domain of natural thrombomodulin normally has at least one potential glycosaminoglycan addition site (aa 472) and/or 474 and four other potential O-linked carbohydrate addition sites (aa 464, 472, 474, 480 and 486), depending upon the cell type. Any change introduced into the nucleotide sequence that removes or changes the identity of any one or more of the amino acids in this recognition sequence might eliminate the potential O-linked carbohydrate attachment site. Methods of introducing site directed mutations into a nucleotide sequence are described above. For example, one or more of these serine or threonine residues may be modified to an unglycosylatable amino acid, e.g..

A preferred method of eliminating O-linked carbohydrate from a TM analog is by making an analog peptide that does not include the amino acids that are considered to be the O-linked domain, i.e., amino acids 468 through 485 of the native thrombomodulin gene sequence as shown in Table 1. Methods of accomplishing this are well known in the art and have been described above.

The circulating half-life of a protein can be altered by the amount and composition of carbohydrate attached to it. The TM analogs of the present invention contain both O-linked and N-linked carbohydrate. In addition to the potential O-glycosylation sites discussed above there are potential N-linked sites, e.g., at amino acids 29, 97, 98 364, 391, and 393, and potential O-linked sites, e.g., at amino acids 319, 393 and 396. Methods of altering carbohydrate composition in addition to those described above are: 1) expression of the TM analog gene in bacteria such *E. coli,* which does not have the cellular mechanisms necessary to glycosylate mammalian proteins, 2) expression of the TM analog gene in various eukaryotic cells, as each has its own characteristic enzymes that are responsible for the addition of characteristic sugar residues, and 3) treatment with chemicals such as hydrofluoric acid. Hydrofluoric acid, for example, chemically digests acidic and neutral sugars while leaving intact basic sugars such as N-acetyl glucosamines and, under certain conditions, galactosamines.

J. Protease resistant analogs

As noted above, when recombinantly produced TM is expressed in culture, especially in eukaryotic cells, e.g., CHO cells, the TMs contain substantial amounts of a two-chain version. This is detectable, e.g., by a binding property profile which indicates that there is a species with a different binding constant present, due to cleavage of the heterologous protein by an endopeptidase present under culturing conditions or during the purification process. This endopeptidase may be a constituent of, e.g., the host cell, a microbiological contaminant, the culture medium, etc. Analysis on SDS-PAGE under reducing conditions reveals that, when TM analogs are prepared in CHO cells and isolated from the conditioned media as disclosed herein, a protein band corresponding to a molecular weight of about 80 kD is present in addition to the 94 kD protein band which corresponds to single-chain soluble TM analog, as determined using rabbit polyclonal antibodies to insect cell 6EGF, e.g., $TM_E$(SF9) or stained gels. However, the same material expressed in CHL-1 cells apparently has less of this degraded material. This indicates that the extent of proteolytic activity may be cell line dependent.

A unique protease cleavage site in the human thrombomodulin extracellular domain has now been identified in various human analogs. In addition to the expected heterogeneity in the N-terminus (both FPAPAEP and APAEP N-termini are found) caused by signal sequence cleavage heterogeneity. These analogs contain a new sequence __IGTD__D____K, which is consistent with proteolysis of single-chain TM between $Arg^{456}$ and $His^{457}$. The amount of protein present in this cleaved form is as high as 50% of the TM chains.

This proteolytic cleavage site is formed in the last (c) loop of the sixth EGF domain, and thus the protein fragment is covalently held together by the last disulfide bond in the loop. This is further supported by the fact that the two bands are only seen on reducing gels. The 80 kDa band is the N-terminal fragment, based upon size and immunoreactivity. Therefore, TM analogs expressed in CHO cells, as well as in other cell lines which possess similar proteases that degrade the TM analog, are contaminated with cleaved two-chain material that exhibits similar molecular properties, e.g., molecular weight and amino acid sequence when assayed under the same conditions. Therefore, purification properties will often be similar, even though the TM analog is cleaved into a two-chain version, which is held together by disulfide bond(s).

As was noted, this cleavage site occurs in the c loop of the 6EGF domain of TM. Deletion of this loop in various constructs was shown to result in substantial loss in thrombin binding, evidenced by a large (~7-fold) increase in $K_d$, for thrombomodulin. Therefore, the contaminating two-chain material likely results in a similar loss of specific activity of such preparations. Furthermore, since other binding sites on the molecule are intact, the two-chain material should act as a competitive inhibitor of the single-chain TM analog. It is very difficult to separate two-chain material from the intact one-chain species, so it is important to produce highly homogeneous, intact single-chain TM which is not subject to proteolytic cleavage. This result has been accomplished through the construction of TM analogs, as disclosed herein, which remove and/or replace proteolytic cleavage sites and thus solve this heretofore unappreciated problem. The present invention allows for providing both full-length membrane-associated or soluble TM analogs which are resistant to cleavage by said protease(s).

Mutations can be routinely introduced into the TM analogs to modify the protease cleavage site in accordance with the procedures described herein. However, the c loop of 6EGF has been shown to be important in thrombin binding, and it is important that the binding properties of this area be maintained in the analog produced. The biological activity of the thus-obtained molecule would be maintained, or an increase in overall activity of a TM analog composition achieved, by preventing proteolysis. This will avoid loss of activity caused by change in the structure of the initial domain thought to be important in binding TM to thrombin. For example, since in rabbits, mice, and cows the 456–457 sequence of TM is Gly-Gln instead of Arg-His, as in the human TM, this modification is of particular interest. Other, similar, site specific mutations can be employed to routinely identify a modified sequence which is not subject to proteolysis, yet maintains the desired level of biological activity. For example, by homology to other similar EGF-like proteins, it can be seen that this region of the molecule is most likely to be in a β-sheet structure between reverse turns around $Pro^{450}/Asp^{451}$ and $Thr^{460}/Asp^{461}$. By this analysis, especially favorable substitutions would be those which incorporate amino acids found in high frequency in β-sheet structures, e.g., His, Val, Ile, Phe, Tyr, Trp, and Thr. Other favorable substitutions would be those which incorporate amino acids less likely to be found in β-sheet structures, e.g., Cys, Glu, Lys, Asp, Asn, and Pro. Certain other residues include, e.g., Cys, to prevent incorrect disulfide bonding with the other, structurally important, cysteines; Pro, which is less consistent with a β-sheet structure; and Lys and Arg, which may incorporate alternative, protease cleavage sites. Thus, one of ordinary skill in the art can easily and routinely determine the structure of TM analogs which will be resistant to protease cleavage, at this site or any other protease cleavage site. All such structures meeting the requirements described herein are included as part of this invention.

Of course, this modification can be employed in addition to one or more of the other modifications disclosed herein, e.g., for introducing oxidation resistance, increasing half-life of the analog in serum by removing glycosylation sites, homogeneous amino termini, homogeneous carboxy termini, etc., to provide a molecule having improved characteristics at several sites.

In addition to the previously described modifications, single-chain TM can be provided by removal of two-chain TM from preparations which contain it by routine protein purification methods.

K. Production of thrombomodulin analogs having a unique N-terminus

In addition to the above problem of preventing the production of TM polypeptide compositions exhibiting more than one N-terminus due to internal endoproteolytic cleavage, native thrombomodulin has an additional inherent heterogeneity at the normal N-terminus due to imprecise processing of the signal sequence. One characteristic of purity used in the definition of protein purity, e.g., in particular for regulatory approval for in vivo administration, is the detection of a single unique N-terminal sequence. It is commercially and otherwise advantageous to be able to produce a TM polypeptide composition having a unique N-terminal processing site, so as to avoid any potential ambiguity regarding the nature of the final product. Therefore, the nucleotide sequence encoding the N-terminal region of the polypeptide can be modified such that the processing enzyme(s) of the host cell will generate a single N-terminus of the mature polypeptide. This can be accomplished, e.g., by deleting the N-terminal three amino acids which constitute one of the processing sites, which results in a fully functional polypeptide that starts at amino acid 4 (Glu) of the native TM. This further provides a polypeptide having only a single and unique post-processing N-terminus. Other functional constructs can also be prepared routinely, having other single N-termini, either through further deletion of the native TM N-terminus or through substitution of alternative homogeneous N-terminal processing sites.

L. Production of thrombomodulin analogs having a unique C-terminus

A still further modification which can be made in accordance with the goals of this invention is to modify the TM analog composition so it exhibits a unique carboxy terminus. Providing single-chain material ensures elimination of at least one C-terminus in accordance with the procedures disclosed herein. One particularly advantageous construct provides a TM analog which is resistant to proteases or other factors, e.g., post-translational processing enzymes or C-terminal exoproteases, by providing a C-terminus which is resistant to degradation. These analogs are provided by modifying the DNA coding for the C-terminal amino acids of the polypeptide. For example, as disclosed herein, the C-terminus of the functional analog ending at amino acid 497 of native TM can conveniently be shortened by 7 amino acids to provide a C-terminus ending in a -Pro-Pro sequence which is particularly protease-resistant. Other amino acid deletions and substitutions which provide biologically active TM analogs can be prepared in accordance with routine modifications of the methods known in the art and as described herein.

M. Formulation and Use of Thrombomodulin Analogs

The soluble TM analogs described herein may be prepared in a lyophilized or liquid formulation. The material is to be provided in a concentration suitable for pharmaceutical use as either an injectable or intravenous preparation.

These compounds can be administered alone or as mixtures with other physiologically acceptable active materials, such as antibiotics, other anticoagulants, one-chain t-PA, or inactive materials, or with suitable carriers such as, for example, water or normal saline. The analogs can be administered parenterally, for example, by injection. Injection can be subcutaneous, intravenous or intramuscular. These compounds are administered in pharmaceutically effective amounts and often as pharmaceutically acceptable salts, such as acid addition salts. Such salts can include, e.g., hydrochloride, hydrobromide, phosphate, sulphate, acetate, benzoate, malate, citrate, glycine, glutamate, and aspartate, among others. See, e.g., *Remington's Pharmaceutical Sciences* (17th ed.), Mack Publishing Company, Easton, Pa., and Goodman & Gilman's, *The Pharmacological Basis of Therapeutics,* 8th ed., Pergamon Press, 1985, both of which are herein incorporated by reference. The analogs described herein may display enhanced in vivo activity by incorporation into micelles and/or phospholipid aggregates. Methods for incorporation into ionic detergent aggregates or phospholipid micelles are known.

An antithrombotic agent can be prepared using the soluble TM analogs described herein and can consist of a completely purified analog alone or in combination with a thrombolytic agent as described above. Compounds of the present invention which are shown to have the above recited physiological effects can find use in numerous therapeutic applications such as, for example, the inhibition of blood clot formation. Thus, these compounds can find use as therapeutic agents in the treatment of various circulatory disorders, such as, for example, coronary or pulmonary embolism, strokes, as well as the prevention of reocclusion following thrombolytic therapy, and these compounds have utility in the cessation of further enlargement of a clot during an infarction incident. Further, the compounds disclosed can be useful for treatment of systemic coagulation disorders such as disseminated intravascular coagulation (DIC), which is often associated with septicemia, certain cancers, and toxemia of pregnancy.

These compounds can be administered to mammals for veterinary use, such as with domestic animals, and for clinical use in humans in a manner similar to other therapeutic agents, that is, in a physiologically acceptable carrier. In general, the administration dosage for the TM analog will range from about at least 0.0002, more usually 0.02, and less than 5000, usually less than 2000, more usually less than 500 μg/kg, usually 0.02 to 2000 μg/kg and more usually 0.02 to 500 μg/kg of the host body weight. These dosages can be administered by constant infusion over an extended period of time, until a desired circulating level has been attained, or preferably as a bolus injection. Optimal dosages for a particular patient can routinely be determined by one of ordinary skill in the art.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents, and publications, cited above and below, are hereby incorporated by reference.

EXAMPLES

The first four examples which follow are directed primarily toward $TM_E$(Sf9). Similar methods are applicable with routine modifications to the $TM_{LEO}$ made in mammalian cells, as described in the later examples.

Example 1

Isolation and expression of TM analog sequences

A. Cloning

Genes for producing recombinant thrombomodulin analog peptides were isolated as described in copending applications U.S. Ser. No. 345,372, filed Apr. 28, 1989, U.S. Ser. No. 406,941, filed Sep. 13, 1989, and PCT Ser. No. 90/00955, filed Feb. 16, 1990, each herein incorporated by reference. Briefly, human DNA was used to isolate a gene encoding the 6 EGF-like domains of thrombomodulin corresponding to amino acids 227–462 as well as other portions of the thrombomodulin peptide. (See Table 1). This DNA was isolated from fetal liver according to the method of Blin, N and DW Stafford, (1976) *Nucleic Acids Res.* 3:2302. The DNA was then used as a template in a polymerase chain reaction with synthetically derived primers selected to embrace the desired regions (See Tables 3 & 4). See, e.g., Innis et al., *PCR Protocol,* A Guide to Methods and Applications (1990), Academic Press.

1. Isolation of genes encoding amino acids 227–462

The following steps provide a means to obtain a DNA insert encoding amino acids (aa) 227–462 and uses primers #1033 and #1034 (See Table 3). It is understood that by modifying the procedures set forth below by using alternative primers, other soluble TM analogs can be obtained.

The sequence of the #1033 and #1034 primers correspond to the 5' and 3' ends of the desired domain, but they have been modified so that they contain a BamHI site. A termination codon (TGA) was introduced following base 1586. The polymerase chain reaction was run under the conditions described by Saiki, et al., (1988) *Science* 320:1350–1354, except that the initial temperature of annealing was 37° C. After 10 cycles, the annealing temperature was raised to 45° C. for the remaining 30 cycles. An aliquot of the reaction products was separated on a 5% polyacrylamide gel and visualized by ethidium bromide staining. A band of the predicted size (700 bp) could clearly be seen. Alternatively one can sequence this band or hybridize it to an internal probe to confirm its identity.

2. Isolation of genes encoding other regions of thrombomodulin

The polymerase chain reaction as herein described was used in the same manner to isolate additional fragments of thrombomodulin corresponding to the regions listed in Table 4. In particular, these regions embrace one or more of the EGF-like domains and the O-linked glycosylation domain. The sequences of the primers selected to produce the desired regions are shown in Table 3.

3. Cloning plasmids containing the thrombomodulin analog genes

The remainder of the polymerase chain reaction mixture described above (i) was restricted with BamHI, separated on a 5% polyacrylamide gel, and the 700 bp band was excised and eluted. It was ligated to pUC19 that had been restricted with BamHI and the new plasmid was transformed into *E. coli* strain DH5-alpha. Recombinant colonies were selected on a medium containing ampicillin and 5-bromo-4-chloro-3-indolyl-β-D-galactoside. White colonies were picked onto a grid and hybridized by the Grunstein-Hogness technique with a synthetically derived gene corresponding to aa 283–352 of thrombomodulin that had been cut out of a cloning plasmid (pTM2.1) with EcoRI and HindIII before labelling with $^{32}P$ by random priming (Boehringer Mannheim).

After exposing the filters to X-ray film the one colony that hybridized to the pTM2.1 probe was selected and a culture grown up. DNA was extracted and analyzed by restriction with either BamHI or BglII to confirm the presence of an insert with the correct restriction map. The excised insert was also transferred to nitrocellulose and analyzed by hybridization with labelled pTM2.1. Both methods confirmed that the 700 bp insert contained the coding sequence for the 6 EGF-like domains of thrombomodulin. The insert was sequenced to verify that no mutations had been inadvertently introduced during the PCR procedure. The plasmid containing the desired gene fragment is named pUC19pcrTM7.

B. Expression of TM

1. Construction of AcNPV Transfer Vectors

The transfer vectors described below are also described in copending application U.S. Ser. No. 07/812,892, which is a continuation of U.S. Ser. No. 07/345,372. The transfer vectors contain the Hypodermin A signal sequence from *Hypoderma lineatum.* i. pHY1 and PSC716

Oligomers containing the Hypodermin A signal sequence, a translation initiation codon, a BglII cloning site, a BamHI 5' overhang and a Kpnl 3' overhang, COD#1198 and COD#1199 (see Table 2), were annealed and cloned into pSC654, a pUC19 derivative, creating pHY1. Plasmid pHY1 was restricted with BamHI and EcoRI, releasing the hypodermin A signal sequence. This sequence was then ligated to pSC714 to create the vector pSC716. Plasmid pSC714 is a derivative of pVL1393, obtained from Summers, et al. The only difference between the two is that in pSC714, one of the BglII sites has been destroyed.

ii. Construction of pHY101

The BamHI fragment from pUC19pCrTM7 (see Aiii above) was cloned into the BglII site of pHY1 and the orientation was chosen such that the hypodermin A signal sequence was adjacent to amino acid 227. This plasmid is pHY101.

iii. Construction of the AcNPV transfer vector pTMHY101

Plasmid pHY101 was treated with BamHI/EcoRI which releases the Hypodermin A signal sequence linked to the TM analog coding sequence. Shuttle vector pVL1393 contains a partially deleted AcNPV polyhedrin gene and unique BamHI and EcoRI cloning sites. The BamHI/EcoRI fragment from pHY101 was inserted downstream of the polyhedrin promoter, thus creating a plasmid, pTMHY101, in which the hybrid gene was under the control of the polyhedrin promoter.

iv. Construction of other AcNPV transfer vectors

Transfer plasmids containing other TM analog gene sequences were constructed using a strategy similar to that outlined above. Fragments from the cloning plasmids described above were cloned into pSC716 in frame so that the TM analog gene sequence was fused to the hypodermin A signal sequence. The TM gene sequences are listed in Table 4.

V. Production of pure phage stocks

Cell transfection was done using a calcium phosphate precipitation technique modified for insect cells according to Summers and Smith. Briefly, a T25 flask was seeded with $2\times10^6$ Sf9 cells, and the cells were allowed to attach for one hour at room temperature. Two $\mu$gs of transfer vector, for example, pTHR28, and 1 $\mu$g of AcNPV DNA were coprecipitated in calcium phosphate and incubated with the cells for 4 hours. The cells were rinsed and re-fed with growth media, then placed in a 28° C. incubator for 3–4 days. During this incubation, the cells produce both recombinant and non-recombinant virus which accumulate in the growth media. This media, containing a mixed viral stock, was assayed for the presence of protein C cofactor activity (see below).

Recombinant viruses were detected by plaque assay. The transfection stocks were diluted ($10^{-4}$, $10^{-5}$, and $10^{-6}$) and plated 4–7 days post-transfection. Occlusion negative (recombinant) plaques were picked 7 days after plating and replated ($10^{-1}$, $10^{-2}$, and $10^{-3}$ dilution). After another 7 days, the plates showed 100% pure occlusion-negative recombinant plaques. A single pfu from each was selected for production. A high titer viral stock was grown by infecting 5 mls of Sf9 cells ($1\times10^6$/ml in Excell 400 medium (JR Scientific)) with a single pfu, grown for 4–5 days. A portion of this stock was then diluted 1:50–1:100 into Sf9 cells grown to mid-log phase to produce a protein stock.

2. Production of Human TM Analogs in Mammalian Cells i. Mammalian expression vectors for TM analogs This example provides a mammalian expression vector comprising the analog genes of Example 1, A. Genes can be operably linked to the signal sequence of human tissue plasminogen activator (see Table 2). The expression plasmid, pPA124, contains a promoter contained within the three copies of the long terminal repeats derived from Harvey Sarcoma virus for the expression of cloned genes. This plasmid was derived from pPA119, and pSC672, both described in detail in co-pending U.S. Ser. No. 251,159, filed Sep. 29, 1988, incorporated herein by reference. A BglII-BclI fragment containing the SV40 polyadenylation region was isolated from pSC672. This fragment was cloned into pPA119 which had been digested with BglII and BclI. In the resulting plasmid, pPA124, both the BglII and BclI sites remained intact. Plasmid pPA124 contains the t-PA signal sequence adjacent to an appropriate restriction site and this signal sequence also contains the second intron of the human t-PA gene.

The gene encoding the soluble TM analog was removed from pUC19pcrTM7 by treatment with BamHI and ligated to pPA124 that had been treated with BglII. Transformants were screened for the presence of the insert in the correct orientation, that is, in which the t-PA signal sequence was linked to the 5' end of the thrombomodulin insert encoding an open reading frame. This plasmid, pTM101, was then digested with ClaI and ligated to a ClaI fragment containing the dhfr gene under the control of the SV40 promoter. The ClaI fragment is described in WO88/02411 at page 26. Transformants were screened for the presence of this dhfr cassette and then the orientation relative to the plasmid was determined by restriction mapping (pTM103).

Plasmid pTM103, containing the dhfr sequence in the divergent direction to the thrombomodulin sequence, was treated with BclI. A DNA fragment encoding a gene providing hygromycin resistance on a BamHI fragment was ligated into the plasmid. Clones were selected, after transformation into *E. coli* strain DH5α, by their ability to grow on plates containing both ampicillin and hygromycin B. The orientation of the hygromycin B gene relative to the plasmid was determined by restriction mapping. One plasmid, pTM108, in which the hygromycin B gene lies in the opposite orientation to the TM gene, was grown up in culture. This plasmid has the sequences encoding the TM analog under the control of the triple LTR promoter, with both a gene that confers hygromycin B resistance and one that encodes dhfr present on the plasmid. A similar expression plasmid, pTHR13, also contains the t-PA signal sequence operably linked to the sequence encoding the 6 EGF-like domains both under the control of the cytomegalovirus promoter. This plasmid contains the M13 origin of replication making it useful for site directed in vitro mutagenesis, described below. The thrombomodulin sequence was linked to the tissue plasminogen activator signal sequence, ensuring its secretion. The TM analog produced by both these plasmids, 4t/227–462, is comprised of the 6 EGF-like domains of thrombomodulin with an additional 4 amino acids on the N-terminal end that are the result of processing of the t-PA signal peptide.

ii. Transfection, selection and amplification of stable mammalian clones

For the transfection, 10 $\mu$g of pTM108 was mixed with Lipofectin reagent (Bethesda Research Laboratories) and added to a monolayer of $10^5$ CHL-1 host cells in 6-well plates. Forty-eight hours after transfection, a known number of cells were plated onto selective media. Resistance to hygromycin B was used as the selection marker. CHL-1 cells transfected with the bacterial hygromycin B gene can survive growth in 0.3 mg/ml hygromycin B.

The transfection or selection frequency was 2 in $10^3$ and was determined as the number of colonies arising after selection, divided by the total number of cells plated. The culture supernatant was shown to contain 1.5 U/ml TM activity after 24 hours in contact with the cells.

A population of cells resistant to the first selection conditions were then subjected to a second round of selective pressure. Either 100 nM or 500 nM methotrexate (MTX) was added to the growth medium to select for transfectants that expressed the dhfr gene. Only clones which had amplified the dhfr gene would be able to grow in this high level of MTX. In the process of gene amplification, other plasmid sequences will be co-amplified with the dhfr gene and thus lead to increased gene expression of the non-selectable gene as well. Resistant clones were apparent after 5 to 6 weeks. Individual clones resistant to these levels of MTX were isolated and assayed. A culture after selection in 100 nM MTX was shown to produce 4.9–14.7 U per ml of protein C activating activity (see below). A pooled population was plated into a ten-fold greater concentration of MTX (1 $\mu$M or 5 $\mu$M). Clones were again recovered from this selection step and assayed. At each step clones were shown to produce and secrete TM analog into the culture medium.

C. Site-directed Mutagenesis

The 6 EGF-like domains region of native thrombomodulin has two methionine residues, one at position 291 and one at position 388. (See Table 1). Site-directed in vitro mutagenesis was used to convert either or both of these methionines to other amino acids. Site-directed mutagenesis uses a synthetic DNA sequence containing a desired nucleotide substitution, insertion, or deletion to specifically alter the nucleotide sequence of a single-stranded template DNA. Hybridization of this synthetic DNA to the template and subsequent primer extension produces a heteroduplex DNA capable of cell transformation to yield the desired mutation. A diagram depicting this process is shown in FIG. 1 of U.S. patent application Ser. No. 07/568,456.

A similar method can be used to eliminate potential protease-sensitive regions, to modify glycosylation sites, and to modify the amino acid carboxy termini of the desired TM analog.

A plasmid for making single stranded DNA copies, pTHR14, was constructed by ligating the F1 origin of replication contained on an AseI-ScaI fragment into an insect cell transfer vector, pTMHY101, previously digested with NdeI and ScaI. Plasmid pTMHY101 contains a gene sequence that produces a peptide corresponding to the 6 EGF-like domains of thrombomodulin, amino acids 227–462, and is described above. pTMHY101 is described in copending application U.S. Ser. No. 345,372 as well as B(1)(iii) above. A similar vector containing the lectin domains, 6 EGF, and O-linked domains was used for mutagenizing and constructing the pTHR525, which encodes one preferred embodiment.

Specific mutagenizing oligonucleotide primers were synthesized and used with the MUTATOR™—DNA Polymerase III Site-directed Mutagenesis Kit (Catalogue #200500, Stratagene, La Jolla, Calif.), except as otherwise noted, to prime second strand synthesis and create thrombomodulin analog genes with either one or both of the methionines changed to a non-oxidizable amino acid. Primers directing conversion to the preferred amino acids leucine, glutamine, or alanine are shown in Table 5. Also included in these primers are substitutions in the nucleotide sequence that add a unique restriction enzyme site useful as a diagnostic for successful mutagenesis but which do not necessarily change the corresponding amino acid sequence. The nucleotide substitutions are underlined in the primers shown in Table 5. For example, in plasmid pTHR28 the methionine at position 388 in the native thrombomodulin protein was replaced with leucine, and in the process a unique PvuII site was introduced. It is understood that other substitute non-oxidizable amino acids would be equally useful in this embodiment of the present invention.

Purified single-stranded DNA templates were prepared using the procedure described by Bio-Rad (Muta-Gene Phagemid in vitro Mutagenesis, Instruction Manual, Cat. no. 170-3576, pages 33–34) although other procedures known in the art would be equally suitable.

The 5' terminus of each mutagenizing primer was phosphorylated by incubating 0.5 ng/$\mu$l of primer in a solution containing 2 mM rATP, 0.4 U/$\mu$l polynucleotide kinase in annealing buffer (20 mM Tris-HCl pH 7.5, 8 mM $MgCl_2$, and 40 mM NaCl) at 37° C. for 30 minutes. The reaction was heat inactivated by incubating the mixture at 65° C. for 15 minutes. Phosphorylation increases the rate of successful mutation. The phosphorylated primer was annealed to the single-stranded template by heating 100 ng of template and 2.5 ng of primer in 25 $\mu$l of annealing buffer to 65° C. for 5 minutes then allowing the mixture to cool and anneal at room temperature for 10 minutes. Double stranded DNA was made by primer extension essentially as described by Tsurushit, N., et al., (1988) *Gene* 62:135–139, and O'Donnell, M. E., et al., (1985) *J. Biol. Chem.* 260:12875–12883. Briefly, the template/primer mixture was diluted (1:1) with 10% annealing buffer plus 80 $\mu$g/ml bovine serum albumin, 2.5 mM dithiothreitol, 0.25 mM mixed dNTPs, 2 mM rATP and 1% glycerol plus 1 $\mu$g of single-stranded DNA binding protein. The reaction was incubated for 5 minutes at room temperature to allow the binding protein to coat the single-strand DNA template. DNA polymerase III holoenzyme (*E. coli,* 1.7 $\mu$l of 50 U solution) was added, and the reaction was incubated at 30° C. for 10 minutes. T4 DNA ligase was added (0.5 $\mu$l , 2 Weiss units) and the reaction was further incubated for 5 minutes at 30° C. This mixture was used to transform *E. coli* and properly mutated clones were selected by restriction digest pattern.

This same process can be used to make mutants that can be expressed in mammalian cells using, for example, pTR13 (described above) which has an M13 origin of replication for making single stranded DNA templates.

D. Production and purification of recombinant protein

T25 flasks were seeded at a density of $2\times10^6$ Sf9 cells in 5 ml TMN-FH media plus 10% FBS or Excell 400, then infected with an isolated recombinant plaque from Part B or C above. Viral stocks were collected after three days. Flasks (30–100 ml shaker flasks or 100–300 ml spinner flasks) were seeded with cells (1–$1.8\times10^6$/ml) and infected with aliquots of the viral stock equal to 1/50th to 1/100th of the final volume. The infected cell cultures were grown for four days before harvesting the conditioned media containing recombinant oxidation resistant TM analog protein.

The TM analogs were purified from conditioned media by removal of cell debris, followed by five chromatography steps: 1) Q Sepharose, 2) thrombin affinity, 3) gel filtration, 4) anion exchange, and 5) a second gel filtration step. The gel filtration steps effect an exchange of buffers. All chromatography steps were performed at 4° C.

1. Materials

Some of the chromatographic resins were purchased from commercial sources. Q Sepharose and Sephadex G25 were purchased from Sigma (St. Louis, Mo.), and Mono Q 5/® from Pharmacia LKB (Piscataway, N.J.).

DFP-thrombin agarose was prepared approximately as follows: 360 mg of bovine thrombin in 100 ml of 20 mM Na phosphate, pH 7.5 was added to approximately 100 ml of a 50% Affigel 10 resin slurry and mixed overnight at 4° C. The Affigel 10 was prepared for use as described by the manufacturer and equilibrated with the load buffer. Residual active esters were blocked by the addition of 100 ml of 0.1M glycine methylester (pH 5.6) for one hour at 4° C. The gel was then equilibrated with 30 mM Tris-HCl, 2M NaCl, pH 7.5, and 20 $\mu$l of DFP was added to give a final concentration of about 1 mM DFP. After 16 hrs of mixing at 4° C. an additional 6 $\mu$l of DFP was added and mixing continued for 4 additional hours. The resin was then washed with 20 mM Tris-HCl, 2 M NaCl pH 7.5 and stored at 4° C.

Thrombin activity was measured using the Kabi S-2238 substrate and indicated that >86% of the thrombin was removed from the solution, and presumably coupled to the resin, giving a final concentration of about 6 mg of thrombin per ml of resin. The enzymatic activity of the DFP treated resin was <1% of the starting activity.

2. Production of pure $TM_E$ analog peptide

Conditioned media was harvested and clarified by centrifugation at 1400×g for 10 minutes. The pH was adjusted from about 6.0 to about 5.2 with glacial acetic acid. The adjusted media was then loaded onto a column of Q Sepharose resin. The column had previously been equilibrated with about four column volumes of wash buffer 1 (117 mM Na acetate, 0.02% $NaN_3$ pH 5.0). After loading, the column was washed with wash buffer 1 followed by wash buffer 2 (25 mM Na acetate, 0.1 M NaCl pH 5.0) then the oxidation resistant TM analog was eluted with wash buffer 2 containing 0.3 M NaCl, pH 5.0.

Column fractions containing activity as measured in the protein C activation assay (see above) were pooled, then diluted with of 0.3 M NaCl, 20 mM Tris-HCl, 0.5 mM $CaCl_2$, 0.02% $NaN_3$, pH 7.5. The pH of the diluent was measured and adjusted to about 7.5 with NaOH. The ionic strength of the pool was about the ionic strength of a solution of 0.3 M NaCl. This adjusted pool was loaded overnight by gravity onto a thrombin agarose column pre-equilibrated with the same buffer used to dilute the conditioned media. The column was washed with diluent buffer, and the TM analog was removed from the matrix with 2.0 M NaCl, 20 mM Tris HCl, 1 mM NaEDTA, 0.02% $NaN_3$, pH 7.5.

The substantially pure TM analog was applied to a Sephadex G25 column and recovered in 0.2% N-ethylmorpholine acetate (NEM) pH 7.0. This step removes NaCl.

TM analog collected from the Sephadex G25 column was applied to a Mono Q column (Pharmacia, 10 micron particles, quaternary amine) pre-equilibrated with 0.2% N-ethylmorpholine (NEM) pH7.0. After washing with this buffer the various forms were separated using a gradient of 0 to 0.4 M NaCl. Samples of each fraction were evaluated on an SDS-PAGE gel under non-reducing conditions. SDS Polyacrylamide Gel Electrophoresis was performed by the method of Laemmli using 3.3% acrylamide in the stacking and 12.5% acrylamide in the running gel. Nonreduced samples were diluted in Laemmli sample solubilization buffer (50 mM Tris-HCl, pH 6.8, 25% glycerol, 2% SDS, and 0.01% bromophenol blue) and loaded directly onto the gel. Pharmacia LMW Calibration Kit protein standards were used for MW markers, and the gels were silver stained. In some fractions, only one major band is visible with silver staining.

Fractions containing peptides with like mobilities were pooled and then assayed for total protein content and for activity in the protein C activation assay as described below.

E. Assays for Thrombomodulin Analogs

1. Materials

Rabbit thrombomodulin, hirudin, and human Protein C were supplied by American Diagnostica. Human thrombin is available from a variety of noncommercial and commercial sources. Bovine thrombin for affinity chromatography was purchased from Miles Labs, Dallas, Tex. D-valyl-L-leucyl-L-arginine-p-nitroanilide (S-2266) and D-Phe-Pip-Arg-p-nitroanilide (S-2238) were purchased from Kabi Vitrum.

Bovine serum albumin (fraction V), citrated human plasma, and APTT reagent were purchased from Sigma Chemicals. Microtiter plates were supplied by Dynatech (#25861-96). All other reagents were of the highest grade available.

2. Methods and Results i. Protein C Activation Assay (Chromogenic)

This assay was performed by mixing 20 $\mu$l each of the following proteins in a microtiter plate: thrombomodulin sample (unknown or standard), thrombin (3 nM), and Protein C (1.5 $\mu$M). The assay diluent for each protein was 20 mM Tris-HCl, 0.1 M NaCl, 2.5 mM $CaCl_2$, 5 mg/ml BSA, pH 7.4. The wells were incubated for up to 2 hours at 37° C., after which Protein C activation was terminated by the addition of 20 $\mu$l of hirudin (0.16 unit/$\mu$l, 570 nM) in assay diluent and incubation for an additional 10 minutes.

The amount of activated Protein C formed was detected by adding 100 $\mu$l of 1.0 mM S-2266 (in assay diluent), and continuing to incubate the plate at 37° C. The absorbance at 405 nm in each well was read every 10 seconds for 15 minutes, using a Molecular Devices plate reader. The absorbance data was stored, and the change in absorbance per minute (slope) in each well was calculated. The change in absorbance per minute is proportional to pmole/ml of activated Protein C.

This ratio was determined empirically using varying concentrations of totally activated Protein C. Samples containing fully activated Protein C were generated by mixing Protein C at 0 to 1.5 $\mu$M with 60 nM rabbit TM and 30 nM thrombin, incubating for 0 to 4 hours, adding hirudin and measuring S2266 activity as above. Conditions under which fully of the Protein C was activated were defined as those in which the S2266 activity (A405/min) reached a plateau.

A unit of activity is defined as 1 pmole of activated Protein C generated per ml/min under the reagent conditions defined above. Alternatively, activity values are reported in comparison to native detergent solubilized rabbit thrombomodulin or another thrombomodulin standard.

ii. Protein C Cofactor Activity After Exposure to Oxidants

Chloramine-T (N-Chloro-p-toluenesulfonamide sodium salt, Sigma) was used to specifically test the resistance of the mutant TM analog peptides to oxidation. Transfection culture supernatant (1 ml) containing a peptide encoded by a mutant TM gene sequence or pTMHY101 (wild-type, aa 227–462) was desalted into 1.5 ml of 0.2% N-ethylmorpholine (NEM), pH 7.0, 0.008% Tween 80 on a NAP10 column (LKB/Pharmacia) and then lyophilized and resuspended in 100 $\mu$l of the above buffer. The sample was divided equally and either 5 $\mu$l of water (control) of 5 ul of 0.1 M chloramine-T (final conc.=9.1 mM) was added. The samples were incubated at room temperature for 20 minutes, then passed over the NAP-5 column to remove any oxidant. The desalting buffer used was protein C assay diluent. The mutant peptide retained all of its activity after being exposed to chloramine-T whereas the wild type peptide was substantially inactivated.

iii. Inhibition of the Activated Partial Thromboplastin Time (APTT)

The formation of a clot from citrated plasma is triggered by the addition of brain cephalin in ellagic acid ("APTT reagent"), and calcium ion. The time required for the clot to form is reproducible and increases proportionally with the addition of thrombomodulin. Reagents for the APTT are incubated at 37° C. before mixing, except for the citrated plasma, which is kept at 4° C.

The reaction was carried out as follows: 100 μl of Sigma Citrated Plasma was added to a plastic cuvette (Sarstedt #67.742), incubated at 37° C. for 1 min; 100 μl of Sigma APTT reagent was added and the mixture incubated for 2 min at 37° C.; 100 μl of test sample (or control buffer) and 100 μl of 25 mM $CaCl_2$ were added and the cuvette was immediately placed in a Hewlett-Packard 8451A spectrophotometer equipped with a Haake KT2 circulating water bath to keep the cuvette at 37° C. during reading. The absorbance due to light scattering at 320 nm was measured every 0.5 seconds, from 15 to 120 seconds, timed from the addition of $CaCl_2$. A plot of absorbance vs. time yields a sigmoidal curve, with the clotting time defined as the time at which the slope is the steepest, corresponding to the inflection point of the curve.

Ex vivo APTT assays were performed in the manner described above with the exception that citrated plasma from the animal used in the in vivo experiment was used in place of the citrated plasma obtained commercially.

Alternatively, an APC or TCT assay can be performed as described.

iv. Inhibition of thrombin clotting time (TCT) and prothrombin reaction (PT)

Both the PT and TCT are determined using the Hewlett-Packard 8452A diode-array spectrophotometer or an equivalent used for the APTT. For the PT reaction, 90 μl of either TM analog 6h/227–462 or PBS was added to 20 μl thromboplastin and 90 μl 25 mM $CaCl_2$ in a cuvette. The mixture was incubated for 1 minute at 37° C., then 100 μl of citrated plasma was added. After loading the cuvette into the spectrophotometer, the absorbance due to light scattering at 320 nm was measured every 0.5 seconds, from 15 to 120 seconds, timed from the addition of the plasma. A plot of absorbance vs. time yields a sigmoidal curve, with the clotting time defined as the time at which the slope is the steepest, corresponding to the inflection point of the curve. The TCT is evaluated in the same manner. The initial reaction mixture contains 100 μl citrated plasma, 25 μl of 100 mM $CaCl_2$, and 162.5 μl of either PBS or TM analog. After 1 minute, 12.5 μl of thrombin is added. The clotting time is measured as described above.

v. Direct anticoagulant activity—Inhibition of thrombin catalyzed conversion of fibrinogen to fibrin Thrombin and varying amounts of TM analog 6h/227–462 were incubated for 2 minutes at 37° C. in microtiter plate wells. The total initial reaction volume was 50 μl PBS plus 7.5 mM $CaCl_2$, and 90 nM thrombin. After initial incubation, 100 μl of 3.75 mg/mil human fibrinogen was added per well, and the thrombin induced formation of fibrin was followed by measuring the change in absorbance at 405 nm in a Molecular Devices Vmax spectrophotometer (Molecular Devices, Menlo Park, Calif.). The end-point of the assay was the time at which 50% of the final absorbance was reached. Residual thrombin activity was determined by reference to a thrombin standard curve, which linearly relates the reciprocal of the thrombin concentration to the clotting time. When amounts of detergent solubilized native rabbit thrombomodulin and TM analog 6h/227–462 exhibiting equal activity as measured by protein C cofactor activity are compared in the direct anticoagulant activity assay, the TM analog exhibits a significantly reduced ability to inhibit thrombin-mediated conversion of fibrinogen to fibrin (approximately 1/10).

vi. Inhibition of platelet activation and aggregation

The effects of TM analog 6h/227–462 on thrombin activation of platelets was tested by the methods of Esmon, et al., (1983) *J. Biol. Chem.* 258:12238–12242. When evaluated using this assay, TM analog 6h/227–462 did not significantly inhibit the thrombin-mediated activation and aggregation of platelets.

viii. Additional measures of TM antithrombotic activity

1) TM analog's inhibition of activation of Factor V by thrombin is measured by the method described by Esmon et al., *J. Biol. Chem.,* (1982), 257:7944–7947.

2) Inhibition of the TM analog thrombin complex by antithrombin III and heparin cofactor II is measured as described by Jakubowski et al. (1986), supra.

3) TM analog's inhibition of the inactivation of protein S by thrombin is measured by the method described by Thompson & Salem, *J. Clin. Invest.,* (1986), 78(1):13–17.

4) Inhibition of thrombin-mediated activation of Factor XIII is measured by the method of Polgar, et al., (1987) *Thromb. Haemostas.* 58:140.

Example 2

In vivo Activity of a TM Analog in a Rodent Model of Deep Venous Thrombosis

The ability of a TM analog to abrogate the formation of a thrombus was evaluated in a modified stasis/endothelial injury-induced venous thrombosis model in the rat (see Maggi, A. et al., (1987) *Haemostasis* 17:329–335 or Pescador, R. et al., (1989) *Thrombosis Research* 53:197–201). The vena cava of an anaesthetized male Sprague Dawley rat (450 gr) was surgically isolated, then the animal was treated by bolus injection into the femoral artery with a thrombomodulin analog (6h/227–462 which contains the 6 EGF-like domains of native thrombomodulin), standard heparin or normal saline (0.1 ml/rat), as a control. The dose of heparin was 45 units/rat. The dose of thrombomodulin analog was 100, 10, 1, 0.1 or 0.01 μg/rat. Two minutes post-injection, the inferior vena cava was ligated at the left renal vein to induce stasis, and the vascular endothelium was injured by gently pinching with forceps. After 10 minutes, the vena cava was excised and examined for the presence of a thrombus, which if present was removed and weighed. In all cases the animals treated with heparin or thrombomodulin analog (6h/227–462) at 100, 10, or 1 μg/rat showed no evidence of thrombus formation whereas the saline treated animals and those receiving the lowest dose of thrombomodulin analog (0.01 μg) had thrombi with an average weight of 14.9 mg/thrombus. The rats treated with 0.1 μg of thrombomodulin analog showed a trace amount of thrombus which was not large enough to be removed and weighed.

The dose range used in this study was selected based on an in vitro APTT assay in which 1 μg/ml of thrombomodulin analog was insufficient to prolong the APTT but the addition of 10 μg/ml resulted in a significant prolongation. The results of APTT assays done on plasma samples taken from each of the treated rats show no prolongation in the TM analog treated and control rats (100 μg TM analog=45 sec, all other doses TM analog and the saline controls=30–35 sec). However, the APTT in the heparin treated rats was significantly prolonged (100 sec.).

This experimental system is a directly comparable model for deep venous thrombosis in humans, which is characterized by vascular injury and reduced blood flow. The results described above demonstrate that very low doses of a TM analog that are able to act as a cofactor for thrombin-mediated activation of protein C yet have a substantially reduced ability to inhibit thrombin-mediated conversion of fibrinogen to fibrin are effective at preventing thrombus formation. Moreover, the absence of prolongation in the APTT measured ex vivo indicates that this TM analog has no systemic effect on coagulation parameters and, therefore, would not promote unsafe bleeding side effects.

Example 3

In vivo Activity of a TM Analog in a Primate Model of Both Venous and Arterial Thrombosis The antithrombotic properties of the thrombomodulin analogs were evaluated in an arteriovenous shunt model in the baboon using a slight modification of the method of Cadroy, Y. et al., (1989) *Journal of Laboratory and Clinical Medicine* 113:436–448, as described in Hanson S. R. and Harker, L. A. (1987) *Thrombosis and Haemostasis* 58:801–805. This model was chosen because of the hemostatic similarity between the baboon and man and because the arteriovenous shunt serves as a model for both arterial-type and venous-type thrombi.

A silastic tubing shunt, modified with a piece of dacron tubing (3.2 mm in diameter) followed by a teflon chamber (9.3 mm in diameter), was inserted into the femoral artery of the baboon such that blood flowed out of the artery through the shunt and returned to the baboon via the femoral vein (see FIG. 2 of U.S. patent application Ser. No. 07/568,456). The dacron tubing presents a thrombogenic surface which stimulates the natural coagulation process, and in particular the deposition of platelets on the graft surface, and serves as a model for the generation of arterial, i.e. platelet rich, thrombi held together by fibrin. The chamber creates a stasis condition similar to that found in veins, where the rate of flow of the blood is reduced, and in particular mimics the area around venous valves, thus modeling flow conditions similar to those resulting in deep venous thrombosis. The thrombi formed in the chambers are venous-type, fibrin rich thrombi. Venous-type thrombi also contain platelets, but fewer than arterial-type thrombi. Thrombus formation in either the dacron graft or chamber is evaluated by measuring both platelet deposition and fibrin accretion. Platelet deposition is measured by removing platelets from the baboon, radiolabeling the platelets with $^{111}$indium-oxine using the method of Cadroy, Y,. et al., (1989) *Journal of Clinical and Laboratory Medicine* 113(4):436–448, and then returning them to the animal. A scintillation camera, such as a Picker DC 4/11 Dyna scintillation camera (Picker Corp., Northford, Conn.), is positioned over the graft to directly measure the amount of radioactivity from the platelets being deposited as part of a thrombus as described in Cadroy, Y., et al., supra. As a second measure of thrombus formation, a 5 μCi dose of $^{125}$I-labeled baboon fibrinogen is given intravenously prior to insertion of the shunt. At the conclusion of the experiment, the shunt is removed, washed, and stored for 30 days to allow for the decay of $^{111}$indium radioactivity (half-life, 2.8 days). As $^{111}$indium decays much more rapidly than $^{125}$iodine, the detectable radioactivity remaining in the shunt represents the amount of fibrin deposited as part of a thrombus. Total fibrin deposition is calculated by dividing the counts per minute deposited by the amount of clottable fibrinogen present in the baboon blood as measured by the TCT assay. The first shunt in the series acts as a control for the second shunt.

Figure 3:
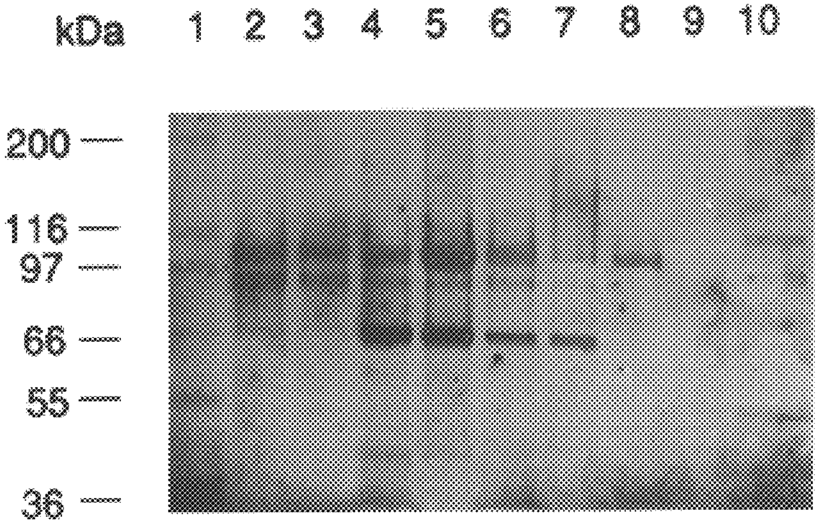
FIG. 3 shows gel electrophoresis profiles of samples run under reducing conditions.

Two shunts in series were inserted into a baboon and the TM analog (6h/227–462, see Table 4) infused at a point between the two shunts at a rate of 7 or 8 mg/hr for one hour. As can be seen in FIG. 3 of U.S. patent application Ser. No. 07/568,456, platelets were deposited in both the chamber and the dacron graft in the control shunt, however, platelet deposition was significantly reduced following infusion of the TM analog into the second shunt.

These experiments demonstrate that a TM analog that has the ability to act as a cofactor for thrombin-mediated protein C activation and has a significantly reduce ability to inhibit thrombin-mediated conversion of fibrinogen to fibrin and thrombin-mediated activation and aggregation of platelets can prevent the formation of either arterial-type or venous-type thrombi in an in vivo model. Such a TM analog would therefore be useful for pharmaceutical treatment of any thrombotic disease, whether localized to the arteries or to the veins.

Example 4

In Vivo circulating Half-life

The circulating half-life of several TM analogs was evaluated using a modification of the protocol of Bakhit, C., et al., (1988) *Fibrinolysis* 2:31–36. Thrombomodulin analog was radiolabeled with $^{125}$iodine according to the lactoperoxidase method of Spencer, S. A., et al., (1988) *J. Biol. Chem.* 263:7862–7867. Approximately 100,000 cpm amount of labeled analog was injected into the femoral vein of an anesthetized mouse and small samples collected at selected time intervals. The level of radioactivity present in each sample, corresponding to the amount of radiolabeled thrombomodulin analog present in the circulation, was determined by counting in a gamma counter (Beckman) and the time necessary to decrease the amount of radioactivity in the circulation to one-half of its original value determined. These can also be based upon an APC assay and ELISA determination Three thrombomodulin analogs were evaluated using this method: 6h/227–462 (see above), 6h/227–462 that had been pretreated with hydrofluoric acid (HF) to remove some or all of the carbohydrate, and 4t/227–462 (See Table 4 and Example 1.B.2). The treatment was done according to the method of Mort, A. J. and Lamport, T. A. (1977) *Analytical Biochemistry* 82:289–309. Briefly, 0.8 mg of TM analog (6h/227–462) was incubated in 1 ml anisole +10 mls HF (conc) at 0° C. for 1 hour under vacuum. After this time the volatile liquid was evaporated and the protein residue rinsed from the reaction chamber with two, 3 ml washes of 0.1 M acetic acid followed by two 3 ml washes of 50% acetic acid. The combined washes were extracted with 2 mls of ethyl-ether to remove any residual anisole. The peptide containing aqueous phase was desalted on a PD10 column with 92% of the protein recovered from the starting material.

As can be seen from the results in Table 6, treating the TM analog so as to modify glycosylation can significantly alter its circulating half-life. This can be accomplished by either removing carbohydrate or altering its composition by expression in different cell types.

TABLE 1

```
GGCACG GCGCAGCGGC AAGAAGTGTC TGGGCTGGGA CGGACAGGA        46

CGGACAGGAG AGGCTGTCGC CATCGGCGTC CTGTGCCCCT CTGCTCCGGC   96

ACGGCCCTGT CGCAGTGCCC GCGCTTTCCC CGGCGCCTGC ACGCGGCGCG  146

CCTGGGTAAC ATG CTT GGG GTC CTG GTC CTT GGC GCG CTG GCC  189
           Met Leu Gly Val Leu Val Leu Gly Ala Leu Ala
                       -15                 -10

CTG GCC GGC CTG GGG TTC CCC GCA CCC GCA GAG CCG CAG CCG  231
Leu Ala Gly Leu Gly Phe Pro Ala Pro Ala Glu Pro Gln Pro
        -5              -1   +1              5

GGT GGC AGC CAG TGC GTC GAG CAC GAC TGC TTC GCG CTC TAC  273
Gly Gly Ser Gln Cys Val Glu His Asp Cys Phe Ala Leu Tyr
         10                  15                  20

CCG GGC CCC GCG ACC TTC CTC AAT GCC AGT CAG ATC TGC GAC  315
Pro Gly Pro Ala Thr Phe Leu Asn Ala Ser Gln Ile Cys Asp
             25                  30                  35

GGA CTG CGG GGC CAC CTA ATG ACA GTG CGC TCC TCG GTG GCT  357
Gly Leu Arg Gly His Leu Met Thr Val Arg Ser Ser Val Ala
                 40                  45

GCC GAT GTC ATT TCC TTG CTA CTG AAC GGC GAC GGC GGC GTT  399
Ala Asp Val Ile Ser Leu Leu Leu Asn Gly Asp Gly Gly Val
 50                  55                  60

GGC CGC CGG CGC CTC TGG ATC GGC CTG CAG CTG CCA CCC GGC  441
Gly Arg Arg Arg Leu Trp Ile Gly Leu Gln Leu Pro Pro Gly
     65                  70                  75

TGC GGC GAC CCC AAG CGC CTC GGG CCC CTG CGC GGC TTC CAG  483
Cys Gly Asp Pro Lys Arg Leu Gly Pro Leu Arg Gly Phe Gln
         80                  85                  90

TGG GTT ACG GGA GAC AAC AAC ACC AGC TAT AGC AGG TGG GCA  525
Trp Val Thr Gly Asp Asn Asn Thr Ser Tyr Ser Arg Trp Ala
             95                 100                 105

CGG CTC GAC CTC AAT GGG GCT CCC CTC TGC GGC CCG TTG TGC  567
Arg Leu Asp Leu Asn Gly Ala Pro Leu Cys Gly Pro Leu Cys
                110                 115

GTC GCT GTC TCC GCT GCT GAG GCC ACT GTG CCC AGC GAG CCG  609
Val Ala Val Ser Ala Ala Glu Ala Thr Val Pro Ser Glu Pro
120                 125                 130

ATC TGG GAG GAG CAG CAG TGC GAA GTG AAG GCC GAT GGC TTC  651
Ile Trp Glu Glu Gln Gln Cys Glu Val Lys Ala Asp Gly Phe
    135                 140                 145

CTC TGC GAG TTC CAC TTC CCA GCC ACC TGC AGG CCA CTG GCT  693
Leu Cys Glu Phe His Phe Pro Ala Thr Cys Arg Pro Leu Ala
        150                 155                 160

GTG GAG CCC GGC GCC GCG GCT GCC GCC GTC TCG ATC ACC TAC  735
Val Glu Pro Gly Ala Ala Ala Ala Ala Val Ser Ile Thr Tyr
            165                 170                 175

GGC ACC CCG TTC GCG GCC CGC GGA GCG GAC TTC CAG GCG CTG  777
Gly Thr Pro Phe Ala Ala Arg Gly Ala Asp Phe Gln Ala Leu
                180                 185

CCG GTG GGC AGC TCC GCC GCG GTG GCT CCC CTC GGC TTA CAG  819
Pro Val Gly Ser Ser Ala Ala Val Ala Pro Leu Gly Leu Gln
190                 195                 200

CTA ATG TGC ACC GCG CCG CCC GGA GCG GTC CAG GGG CAC TGG  861
Leu Met Cys Thr Ala Pro Pro Gly Ala Val Gln Gly His Trp
    205                 210                 215

GCC AGG GAG GCG CCG GGC GCT TGG GAC TGC AGC GTG GAG AAC  903
Ala Arg Glu Ala Pro Gly Ala Trp Asp Cys Ser Val Glu Asn
        220                 225                 230
```

TABLE 1-continued

```
GGC GGC TGC GAG CAC GCG TGC AAT GCG ATC CCT GGG GCT CCC  945
Gly Gly Cys Glu His Ala Cys Asn Ala Ile Pro Gly Ala Pro
            235                 240                 245

CGC TGC CAG TGC CCA GCC GGC GCC GCC CTG CAG GCA GAC GGG  987
Arg Cys Gln Cys Pro Ala Gly Ala Ala Leu Gln Ala Asp Gly
                250                 255

CGC TCC TGC ACC GCA TCC GCG ACG CAG TCC TGC AAC GAC CTC 1029
Arg Ser Cys Thr Ala Ser Ala Thr Gln Ser Cys Asn Asp Leu
260                 265                 270

TGC GAG CAC TTC TGC GTT CCC AAC CCC GAC CAG CCG GGC TCC 1071
Cys Glu His Phe Cys Val Pro Asn Pro Asp Gln Pro Gly Ser
    275                 280                 285

TAC TCG TGC ATG TGC GAG A&C GGC TAC CGG CTG GCG GCC GAC 1113
Tyr Ser Cys Met Cys Glu Thr Gly Tyr Arg Leu Ala Ala Asp
        290                 295                 300

CAA CAC CGG TGC GAG GAC GTG GAT GAC TGC ATA CTG GAG CCC 1155
Gln His Arg Cys Glu Asp Val Asp Asp Cys Ile Leu Glu Pro
            305                 310                 315

AGT CCG TGT CCG CAG CGC TGT GAG GTC AAC ACA CAG GGT GGC 1197
Ser Pro Cys Pro Gln Arg Cys Val Asn Thr Gln Gly Gly Phe
                320                 325

TTC GAG TGC CAC TGC TAC CCT AAC TAC GAC CTG GTG GAC GGC 1239
Glu Cys His Cys Tyr Pro Asn Tyr Asp Leu Val Asp Gly Glu
330                 335                 340

TGT GTG GAG CCC GTG GAC CCG TGC TTC AGA GCC AAC TGC GAG 1281
Cys Val Glu Pro Val Asp Pro Cys Phe Arg Ala Asn Cys Glu
    345                 350                 355

TAC CAG TGC CAG CCC CTG AAC CAA ACT AGC TAC CTC TGC GTC 1323
Tyr Gln Cys Gln Pro Leu Asn Gln Thr Ser Tyr Leu Cys Val
        360                 365                 370

TGC GCC GAG GGC TTC GCG CCC ATT CCC CAC GAG CCG CAC AGG 1365
Cys Ala Glu Gly Phe Ala Pro Ile Pro His Glu Pro His Arg
            375                 380                 385

TGC CAG ATG TTT TGC AAC CAG ACT GCC TGT CCA GCC GAC TGC 1405
Cys Gln Met Phe Cys Asn Gln Thr Ala Cys Pro Ala Asp Cys
                390                 395

GAC CCC AAC ACC CAG GCT AGC TGT GAG TGC CCT GAA GGC TAC 1449
Asp Pro Asn Thr Gln Ala Ser Cys Glu Cys Pro Glu Gly Tyr
400                 405                 410

ATC CTG GAC GAC GGT TTC ATC TGC ACG GAC ATC GAC GAG TGC 1491
Ile Leu Asp Asp Gly Phe Ile Cys Thr Asp Ile Asp Glu Cys
    415                 420                 425

GAA AAC GGC GGC TTC TGC TCC GGG GTG TGC CAC AAC CTC CCC 1533
Glu Asn Gly Gly Phe Cys Ser Gly Val Cys His Asn Leu Pro
        430                 435                 440

GGT ACC TTC GAG TGC ATC TGC GGG CCC GAC TCG GCC CTT GCC 1575
Gly Thr Phe Glu Cys Ile Cys Gly Pro Asp Ser Ala Leu Ala
            445                 450                 455

CGC CAC ATT GGC ACC GAC TGT CCC GAC TCC GGC AAG GTG GAC 1617
Arg His Ile Gly Thr Asp Cys Asp Ser Gly Lys Val Asp Gly
                460                 465

GGT GGC GAC AGC GGC TCT GGC GAG CCC CCG CCC AGC CCG ACG 1659
Gly Asp Ser Gly Ser Gly Glu Pro Pro Pro Ser Pro Thr Pro
470                 475                 480

GGC TCC ACC TTG ACT CCT CCG GCC GTG GGG CTC GTG CAT TCG 1701
Gly Ser Thr Leu Thr Pro Pro Ala Val Gly Leu Val His Ser
    485                 490                 495

GGC TTG CTC ATA GGC ATC TCC ATC GCG AGC CTG TGC CTG GTG 1743
Gly Leu Leu Ile Gly Ile Ser Ile Ala Ser Leu Cys Leu Val
        500                 505                 510
```

TABLE 1-continued

```
GTG GCG CTT TTG GCG CTC CTC TGC CAC CTG CGC AAG AAG CAG 1785
Val Ala Leu Leu Ala Leu Leu Cys His Leu Arg Lys Lys Gln
            515                520                525

GGC GCC GCC AGG GCC AAG ATG GAG TAC AAG TGC GCG GCC CCT 1827
Gly Ala Ala Arg Ala Lys Met Glu Tyr Lys Cys Ala Ala Pro
                530                535

TCC AAG GAG GTA GTG CTG CAG CAC GTG CGG ACC GAG CGG ACG 1869
Ser Lys Glu Val Val Leu Gln His Val Arg Thr Glu Arg Thr
540                545                550

CCG CAG AGA CTC TGA GCGGCCTCCG TCCAGGAGCC               1904
Pro Gln Arg Leu OP
```

TABLE 2

```
t-PA Signal Sequence
ATG GAT GCA ATG AAG AGA GGG CTC TGC TGT GTG CTG CTG CTG
Met Asp Ala Met Lys Arg Gly Leu Cys Cys Val Leu Leu Leu
        -30                -25                -20

TGT GGA GCA GTC TTC GTT TCG CCC AGC CAG¦INTRON A¦GAA ATC
Cys Gly Ala Val Phe Val Ser Pro Ser Glu          Glu Ile
            -15                -10

CAT GCC CGA TTC AGA AGA GGA GCC AGA TCC
His Ala Arg Phe Arg Arg Gly Ala Arg Ser
    -5              -1  +1

Hypodermin A Signal Sequence - pHY1

COD #1198 GATCATG CTC AAG TTT GTT ATT TTA TTG TGC AGT ATT
            Met Leu Lys Phe Val Ile Leu Leu Cys Ser Ile
                           -15                -10

GCC TAT GTT TTC GGT GCC GTC GTA CCA AGA TCT CCC CGG
Ala Tyr Val Phe Gly Ala Val Val Pro Arg Ser Pro Arg
        -5              -1  +1
COD #1199
```

TABLE 3

```
COD #1292
5'ATCGGATCC TGC GAA AAC GGC GGC TCC primer/coding seqence
     BamHI  Cys Glu Asn Gly Gly Phe
         aa 427

COD #1293
5'GTGGGATCC TGC TTC AGA GCC AAC TGC primer/coding sequence
     BamHI  Cys Phe Arg Ala Asn Cys
         aa 350

COD #1294
5'CAGGGATCC TGC ACC CAG ACT GCC TGT primer/coding sequence
      BamHI Cys Asn Gln Thr Ala Cys
         aa 390
COD #1408
5'(CTG GTG GAC GGC GAG TGT) coding sequence
   GAC CAC CTG CCG CTC ACA CACCGCCGGC GCCT primer sequence
   Leu Val Asp Gly Glu Cys         NotI
   aa 339

COD #1409
5'(CGC CAC ATT GGC ACC GAC TGT) coding sequence
   GCG GTG TAA CCG TGG CTG ACA TCTCGCCGGC GTAG primer
 Arg His Ile Gly Thr Asp Cys      NotI       sequence
aa 456
```

TABLE 3-continued

```
COD #1410
5'(CAC GAG CCG CAC GGA CGT) coding sequence
   GTG CTC GGC GTG TCC ACG GTCTCGCCGG CGTT primer sequence
   His Glu Pro His Arg C            NotI
aa 381

COD #1411
5'(CGC CAC ATT GGC ACC GAC TGT TGA) coding sequence
   GCG GTG TAA CCG TGG CTG ACA ACT CGCCGGCGT primer
Arg His Ile Gly Thr Asp Cys STOP  NotI    sequence
aa 456

COD #1412
5'(GAC GAC GGT TTC ATC TGC) coding sequence
   CTG CTG CCA AAA GGA TAC GCGCGGCCGG CTG primer sequence
   Asp Asp Gly Phe Ile Cys          NotI
aa 416

COD #1433
5'(CTG GTG GAC GGC GAG TGT TGA) coding sequence
   GAC CAC CTG CCG CTC ACA ATC CGCCGGCGCC T primer
Leu Val Asp Gly Glu Cys STOP  NotI       sequence
aa 339

COD #1434
5'(CAC GAG CCG CAC GGA CGT TGA) coding sequence
   GTG CTC GGC GTG TCC ACG ATC CGCCGGCGTT primer sequence
   His Glu Pro His Arg Cys STOP     NotI
aa 381

COD #1435
5'(GAC GAC GGT TTC ATC TGC TGA) coding sequence
   CTG CTG CCA AAG GAT ACG ATC CGCCGGCGGCTG primer
   Asp Asp Gly Phe Ile Cys STOP  NotI       sequence
aa 416

COD #1480
5'(TGT GAC TCC GGC AAG GTG GAC TGA) coding sequence
   ACA CTG AGG CCG TTC CAC CTG ACT  CTTAAGCT primer
   Cys Asp Ser Gly Cys Val Asp STOP EcoRi    sequence
aa 462

COD #1479
5'(GGC ACC GAC TGT GAC TCC TGA) coding sequence
   CCG TGG CTG ACA CTG AGG ACT CTTAAGCAG
   Gly Thr Asp Cys Asp Ser STOP  EcoRI
aa 459

COD #1478
          His Trp Ala Arg Glu Ala Pro
5'CCATGGC CAC TGG GCC AGC GAG GCG CCG primer/coding
   BalI   His Trp Ala Arg Glu Ala Pro Sequence
       aa 216

COD #1481
5'(CCG GCC GTG GGG CTC GTG CAT TCG TGA) coding sequence
   GGC CGG CAC CCC GAG CAC GTA AGC ACT CGCCGGCGGT A primer
   Pro Ala Val Gly Leu Val His Ser STOP  NotI       seq.
aa 490
```

TABLE 4

| Vector | TM a.a. Region | Domain |
|---|---|---|
| | Expression in Insect Cells | |
| pTMHY101 | aa 221–462 | EGFs 1–6 |
| pTMHY102 | aa 216–468 | EGFs 1–6 |
| pTMHY103 | aa 216–464 | EGFs 1–6 |
| pTHR10 | aa 227–462 | EGFs 1–6 |
| pTHR11 | aa 227–462:227–462 | EGFS 1–6 + EGFS 1–6 |
| pTHR22 | aa 350–462 | EGFs 4, 5 & 6 |
| pTHR78 | aa 227–497 | EGFs 1–6 + O-linked glycosylation domain |
| pTHR13 | aa 227–462 | EGFs 1–6 |

TABLE 4-continued

| Vector | TM a.a. Region | Domain |
|---|---|---|
| | Expression in Mammalian Cells | |
| pTHR13 | aa 227–462 | EGFs 1–6 |
| pTHR19 | aa 350–462 | EGFs 4, 5 & 6 |
| pTHR20 | aa 227–462:227–462 | EGFs 1–6 + EGFs 1–6 |
| pTHR21 | aa 227–497 | EGFs 1–6 + O-linked glycosylation |
| domain | | |

TABLE 5

```
Primers for replacing the Methionine at aa 291

Native Sequence
 Pro Asp Gln Pro Gly Ser Tyr Ser Cys Met
CCCC GAC CAG CCG GGC TCC TAC TCG TGC ATG
CCCC GAC CAG CCG GGC TCC TAC AGC TGC CTG
Mutant Primer 1580                   Leu
       CAG CCG GGC TCC TAC TCG TGC CAG
Mutant Primer 1581                   Gln
CCCC GAC CAG CCG GGC TCC TAC TCG TGC GCA
Mutant Primer 1582                   Ala

Cys Glu Thr Gly Tyr Arg Leu Ala Ala
TGC GAG ACC GGC TAC CGG CTG GCG GCC G
TGC GAG ACC GGC TAC CGG CTG GCG GCC G

TGC GAG ACT GGC TAC CGG CTG GCG GCC G

TGC GAG ACC GGC TAC CGG CTG GCG GCC G

Primers for replacing the Methionine at aa 388

Native Sequence
Pro His Glu Pro His Arg Cys Gln Met
CCC CAC GAG CCG CAC AGG TGC CAG ATG
CCC CAC GAG CCG CAC AGG TGC CAG CTG
Mutant Primer 1573              Leu
CCC CAC GAG CCG CAC AGG TGT CAA CAG
Mutant Primer 1583              Gln
CCC CAC GAG CCG CAC AGG TGC CAG GCC
Mutant Primer 1584              Ala

Phe Cys Asn Gln Thr Ala Cys Pro Ala
TTT TGC AAC CAG ACT GCC TGT CCA GCC G
TTT TGC AAC CAG ACT GCC TGT CCA GCC G

TTT TGC AAC CAG ACT GCC TGT CCA GCC G

TTT TGC AAC CAG ACT GCC TGT CCA GCC G
```

TABLE 6

| Sample | Half-life (min) |
|---|---|
| 6h/227–462 | 2.7 |
| HF treated 6h/227–462 | 7.3 |
| 4t/227–462 | 8.1 |

Example 5

Expression of Recombinant Thrombomodulin Genes in CHO Cells

The cell line CHODXB11 was obtained from Larry Chasin of Columbia University. Cells were grown in HAM's F-12 complete medium (GIBCO), supplemented with 9% fetal bovine serum (FBS) and gentamicin.

A. Transfection

Cells, $1\times10^5$, were plated in a 100 mm petri dish one day before transfection. A plasmid pTHR525 encoding a soluble TM analog was prepared as described below in Example 9. The gene was constructed to encode an analog of thrombomodulin with the following modifications: δ3 (truncated 3 amino acids from the natural amino terminus), Met388Leu (replacement of Methionine at position number 388 with Leucine), Arg456Gly (replacement of Arginine at position 456 with Glycine), His457Gln (replacement of Histidine at position 457 with Glutamine), Ser5474Ala (replacement of Serine at position 474 with Alanine), and δ7 (truncated 7 amino acids from the carboxy terminus of a soluble TM at 497, i.e., the analog would end at amino acid 490). For each dish, the pTHR525 DNA to be transfected (20 μg dissolved in 100 μl of Opti-MEM (BRL), supplemented with mercaptoethanol (1:1000 dilution)) was mixed with a solution of Lipofectin (CalBiochem, 60 μg in 100 μl of Opti-MEM). The mixture was allowed to stand for 15 minutes at room temperature. Prior to the addition of the DNA mixture, the cells were washed twice with Opti-MEM and 3 ml of Opti-MEM was placed in each dish. The DNA and Lipofectin mixture was added to the plated cells and incubated overnight. The media was then changed to HAM's F-12 selective media (w/o glycine, hypoxanthine, and thymidine) and the cells allowed to recover overnight. The media was then changed to HAM's F-12 complete media with hygromycin (150 μg/ml, CalBiochem) and the cells maintained in this media for 3 days. At the end of this time, the media was changed to HAM's F-12 selective media (without glycine, hypoxanthine, and thymidine) supplemented with 9% dialyzed FBS and gentamicin. Clones were allowed to generate (approximately seven to ten days) and the mixed population was assayed by APC and ELISA assay. The cell population was expanded in culture flasks (225 $cm^2$) for production purposes.

B. Production: (1 L spinner culture×2)

The cultures were started with 3 g Cytodex 3 microcarrier beads (Pharmacia), 500 ml HAM's F-12 complete medium supplemented with 5% FBS, and $8.4\times10^7$ total cells. The following day, media was added to bring the volume to 1 L. The supernatant was harvested every other day for about 6 weeks. 450 ml was harvested the first two times and 1500 ml on all subsequent occasions. The total harvest was 11.35 L and contained $4.14\times10^6$ U.

Example 6

Purification of TM Analogs from Cultured Supernatants

A. Purification of $TM_{LEO}$(CHO)

Media containing the $TM_{LEO}$(CHO) analog with chondroitin or without sulfate expressed and secreted by CHO cells was made up to 0.01% Tween 80, filtered (1.2 μM Serum Capsule #12168 and 0.2 μM Culture Capsule #12140, Gelman Sciences, Ann Arbor, Mich.), loaded on a 100 ml Q-Sepharose column, washed with 50 mM Tris-HCl pH 7.8, 0.2 M NaCl, 0.1 mM EDTA, 0.01% Tween 80, and eluted with a NaCl gradient (0.2 to 2M) in the same buffer. Peak A (TM without chondroitin sulfate) and Peak B (with chondroitin sulfate) were diluted to 0.3 M NaCl, 20 mM Tris-HCl, 0.5 mM $CaCl_2$ EDTA, 0.02% $NaN_3$, pH 7.5. A thrombin affinity chromatography step is performed essentially as described above, and the samples desalted. Active fractions were pooled.

B. Purification of $TM_E$ (Sf9).

These products can be isolated as described above or as follows:

All procedures were performed at 4° C. Filtered insect cell harvest was diluted 1:1 with water, titrated with acetic acid to pH 5.2 and loaded on a Q-Sepharose fast flow resin (25 mM Na-acetate, pH 5, 0.1 M NaCl, 0.02% $NaN_3$). Active fractions were eluted with 0.3 M NaCl in the same buffer, pooled, diluted to 0.3 M NaCl, 20 mM Tris-HCl, 0.5 mM $CaCl_2$, 0.02% $NaN_3$, adjusted to pH 7.5 (NaOH), loaded on a 120 ml DFP-inactivated thrombin Affigel-10 resin (described above) and eluted with 2 M NaCl, 20 mM Tris-HCl, 1 mM $Na_2$EDTA, 0.02% $NaN_3$, pH 7.5. Active fractions were pooled, desalted and buffer exchanged on a Sephadex G-25 column into 0.2% NEM-Ac, pH 7, loaded on a Mono-Q HR10/10 column (Pharmacia), and gradient eluted between 0 and 1 M NaCl in the same buffer. High specific activity fractions (APC assay) were pooled, desalted on Sephadex G-25 into PBS or 0.2% NEM-Ac, pH 7, and stored frozen or lyophilized.

C. Soluble $TM_{LEO}$ Expression in CHL1 Cells

DNA coding for both the wild type and M388L mutant forms of TM, amino acids 1 to 497, and full length TM, amino acids 1 to 557, were expressed in Cos 7 and CHL1 cells using the mammalian expression vector pRc/CMV, obtained from Invitrogen, San Diego, Calif. For transient expression, Cos 7 cells expressing full length TM were harvested 48 to 72 h post transfection. CHL1 cells are a human melanoma cell line, available from the ATCC.

D. Purification of $TM_{LEO}$(CHL1)

Media containing the $TM_{LEO}$(CHL1) analog with chondroitin sulfate expressed and secreted by CHL1 cells was made 0.01% in Tween 80, filtered (1.2 μM Serum Capsule #12168 and 0.2 μM Culture Capsule #12140, Gelman Sciences, Ann Arbor, Mich.), loaded on a 100 ml Q-Sepharose column, washed with 50 mM Tris-HCl pH 7.8, 0.2M NaCl, 0.1 mM EDTA, 0.01% Tween 80, and eluted with a NaCl gradient (0.2 to 2 M) in the same buffer (elutes near 1 M NaCl by APC assay). The eluent was diluted 3-fold with $H_2O$, loaded on a second 5 ml Q-Sepharose column, washed with the same buffer except with 0.001% Tween 80 and 0.7 M NaCl and eluted with a second shallow gradient (30 column volumes; 0.7 to 1.6 M NaCl). Small amounts (<500 μg) were further purified by molecular exclusion chromatography on Superose 6 (Pharmacia) in PBS.

Example 7

Demonstration of the Presence of Two-Chain TM

E. Anion Exchange Chromatography

As noted above, more than one form of $TM_E$ analog is detected in thrombin-affinity purified material from Sf9 cells run on a SDS-PAGE gel under non-reducing conditions. A method was developed to resolve these variants. $TM_E$ (Sf9) analog 6h/227-462, $TM_E$ (Sf9) collected from the Sephadex G25 column, as described above, was applied to a Mono Q column (Pharmacia, 10 micron particles, quaternary amine) pre-equilibrated with 0.2% N-ethylmorpholine (NEM) pH 7.0. After washing with this buffer the various forms were separated using a gradient of 0 to 0.4 M NaCl. The elution and activity profiles are shown in FIG. 1. Samples of each fraction were evaluated on an SDS-PAGE gel under non-reducing conditions. Three distinct bands with slightly different mobilities could be seen on the stained gel. Fractions containing peptides with like mobilities were pooled (A=fractions 32–35, B=fractions 40–44, C=fractions 70–71) and then assayed for total protein content and for activity in the Protein C activation assay. The specific activities are listed in the table below. No inactive peptides were detectable in any of the fractions.

| Test Material | Specific Activity (U/mg) |
|---|---|
| Mono Q Load | 166,000 ± 12,000 |
| fractions 32–35 (A) | 416,000 ± 19,000 |
| fractions 40–44 (B) | 262,000 ± 4,000 |
| fractions 70–71 (C) | 67,600 ± 5,000 |

F. SDS-PAGE Analysis

Every fraction or every other fraction of $TM_E$(Sf9) purified on the Mono-Q column was analyzed by SDS-PAGE as follows: 4.5 μl of a fraction was mixed with 1.5 μl of 4×concentrated SDS-PAGE sample buffer without reducing agents, heated about 10 to 15 min. at about 90° C. and loaded onto a 8–25% acrylanide Phast gel from Pharmacia using the comb and protocol provided. The gel was run on the Phast gel system using the protocol suggested by the manufacturer. The gel shows fractions across the peak and shoulder which were pooled to make Pool and B, respectively (FIG. 2). The abbreviations are as follows:

Numbers—Fraction numbers referred to in FIG. 1 and above Table listing specific activities.

A—occasionally seen artifact band in load on Panel A, frac. 28 and frac. 39; this appears to be from protein from fingerprints on labware.

D—$TM_E$ disulfide linked dimer which elutes in Pool C.

MU—upper monomer, this appears to be the single-chain $TM_E$.

ML—lower monomer, has the same N-terminus as MU (AlaValValPro . . . ), but has a faster electrophoretic mobility as could be expected of a protein proteolyzed near the C-terminus L—material loaded on the Mono-Q column containing D, MU and ML.

By pooling the fractions indicated in the above table, MU or ML can be greatly enriched, as desired.

Example 7

Demonstration of the Presence of Two-Chain TM

A. Separation of Cleaved Forms from CHL1 and CHO Cells

The following samples were analyzed on an 8% Tris-Glycine gel from Gel Novex, all samples were run under reducing conditions. FIG. 3 shows the results for the following samples:

| Lane | |
|---|---|
| 1 | Novex Wide Range Marker |
| 2 | $TM_{LEO}$ (CHO) #82891 LJ |
| 3 | $TM_{LEO}$ (CHO) PkB + Chondroitinase ABC (*P. vulgaris*) |
| 4 | $TM_{LEO}$ (CHO) PkB + Chondroitinase AC (*Flavobacterium heparium*) |
| 5 | $TM_{LEO}$ (CHL1) PkB + Chondroitinase AC (*Flavobacterium heparium*) |
| 6 | $TM_{LEO}$ (CHO) PkB + Chondroitinase AC (*Anthrobackter aurescens*) |
| 7 | $TM_{LEO}$ (CHL1) PkB + Chondroitinase AC (*Flavobacterium heparium*) |
| 8 | $TM_{LEO}$ (CHL1) PkB + Chondroitinase ABC (*P. vulgaris*) |
| 9 | $TM_{LEO}$ (CHL1) PkB #Q617 |
| 10 | Novex Wide Range Markers |

This gel was originally run to test commercial chondroitinases from various sources. It shows that samples from CHO cells and CHL1 cells both contain the 80 kDa band which appears to be the truncated form of the full length soluble TM analogs. The band at 66 kDa is BSA which is added to the commercial chondroitinase preparations for stability. Lane 9 is underloaded.

B. Western Blot

Samples of purified TM and TM analogs were analyzed on an 8% Tris-Glycine gel, which was run at 125 volts for 2 hours. The proteins were electroblot-transferred to nitrocellulose for 3 hours at 120 MA. The nitrocellulose was then incubated overnight with 3% BSA at 4° C. The blot was then exposed to a first mouse polyclonal antibody preparation which were raised against the reduced and denatured 6EGF region of TM, at a 1:500 dilution for 30 minutes. Then, a second antibody, a commercial biotinylated Goat was added for 30 minutes. The resulting nitrocellulose blot was then developed with avidin-HRP conjugate and 4-Chloro-T-Naphthol, from a commercial supplier.

Figure 4:
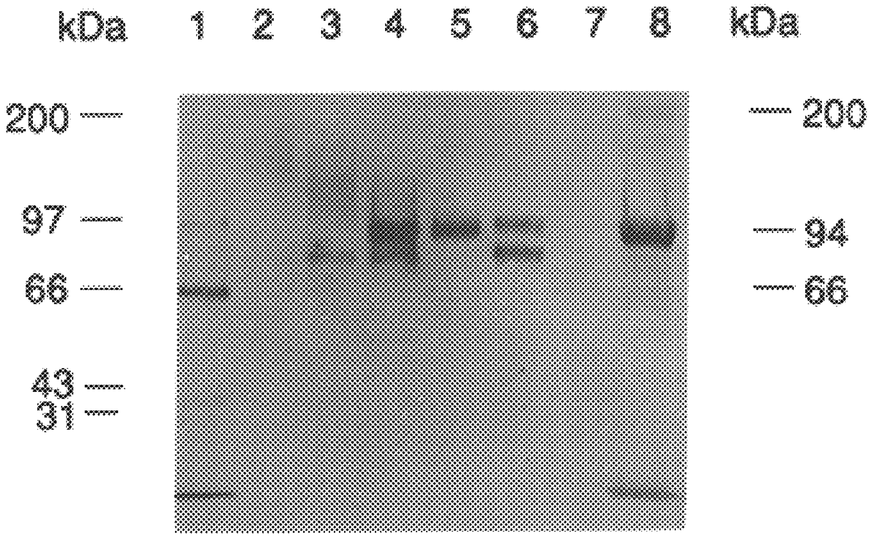
FIG. 4 shows a Western blot of a gel electrophoresis profile.

FIG. 4 shows a Western blot gel in which:

| Lane | |
|---|---|
| 1 | 10 μl BRL Biotinylated markers |
| 2 | $TM_{LEO}$ (CHL1) PkB #QG17 (~1250 APC Units) |
| 3 | $TM_{LEO}$ (CHO) PkB #82891 LJ (~130 APC Units) |
| 4 | $TM_{LEO}$ (CHO) PkA #82891 LJ (~125 APC Units) |
| 5 | $TM_{LEO}$ (CHL1) PkB + Chondroitinase ABC #QG21 (~106 APC Units) |
| 6 | $TM_{LEO}$ (CHO) PkB + Chondroitinase ABC #QG39 (~34 APC Units) |
| 7 | $TM_{LE}$ (CHL1) PkB + Chondroitinase ABC #QG41 (~100 APC Units) |
| 8 | 5 μl "Rainbow" markers, Amersham |

| MW Markers for FIG. 4; | BRL Biotinylated | "Rainbow" | |
|---|---|---|---|
| | 97.4 kDa | 200 kDa | |
| | 66.2 | 97.4 | |
| | 42.7 | 69.0 | |
| | 31.0 | 46.0 | |
| Run with Dye Front | 21.5 | 30.0 | |
| Run with Dye Front | 14.4 | 21.5 | Run w/Dye Front |
| | | 14.3 | Run w/Dye Front |

This Western analysis shows that all samples of $TM_{LEO}$ expressed in CHO cells have an immunoreactive band at 80 kDa which appears to be the cleaved form and that some sample of $TM_{LEO}$ expressed in CHL1 cells have the 80 kDa band (Lane 2). Lane 7 containing the "lectin-6EGF" analog, $TM_{LE}$ is underloaded.

C. $K_d$ Determination

The $K_d$ was determined for isolated preparations of recombinant thrombomodulin. $TM_{LEO}$(CHO) was prepared as described earlier. Determinations were made in 96 well plates in an assay diluent (20 mM Tris-HCl, pH 7.5, 0.1 M NaCl, 0.1% $NaN_3$, 0.5% BSA, containing either 0.25 or 2.5 mM $CaCl_2$) For the $K_d$ determination, thrombin (1 nM) was added to the TM analog (0.5 to 250 nM); reaction was initiated by Protein C addition (3 μM). All concentrations listed are final concentrations. Mixtures were incubated 10–60 minutes (75 μl, 20° C.) and quenched with hirudin (570 nM). 100 μl/well of S-2266 substrate (Kabi Vitrum), in modified assay diluent, was then added (2 mM).

Figure 5:
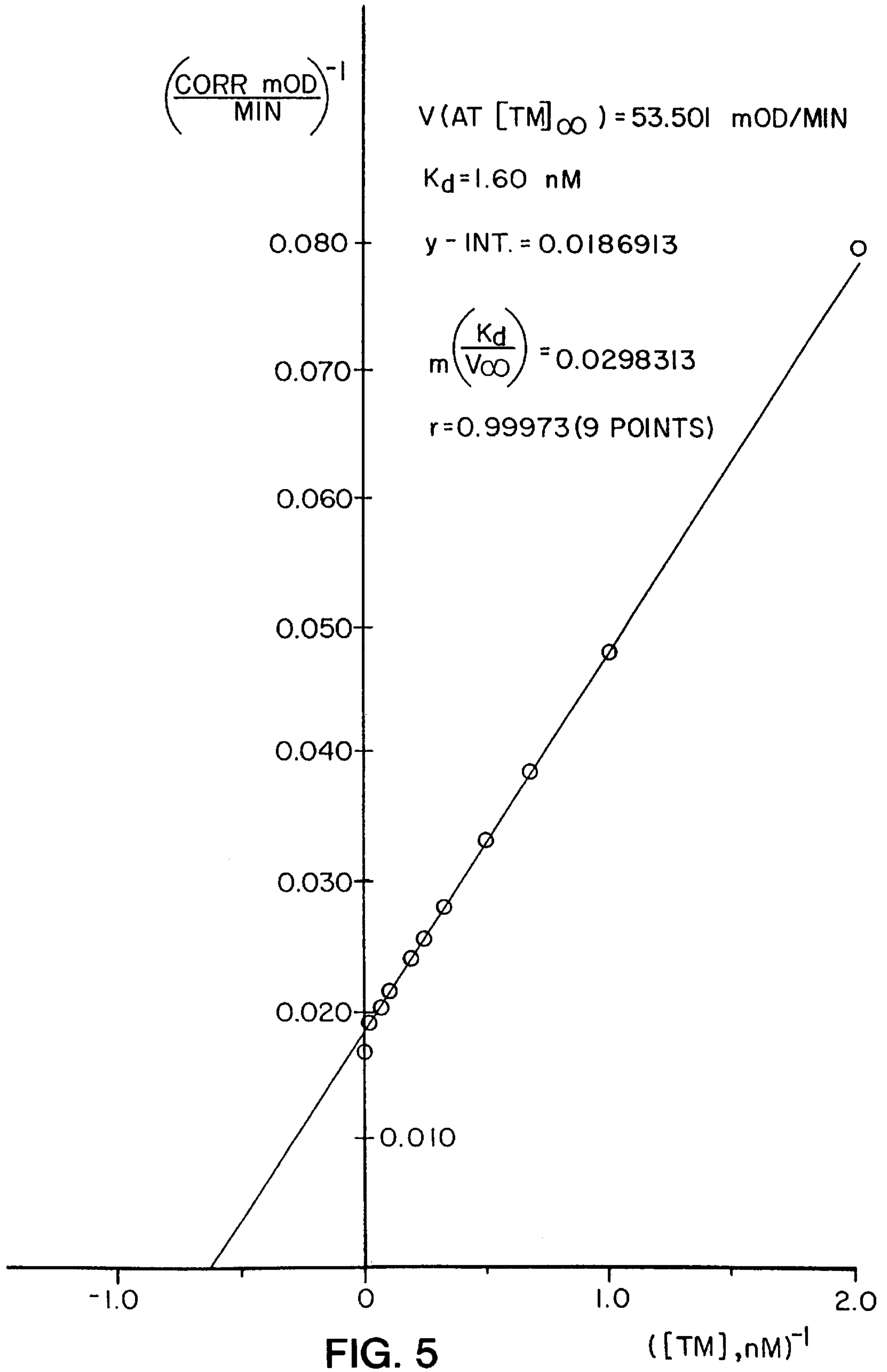
FIG. 5 shows a double reciprocal plot of TM binding to thrombin.

As can be seen from the double reciprocal plot in FIG. 5, the actual first point, corresponding to high TM concentration, is displaced from the linear projection derived from the measurements at lower TM concentrations. This indicates that another TM component with a significantly high $K_d$ is present in the test sample. It appears that there are two classes of thrombin binding species in the sample, both of which lead to the formation of an active complex. The low affinity form is likely to correspond to the cleaved or truncated, e.g. form, a TM analog which does not bind thrombin as tightly as uncleaved TM.

Example 8

Sequencing Data Demonstrating Two Different Amino Termini

A. N-terminal Sequence Analysis

The purified protein was dried and sequenced (Applied Biosystems, Model #477 with a 900A data module or Model #470A with chart recorder). PTH-amino acids were identified on a 120A Applied Biosystems PTH Analyzer by RP-HPLC (Brownlee PTH-C18 cartridge, 2.1×222 mm).

B. N-terminal Analysis

Various preparation of TM analogs were analyzed as above. As can be seen in Table 7, the samples from $TM_{LEO}$ (CHO) peak A contain heterogeneous N-termini. For example, N-terminal analysis of 3 samples shown in Table 7 of TM produced by a plasmid containing the unmodified sequence expressed in CHO cells showed a strong cleavage site sequence amounting to 5 to 19% (11+4%) of the protein present.

In contrast, N-terminal analysis of at least 100 picomole of DXB-11 525, a TM preparation isolated from CHO cells transformed with the pTHR525 plasmid containing the TM mutations at the indicated positions (63,M388L,R456G,H457Q,S474A,67) confirmed that this polypeptide contained essentially no N-terminal heterogeneity (maximum second sequence is 0.6±1.350≅0%). In particular, thus indicating absence of detectable protease cleavage at that, or any other, site. :HIGT was not seen.

TABLE 7

Sequence Comparison of Samples of $TM_{LEO}$(CHO)PkA with $TM_{LEO}$(CHO)∂3, M388L, R456G, H457Q, S474A, ∂7

Notes:
1) Data is pmol of amino acid per cycle and percent clipped calculated per cycle.
2) Amino acids which are difficult to quantitate reliably: His, Arg, Ser, Thr
3) Cys not quantitated since samples not reduced and alkylated.
4) Pro often not well cleaved, therefore yield may be low.
5) Pmol data corrected for background signal and "lag" signal from previous cycles.

| Cycle | N-term #1 | | N-term #2 | | Sum | Clip | | % |
|---|---|---|---|---|---|---|---|---|
| A) Sample: $TM_{LEO}$(CHO)PkA 82891; 10/23/91 | | | | | | | | |
| 1 | Ala | 110 | Phe | 57 | 167 | His | 0.6 | |
| 2 | Pro | — | Pro | — | 115 | Ile | 11 | 9.5% |
| 3 | Ala | — | Ala | — | 127 | Gly | 24 | 18.9% |
| 4 | Glu | 30 | Pro | 49 | 79 | Thr | 10 | 12.6% |
| 5 | Pro | 72 | Ala | 71 | 143 | Asp | 7.1 | 5.0% |
| 6 | Gln | 41 | Glu | 26 | 67 | Cys | — | |
| 7 | Pro | — | Pro | — | 86 | Asp | 8.5 | 9.9% |
| B) Sample: $TM_{LEO}$(CHO)PkA 91991; 10/28/91 | | | | | | | | |
| 1 | Ala | 221 | Phe | 108 | 329 | His | 8 | |
| 2 | Pro | — | Pro | — | 228 | Ile | 13 | 5.7% |
| 3 | Ala | — | Ala | — | 321 | Gly | 37 | 11.5% |
| 4 | Glu | 128 | Pro | 114 | 242 | Thr | 7 | |
| 5 | Pro | 182 | Ala | 125 | 307 | Asp | 40 | 13% |
| 6 | Gln | 147 | Glu | 114 | 67 | Cys | — | |
| 7 | Pro | — | Pro | — | 328 | Asp | 126 | |

TABLE 7-continued

Sequence Comparison of Samples of $TM_{LEO}$(CHO)PkA with $TM_{LEO}$(CHO)∂3, M388L, R456G, H457Q, S474A, ∂7

Notes:
1) Data is pmol of amino acid per cycle and percent clipped calculated per cycle.
2) Amino acids which are difficult to quantitate reliably: His, Arg, Ser, Thr
3) Cys not quantitated since samples not reduced and alkylated.
4) Pro often not well cleaved, therefore yield may be low.
5) Pmol data corrected for background signal and "lag" signal from previous cycles.

C) Sample: $TM_{LEO}$(CHO)PkA 102491-A; 1/17/92

| | | | | | | | | | |
|---|---|---|---|---|---|---|---|---|---|
| 1 | Ala | 142 | Phe | 60 | 202 | His | 0 | 0% |
| 2 | Pro | — | Pro | — | 118 | Ile | 20 | 17% |
| 3 | Ala | — | Ala | — | 160 | Gly | 20 | 12.5% |
| 4 | Glu | 48 | Pro | 38 | 86 | Thr | 8 | 9.3% |
| 5 | Pro | 48 | Ala | 60 | 108 | Asp | 41 | |
| 6 | Gln | 52 | Glu | 39 | 91 | Cys | — | |
| 7 | Pro | — | Pro | — | 58 | Asp | 42 | |

D) Sample: $TM_{LEO}$(CHO)∂3, M388L, R456G, H457Q, S474A27, pTHR525

| Cycle | N-term | | Clip | | % |
|---|---|---|---|---|---|
| 1 | Glu | 88 | Gln | 0 | 0% |
| 2 | Pro | 184 | Ile | 0.4 | 0.2% |
| 3 | Gln | 171 | Gly | 6 | 3.5% |
| 4 | Pro | 172 | Thr | 0 | 0% |
| 5 | Gly | 149 | Asp | 0 | 0% |
| 6 | Gly | 143 | Cys | — | |
| 7 | Ser | 28 | Asp | 0 | 0% |

Example 9

Method of Mutagenesis and Oligonucleotide selection for Production of Protease-Resistant TM Analogs The plasmid pTHR525, coding for a preferred embodiment of a protease-resistant TM, was constructed by mutagenesis of the TM gene (see U.S. patent application Ser. No. 07/345,372, GenBank®, or the sequence of pTHR324 shown in Table 8; pTHR324 contains the TM gene in the pRC/CMV vector). A gene construct which, upon expression, expresses a polypeptide corresponding to amino acids 3–490 was made by standard mutagenesis techniques.

TABLE 8

```
GCGGCCGC

tcgagcatgcatctagagggccctatt

ctatagtgtcacctaaatgctcgctgatcagcctcgactgtgccttctagttgccagccatctgttgtttgcccctcccc

cgtgccttccttgaccctgg

aaggtgccactcccactgtcctttcctaataaaatgaggaaattgcatcgcattgtctgagtaggtgtcattctattctg

gggggtggggtggggcagga

cagcaagggggaggattgggaagacaatagcaggcatgctggggatgcggtgggctctatggaaccagctggggctcgag

ggggatccccacgcgccct

gtagcggcgcattaagcgcggcgggtgtggtggttacgcgcagcgtgaccgctacacttgccagcgccctagcgcccgct

cctttcgctttcttcccttc

ctttctcgccacgttcgccggctttccccgtcaagctctaaatcggggcatccctttagggttccgatttagtgctttac

ggcacctcgaccccaaaaaa

cttgattagggtgatggttcacgtagtgggccatcgccctgatagacggtttttcgccctttactgagcactctttaatag

tggactcttgttccaaactg

gaacaacactcaaccctatctcggtctattcttttgatttataagatttccatcgccatgtaaaagtgttacaattagca

ttaaattacttctttatatg

ctactattcttttggcttcgttcacggggtgggtaccgagctcgaattctgtggaatgtgtgtcagttagggtgtggaaa

gtccccaggctccccaggca

ggcagaagtatgcaaagcatgcatctcaattagtcagcaaccaggtgtggaaagtccccaggctccccagcaggcagaag

tatgcaaagcatgcatctca

attagtcagcaaccatagtcccgcccctaactccgcccatcccgcccctaactccgcccagttccgcccattctccgccc
```

TABLE 8-continued catggctgactaattttttt tatttatgcagaggccgaggccgcctcggcctctgagctattccagaagtagtgaggaggcttttttggaggcctaggct tttgcaaaaagctcccggga gcttggatatccattttcggatctgatcaagagacaggatgaggatcgtttcgcatgattgaacaagatggattgcacgc aggttctccggccgcttggg tggagaggctattcggctatgactgggcacaacagacaatcggctgctctgatgccgccgtgttccggctgtcagcgcag gggcgcccggttctttttgt caagaccgacctgtccggtgccctgaatgaactgcaggacgaggcagcgcggctatcgtggctggccacgacgggcgttc cttgcgcagctgtgctcgac gttgtcactgaagcgggaagggactggctgctattgggcgaagtgccggggcaggatctcctgtcatctcaccttgctcc tgccgagaaagtatccatca tggctgatgcaatgcggcggctgcatacgcttgatccggctacctgcccattcgaccaccaagcgaaacatcgcatcgag cgagcacgtactcggatgga agccggtcttgtcgatcaggatgatctggacgaagagcatcaggggctcgcgccagccgaactgttcgccaggctcaagg cgcgcatgcccgacggcgag gatctcgtcgtgacccatggcgatgcctgcttgccgaatatcatggtggaaaatggccgcttttctggattcatcgactg tggccggctgggtgtggcgg accgctatcaggacatagcgttggctacccgtgatattgctgaagagcttggcggcgaatgggctgaccgcttcctcgtg ctttacggtatcgccgctcc cgattcgcagcgcatcgccttctatcgccttcttgacgagttcttctgagcgggactctggggttcgaaatgaccgacca agcgacgcccaacctgccat cacgagatttcgattccaccgccgccttctatgaaaggttgggcttcggaatcgttttccgggacgccggctggatgatc ctccagcgcggggatctcat gctggagttcttcgcccaccccaacttgtttattgcagcttataatggttacaaataaagcaatagcatcacaaatttca caaataaagcatttttttca ctgcattctagttgtggtttgtccaaactcatcaatgtatcttatcatgtctggatcccgtcgacctcgagagcttggcg taatcatggtcatagctgtt tcctgtgtgaaattgttatccgctcacaattccacacaacatacgagccggaagcataaagtgtaaagcctggggtgcct aatgagtgagctaactcaca ttaattgcgttgcgctcactgcccgctttccagtcgggaaacctgtcgtgccagctgcattaatgaatcggccaacgcgc ggggagaggcggtttgcgta ttgggcgctcttccgcttcctcgctcactgactcgctgcgctcggtcgttcggctgcggcgagcggtatcagctcactca aaggcggtaatacggttatc cacagaatcaggggataacgcaggaaagaacatgtgagcgggggccggcaaaaggccaggaaccgtaaaaaggccgcgt tgctggcgtttttccatagg gacggatcgggagatctcccgatcccctatggtcgactctcagtacaatctgctctgatgccgcatagttaagccagtat ctgctccctgcttgtgtgtt ggaggtcgctgagtagtgcgcgagcaaaatttaagctacaacaaggcaaggcttgaccgacaattgcatgaagaatctgc TABLE 8-continued ttagggttaggcgttttgcg ctgcttcgcgatgtacgggccagatatacgcgttgacattgattattgactagttattaatagtaatcaattacggggtc attagttcatagcccatata tggagttccgcgttacataacttacggtaaatggcccgcctggctgaccgcccaacgacccccgcccattgacgtcaata atgacgtatgttcccatagt aacgccaatagggactttccattgacgtcaatgggtggactatttacggtaaactgcccacttggcagtacatcaagtgt atcatatgccaagtacgccc cctattgacgtcaatgacggtaaatggcccgcctggcattatgcccagtacatgaccttatgggactttcctacttggca gtacatctacgtattagtca tcgctattaccatggtgatgcggttttggcagtacatcaatgggcgtggatagcggtttgactcacggggatttccaagt ctccaccccattgacgtcaa tgggagtttgttttggcaccaaaatcaacgggactttccaaaatgtcgtaacaactccgccccattgacgcaaatgggcg gtaggcgtgtacggtgggag gtctatataagcagagctctctggctaactagagaacccactgcttaactggcttatcgaaattaatacgactcactata gggagaccgg

AAGCTTCCTCGAGCGATATCGCCGCGGCATCGATCGGGCCCGAGATCTCGCGCGCCTGGGTAACATGCTTGGGGTCCTGG

TCCTTGGCGCGCTGG

CCCTGGCCGGCCTGGGGTTCCCCGCACCCGCAGAGCCGC

AGCCGG

GTGGCAGCCAGTGCGTCGAGCACGACTGCTTCGCGCTCTACCCGGGCCCCGCGAC

CTTCCTCAATGCCAGTCAGATCTGCGACGGACTGCGGGGCCACCTAATGA

CAGTGCGCTCCTCGGTGGCTGCCGATGTCATTTCCTTGCTACTGA

ACGGCGACGGCGGCGTTGGCCGCCGGCGCCTCTGGATCGGCCTGCAGCTGCCACCCGGCTGCGGCGACCCCAAGCGCCTC

GGGCCCCTGCGCGGCTTCCAGTGGGTTACGGGAGACAACAACACCAGCTATAGCAGGTGGGCACGGCTCGACCTCAATGG

GGCTCCCCTCTGCGGCCCGTTGTGCGTCGCTGTCTCCGCTGCTGAGGCCACTGTGCCCAGCGAGCCGATCTGGGAGGAGC

AGCAGTGCGAAGTGAAGGCCGATGGCTTCCTCTGCGAGTTCCACTTCCCAGCCACCTGCAGGCCACTGGCTGTGGAGCCC

GGCGCCGCGGCTGCCGCCGTCTCGATCACCTACGGCACCCCGTTCGCGGCCCGCGGAGCGGACTTCCAGGCGCTGCCGGT

GGGCAG

CTCCGCCGCGGTGGCTCCCCTCGGCTTACAGCTAATGTGCACCGCGCCGCCCGGAGCGGTCCAGGGGCACTGGGCCAGGG

AGGCGCCGGGCGCTTGGGACTGCAGCGTGGAGAACGGCGG

CTGCGA

GCACGCGTG

CAATGCGATCCCTGGGGCTCCC

CGCTGC

GAGTGCCCAGCCGGCGCCGCCCTGCAGGCAGACGGGCGCTCCTGCACCGCATCCGCGACGCAGTCCTGCAACGACCTCTG

CGAGCACTTCTGCGTTCCCAACCCGACCAGCCGGGCTCCTACTCGTGCATGTGCGAGACCGGCTACCGGCTGGCG

GCCGACCAACACCGGTGCGAGGACGTGGATGACTGCATACTGGAGCCCAGTCCGTGTCCGCAGCGCTGTGTCAACACACA

GGGTGGCTTCGAGTGCCACT

TABLE 8-continued

GCTACCCTAACTACGACCTGGTGGACGGCGAGTGTGTGGAGCCCGTGGACCCGTGCTTCAGAGCCAACTGCGAGTACCAG

TG

CCAGCCCCTGAACCAAACTAGCTACCTCTGCGTCTGCGCCGAGGGCTTCGCGCCCATTCCCCACGAGCCGCACAGGTGCC

AGATGTTTTGCAACCAGACT

GCCTGTCCAGCCGACTGCGACCCCAACACCCAGGCTAGCTGTGAGTGCCCTGAAGGCTACATCCTGGACGACGGTTTCAT

CTGCACGGACATCGACGAGT

GCGAAAACGGCGGCTTCTGCTCCGGGGTGTGCCACAACCTCCCCGGTACCTTCGAGTGCATCTGCGGGCCCGACTCGGCC

CTTGCGCGCCACATTGGCAC

CGACTGTGACTCCGGCAAGGTGGACGGTGGC

GACAGC

GGCTCTGGCGAGCCCCGCCCAGCCCGACGC

CCGGCT

CCACCTTGACTCCTCCGGCCGTGGGGCTCGTGCATTGGTGA ctccgcccccctgacgagcatcacaaaaatcgacgctcaagtcagaggtggcgaaacccgacaggactataaagatacca ggcgtttccccctggaagct ccctcgtgcgctctcctgttccgaccctgccgcttaccggatacctgtccgcctttctcccttcgggaagcgtggcgctt tctcaatgctcacgctgtag gtatctcagttcggtgtaggtcgttcgctccaagctgggctgtgtgcacgaaccccccgttcagcccgaccgctgcgcct tatccgtaactatcgtctt gagtccaacccggtaagacacgacctatcgccactggcagcagccactggtaacaggattagcagagcgaggtatgtagg cggtgctacagagttcttga agtggtggcctaactacggctacactagaaggacagtatttggtatctgcgctctgctgaagccagttaccttcggaaaa agattggtagctcttgatc cggcaaacaaaccaccgctggtagcggtggtttttttgtttgcaagcagcagattacgcgcagaaaaaaaggatctcaag aagatcctttgatcttttct acggggctcacgctcagtggaacgaaaactcacgttaagggattttggtcatgagattatcaaaaaggatcttcaccta gatccttttaaattaaaaat gaagttttaaatcaatctaaagtatatatgagtaaacttggtctgacagttaccaatgcttaatcagtgaggcacctatc tcagcgatctgtctatttcg ttcatccatagttgcctgactccccgtcgtgtagataactacgatacgggagggcttaccatctggccccagtgctgcaa tgataccgcgagacccacgc tcaccggctccagatttatcagcaataaaccagccagccggaagggccgagcgcagaagtggtcctgcaactttatccgc ctccatccagtctattaatt gttgccgggaagctagagtaagtagttcgccagttaatagtttgcgcaacgttgttgccattgctacaggcatcgtggtg tcacgctcgtcgtttggtat ggcttcattcagctccggttcccaacgatcaaggcgagttacatgatcccccatgttgtgcaaaaaagcggttagctcct tcggtcctccgatcgttgtc agaagtaagttggccgcagtgttatcactcatggttatggcagcactgcataattctcttactgtcatgccatccgtaag atgcttttctgtgactggtg TABLE 8-continued

| |
|---|
| agtactcaaccaagtcattctgagaatagtgtatgcggcgaccgagttgctcttgcccggcgtcaatacgggataatacc |
| gcgccacatagcagaacttt |
| aaaagtgctcatcattggaaaacgttcttcggggcgaaaactctcaaggatcttaccgctgttgagatccagttcgatgt |
| aacccactcgtgcacccaac |
| tgatcttcagcatcttttactttcaccagcgtttctgggtgagcaaaaacaggaaggcaaaatgccgcaaaaaagggaat |
| aagggcgacacggaaatgtt |
| gaatactcatactcttcctttttcaatattattgaagcatttatcagggttattgtctcatgagcggatacatatttgaa |
| tgtatttagaaaaataaaca |
| aataggggttccgcgcacatttccccgaaaagtgccacctgacgtc |

*HIND3-NOT1 fragment from pTHR322 containing the DNFL TM gene into the HIND3-NOT 1 sites of pRcCMV for expression of DNFL in COS1 cells.

A. Modification of the protease cleavage site

The $Arg^{456}/His^{457} \rightarrow Gly^{456}/Gln^{457}$ mutation was constructed as disclosed in Example 1(C) using as a primer oligomer COD-2218.

B. Modification of the O-linked chondroitin sulfate linkage site

The $Ser^{474} \rightarrow Ala^{474}$ mutation was constructed as disclosed in Example 1(C) using as a primer oligomer COD1886.

C. Modification of the N-terminus

The N-terminal deletion of the first three amino acids of native TM, which has a heterogeneous signal sequence cleavage site, was constructed as disclosed in Example 1(C) using as a primer oligomer COD-2321. The construct has a change in the fourth glycine of the signal sequence (i.e., amino acid −3) from Gly to Val, in addition to providing an N-terminal sequence, after processing of the signal sequence, which begins at amino acid Gly4. This construct was prepared based upon predictions of signal cleavage efficiencies using algorithms described in von Heijne, G., Nucleic Acids Res. 14 4683 (1986).

D. Modification of the C-terminus

The C-terminal deletion of the terminal 7 amino acids of the $TM_{LEO}$ polypeptide to produce a polypeptide ending at amino acid 490 of TM (with reference to the native human protein) to produce an exoprotease-resistant Pro-Pro sequence C-terminus was constructed as disclosed in Example 1(C) using as a primer oligomer COD-2320. A summary of the modifications to the C-terminus is shown in Table 9.

E. Summary of the Construction of pTHR525

The starting plasmid, pCDM8, for the following constructs was obtained from Invitrogen, San Diego, Calif. It carries the cytomegalovirus immediate early promoter. pTHR219 was cut with and the MluI-NotI fragment isolated. This fragment was inserted into pTHR211 yielding pTHR253. pTHR253 was mutagenized with COD2218 to convert R456G and H457Q, yielding pTHR491. pTHR491 was cut and the Kpn-NotI fragment isolated. This fragment was inserted into the Kpn-NotI site of pTHR470, carrying the S474A mutation yielding pTHR496. This plasmid contains the mutations S474A, R456G, and H457Q. pTHR496 was cut and the MluI-NotI fragment isolated. This fragment was inserted into the MluI-NotI site of pTHR235 yielding pTHR511. This plasmid contains the mutations S474A, R456G, H457Q, and the upstream TM sequences from the NotI site. pTHR511 was mutagenized with COD2320 to remove the 7 C-terminal amino acids yielding pTHR514. pTHR514 was cut and the MluI-NotI fragment isolated. This fragment was inserted into pTHR518 yielding pTHR524. pTHR518 was constructed by inserting the ClaI-SmaI fragment from pTHR515 into pTHR512. pTHR524 was cut and the XbaI-NotI fragment isolated. This fragment was inserted into pTHR495 at the XbaI-NotI site yielding pTHR525. pTHR525 is expressed to make one of the preferred thrombomodulin analogs having N-terminal 63, R456G, H457Q, S474A, and C-terminal δ7.

TABLE 9

| C-Terminal Modification |
|---|
| ECICGPDSALARHIGTDCDSGKVDGGDSGSGEPPPSPTPGSTLTPPAVGLVH |
| ↓ |
| * * * |
| ECICGPDSALAGQIGTDCDSGKVDGGDSGAGEPPPSPTPGSTLTPP |

Appendix A shows sequences from the various intermediate plasmid constructs.

Appendix B shows the sequences of the various primers used to mutagenize the plasmids.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

APPENDIX A pTHR496

GAACTTTAAAAGTGCTCATCATTGGAAAACGTTCTTCGGGGCGAAAACTCTCAAGGATC

TTACCGCTGTTGAGATCCAGTTCGATGTAACCCACTCGTGCACCCAACTGATCTTCAGC

ATCTTTTACTTTCACCAGCGTTTCTGGGTGAGCAAAAACAGGAAGGCAAAATGCCGCAA

AAAAGGGAATAAGGGCGACACGGAAATGTTGAATACTCATACTCTTCCTTTTTCAATAT

TATTGAAGCATTTATCAGGGTTATTGTCTCATGAGCGGATACATATTTGAATGTATTTA

GAAAAATAAACAAATAGGGGTTCCGCGCACATTTCCCCGAAAAGTGCCACCTGACGTCT

AAGAAACCATTATTATCATGACATTAACCTATAAAAATAGGCGTATCACGAGGCCCTTT

CGTCTTCGAATTCAGGCCATGTTTGACAGCTTATC

ATCGAT

*KPN1-NOT1 fragment from pTHR491 containing the Olink domain into the KPN1-NOT1 sites of pTHR470 to make a mammalian expression plasmid that expresses DNFL with the R456G, H457Q, and S474A mutations.

pTHR491

AGCGAAGCGAGCAGGACTGGGCGGCGGCCAAAGCGGTCGGACAGTGCTCCGAGAACGGGTGCGCATAGAAAT

TGCATCAACGCATATAGCGCTAGCAGCACGCCATAGTGACTGGCGATGCTGTCGGAATGGAC

GATATC

CCGC

AAGAGGCCCGGCAGTACCGGCATAACCAAGCCTATGCCTACAGCATCCAGGGTGACGGTGCCGAGGATGACG

ATGAGCGCATTGTTAGATTTCATACACGGTGCCTGACTGCGTTAGCAATTTAACTGTGATAAACTACCGCAT

TAAAGCTTATCGATGATAAGCTGTCAAACATGAGAATTC

TTG

AAGACGAAAGGGCCTCGTGATACGCCTATTTTTATAGGTTAATGTCATGATAATAATGGTTTCTTAGACGTC

*COD2218 was used to convert Arg 456 Gly and His 457 Gln by in vitro mutagenesis in the vector pTHR235. This created a MSC1 site. This creates an O-link domain that should not be cleaved in CHO cells. Also, COD1886 was used to convert Ser 474 to Ala, to eliminate a potential GAG site in the O-link domain. This created a NAR1 site. Also, COD1689 was used to convert AMP sensitive to AMP resitant.

pTHR235

AGCGAAGCGAGCAGGACTGGGCGGCGGCCAAAGCGGTCGGACAGTGCTCCGAGAACGGGTGCGCATAGAAAT

TGCATCAACGCATATAGCGCTAGCAGCACGCCATAGTGACTGGCGATGCTGTCGGAATGGAC

GATATC

CCGC

AAGAGGCCCGGCAGTACCGGCATAACCAAGCCTATGCCTACAGCATCCAGGGTGACGGTGCCGAGGATGACG

ATGAGCGCATTGTTAGATTTCATACACGGTGCCTGACTGCGTTAGCAATTTAACTGTGATAAACTACCGCAT

TAAAGCTTATCGATGATAAGCTGTCAAACATGAGAATTC

TTG

AAGACGAAAGGGCCTCGTGATACGCCTATTTTTATAGGTTAATGTCATGATAATAATGGTTTCTTAGACGTC

APPENDIX A-continued

*MLU1-NOT1 fragment from pTHR219 containing the 6EGFs-Olinked into the MLU1-NOT1 sites of pTHR211 containging the Fiori in the opposite orientation as pTHR219. This new plasmid is for in vitro mutagenesis of the Olinked and 6EGFs regions.

pTHR498

GAACTTTAAAAGTGCTCATCATTGGAAAACGTTCTTCGGGGCGAAAACTCTCAAGGATC

TTACCGCTGTTGAGATCCAGTTCGATGTAACCCACTCGTGCACCCAACTGATCTTCAGC

ATCTTTTACTTTCACCAGCGTTTCTGGGTGAGCAAAAACAGGAAGGCAAAATGCCGCAA

AAAAGGGAATAAGGGCGACACGGAAATGTTGAATACTCATACTCTTCCTTTTTCAATAT

TATTGAAGCATTTATCAGGGTTATTGTCTCATGAGCGGATACATATTTGAATGTATTTA

GAAAAATAAACAAATAGGGGTTCCGCGCACATTTCCCCGAAAAGTGCCACCTGACGTCT

AAGAAACCATTATTATCATGACATTAACCTATAAAAATAGGCGTATCACGAGGCCCTTT

CGTCTTCGAATTCAGGCCATGTTTGACAGCTTATC

ATCGAT

*XBA1-SAL1 fragment from pTHR463 containing the DNFL gene into the XBA1-SAL1 sites of pBBS37 to make a mammalian expression plasmid that expresses DNFL using the MPSV promoter + CMV enhancer and has the DHFR gene expressed off the SV40 late promoter. This plasmid also contains the HygromycinB gene.

pTHR518

AGCGCGCGAACAGAAGCGAGAAGCGAACTGATTGGTTAGTTCAAATAAGGCACAGGGTCATTTCAGGTCCTTGGGGCACC

CTGG

AAACATCTGATGGTTC

TCTAGA

CTGGAATTCGTCGACGAGCTCCCTATAGTGAGTCGTATTAGAG

GCCGACTTGGCCAAATTCGTAATCATGGTCATAGCTGTTTCCTGTGTGAA

ATTGTTATCCGCTCACAATTCCACACAACATACGAGCCGGAAGCATAAAG

TGTAAAGCCTGGGGTGCCTAATGAGTGAGCTAACTCACATTAATTGCGTT

GCGCTCACTGCCCGCTTTCCAGTCGGGAAACCTGTCGTGCCAGCTGCATT

AATGAATCGGCCAACGCGCGGGGAG

*CLA1-SMA1 fragment from pTHR515 containing the 3aa deletion of the Nterminus of DNFL into the CLA1-SMA1 partial of pTHR512.

pTHR515

CCCGGG

TAGAGCGCGAAGCAGTCGTGCTCGACGCACTGG

CTGCCACCCGGCTGCGGCTCGG GGAAGACCAGGCCTGCCAGGGCCAGC

GCGCCAAGGACCAGGACCCCAAGCATGTTACCCAGGCGCGCgagatctcgggcccg atcgat gccgcggcgatatcgctcgagg

AAGCTT

GAGTATTCTATAGTGTCACCTAAATAGCTTGGCGTAATCATGGTCATA

GCTGTTTCCTGTGTGAAATTGTTATCCGCTCACAATTCCACACAACATACGAGCCGGAAGCATAAAGTGTAAAGCCTGGG

GTGCCTAATGAGTGAGCTAACCACATTAATTTGCGTTGCGCTCACTGCCCGCTTTCCAGTCGGGAAACCTGTCGTGCCAG

CTGCATTAATGAATCGGCCAACGCGCGGGGAGAGGCGGTTTGCGTATTGGGCGCTCTTCCGCTTCCTCGCTCACTGACTC

GCTGCGCTCGGTCGTTCGGCTGCGGCGAGCGGTATCAGCTCACTCAAAGGCGGTAATACG

APPENDIX A-continued

*COD2321 was used to delete the first 3 codons of the lectin domain and convert the fourth glycine of the signal to valine by in vitro mutagenesis in pTHR356. This created a STU1 site. Also, COD1690 was used to convert AMP sensitive to AMP resistant. This created a PST1 site.

pTHR356

TAGAGCGCGAAGCAGTCGTGCTCGACGCACTGGCTGCCACCCGGCTGCGGCTCTGCG

GGTGCGGGGAACCCCAGGCCGGCCAGGGCCA

GCGCGC

CAAGGACCAGGACCCCAAGCATGTTACCCAG

GCGCGC gagatctcgggcccgatcgatgccgcggcgatatcgctcgagg

AAGCTT

GAGTATTCTATAGTGTCACCTAAATAGCTTGGCGTAATCATGGTCATA

GCTGTTTCCTGTGTGAAATTGTTATCCGCTCACAATTCCACACAACATACGAGCCGGAAGCATAAAGTGTAAAGCCTGGG

GTGCCTAATGAGTGAGCTAACCACATTAATTTGCGTTGCGCTCACTGCCCGCTTTCCAGTCGGGAAACCTGTCGTGCCAG

CTGCATTAATGAATCGGCCAACGCGCGGGGAGAGGCGGTTTGCGTATTGGGCGCTCTTCCGCTTCCTCGCTCACTGACTC

GCTGCGCTCGGTCGTTCGGCTGCGGCGAGCGGTATCAGCTCACTCAAAGGCGGTAATACG

*HIND3-SMA1 fragment of pTHR322 containing the signal sequence of Thrombomodulin into the HIND3-SMA1 sites of pSELECT1. This plasmid will be used for mutagenesis of the TM signal cleavage site.

pTHR219

AGCGAAGCGAGCAGGACTGGGCGGCGGCCAAAGCGGTCGGACAGTGCTCCGAGAACGGGTGCGCATAGAAAT

TGCATCAACGCATATAGCGCTAGCAGCACGCCATAGTGACTGGCGATGCTGTCGGAATGGAC

GATATC

CCGC

AAGAGGCCCGGCAGTACCGGCATAACCAAGCCTATGCCTACAGCATCCAGGGTGACGGTGCCGAGGATGACG

ATGAGCGCATTGTTAGATTTCATACACGGTGCCTGACTGCGTTAGCAATTTAACTGTGATAAACTACCGCAT

TAAAGCTTATCGATGATAAGCTGTCAAACATGAGAATTC

TTG

AAGACGAAAGGGCCTCGTGATACGCCTATTTTTATAGGTTAATGTCATGATAATAATGGTTTCTTAGACGTC

*MLU1-NOT1 fragment from pTHR127 containing the Met388 --> Leu mutation in the 6EGFs
into the MLU1-NOT1 sites of pTHR161 in order to make an E. coli expression vector that can be used for in vitro mutagenesis.

pTHR512

AGCGCGCGAACAGAAGCGAGAAGCGAACTGATTGGTTAGTTCAAATAAGGCACAGGGTCATTTCAGGTCCTTGGGGCACC

CTGG

AAACATCTGATGGTTC

TCTAGA

CTGGAATTCGTCGACGAGCTCCCTATAGTGAGTCGTATTAGAG

GCCGACTTGGCCAAATTCGTAATCATGGTCATAGCTGTTTCCTGTGTGAA

ATTGTTATCCGCTCACAATTCCACACAACATACGAGCCGGAAGCATAAAG

TGTAAAGCCTGGGGTGCCTAATGAGTGAGCTAACTCACATTAATTGCGTT

GCGCTCACTGCCCGCTTTCCAGTCGGGAAACCTGTCGTGCCAGCTGCATT

AATGAATCGGCCAACGCGCGGGGAG

APPENDIX A-continued

*NOT1-XBA1 fragment from pTHR498 containing the DNFL gene into the NOT1-XBA1 sites of pGEM9Zf-. This plasmid is designated 'A' in the strategy for construction of a Patent TM production plasmid.

pTHR211

AGCGAAGCGAGCAGGACTGGGCGGCGGCCAAAGCGGTCGGACAGTGCTCCGAGAACGGGTGCGCATAGAAAT

TGCATCAACGCATATAGCGCTAGCAGCACGCCATAGTGACTGGCGATGCTGTCGGAATGGAC

GATATC

CCGC

AAGAGGCCCGGCAGTACCGGCATAACCAAGCCTATGCCTACAGCATCCAGGGTGACGGTGCCGAGGATGACG

ATGAGCGCATTGTTAGATTTCATACACGGTGCCTGACTGCGTTAGCAATTTAACTGTGATAAACTACCGCAT

TAAAGCTTATCGATGATAAGCTGTCAAACATGAGAATTC

TTG

AAGACGAAAGGGCCTCGTGATACGCCTATTTTTATAGGTTAATGTCATGATAATAATGGTTTCTTAGACGTC

*SCA1-SAC1 fragment from pGEM3zf- containing the f1 origin of replication into the SCA1-SAC1 sites of pTHR161. This is a new mutagenesis vector that uses the opposite strand as pTHR161.

pTHR515

CCCGGG

TAGAGCGCGAAGCAGTCGTGCTCGACGCACTGG

CTGCCACCCGGCTGCGGCTCGG GGAAGACCAGGCCTGCCAGGGCCAGC

GCGCCAAGGACCAGGACCCCAAGCATGTTACCCAGGCGCGCgagatctcgggcccg atcgat gccgcggcgatatcgctcgagg

AAGCTT

GAGTATTCTATAGTGTCACCTAAATAGCTTGGCGTAATCATGGTCATA

GCTGTTTCCTGTGTGAAATTGTTATCCGCTCACAATTCCACACAACATACGAGCCGGAAGCATAAAGTGTAAAGCCTGGG

GTGCCTAATGAGTGAGCTAACCACATTAATTTGCGTTGCGCTCACTGCCCGCTTTCCAGTCGGGAAACCTGTCGTGCCAG

ATGATTTGATAAATCCCTTTCCCTCTAGAGAGGCGGTTTGCCTATTGGCTTTTGTTCCGGTTCCTCGCTCAGTGACTAAC

GCTGCGCTCGGTCGTTCGGCTGCGGCGAGCGGTATCAGCTCACTCAAAGGCGGTAATACG

*COD2321 was used to delete the first 3 codons of the lectin domain and convert the fourth glycine of the signal to valine by in vitro mutagenesis in pTHR356. This created a STU1 site. Also, COD1690 was used to convert AMP sensitive to AMP resistant. This created a PST1 site.

pTHR470

GAACTTTAAAAGTGCTCATCATTGGAAAACGTTCTTCGGGGCGAAAACTCTCAAGGATC

TTACCGCTGTTGAGATCCAGTTCGATGTAACCCACTCGTGCACCCAACTGATCTTCAGC

ATCTTTTACTTTCACCAGCGTTTCTGGGTGAGCAAAAACAGGAAGGCAAAATGCCGCAA

AAAAGGGAATAAGGGCGACACGGAAATGTTGAATACTCATACTCTTCCTTTTTCAATAT

TATTGAAGCATTTATCAGGGTTATTGTCTCATGAGCGGATACATATTTGAATGTATTTA

GAAAAATAAACAAATAGGGGTTCCGCGCACATTTCCCCGAAAAGTGCCACCTGACGTCT

AAGAAACCATTATTATCATGACATTAACCTATAAAAATAGGCGTATCACGAGGCCCTTT

CGTCTTCGAATTCAGGCCATGTTTGACAGCTTATC

ATCGAT

*HIND3 fragment from pTHR359 containing the SV40 promoter into the HIND3 sites of pTHR359 to make an expression plasmid that expresses the DNFL gene off the SV4 to early promoter and the DHFR gene off the SV40 late promoter. Note: The SV40 Late APPENDIX A-continued promoter initiates transcription from several locations. The main transcription initation site is not included in this plasmid. Also Note: there are 3 ATGs between the late promoter and the ATG of DHFR which may hinder expression of DHFR. So expression may be too weak to express the DHFR gene.

pTHR525

GAACTTTAAAAGTGCTCATCATTGGAAAACGTTCTTCGGGGCGAAAACTCTCAAGGATC

TTACCGCTGTTGAGATCCAGTTCGATGTAACCCACTCGTGCACCCAACTGATCTTCAGC

ATCTTTTACTTTCACCAGCGTTTCTGGGTGAGCAAAAACAGGAAGGCAAAATGCCGCAA

AAAAGGGAATAAGGGCGACACGGAAATGTTGAATACTCATACTCTTCCTTTTTCAATAT

TATTGAAGCATTTATCAGGGTTATTGTCTCATGAGCGGATACATATTTGAATGTATTTA

GAAAAATAAACAAATAGGGGTTCCGCGCACATTTCCCCGAAAAGTGCCACCTGACGTCT

AAGAAACCATTATTATCATGACATTAACCTATAAAAATAGGCGTATCACGAGGCCCTTT

CGTCTTCGAATTCAGGCCATGTTTGACAGCTTATC

ATCGAT

XBA1-NOT1 fragment from pTHR524 containing the 3aa deletion of the N-terminus plus the 4th aa Gly-Val, the 7aa deletion of the C-terminus, the 9474A mutation, and the R456G, H457Q mutation of DNFL, into the XBA1-NOT1 sites of pTHR498.

pTHR524

AGCGCGCGAACAGAAGCGAGAAGCGAACTGATTGGTTAGTTCAAATAAGGCACAGGGTCATTTCAGGTCCTTGGGGCACC

CTGG

AAACATCTGATGGTTC

TCTAGA

CTGGAATTCGTCGACGAGCTCCCTATAGTGAGTCGTATTAGAG

GCCGACTTGGCCAAATTCGTAATCATGGTCATAGCTGTTTCCTGTGTGAA

ATTGTTATCCGCTCACAATTCCACACAACATACGAGCCGGAAGCATAAAG

TGTAAAGCCTGGGGTGCCTAATGAGTGAGCTAACTCACATTAATTGCGTT

GCGCTCACTGCCCGCTTTCCAGTCGGGAAACCTGTCGTGCCAGCTGCATT

AATGAATCGGCCAACGCGCGGGGAG

*MLU-NOT1 fragment from pTHR514 containing a 7aa deletion at the end of the olink region of DNFL, the S474A, the R456G and the H457Q mutations into the MLU1-NOT1 sites of pTHR518.

THR514

AGCGAAGCGAGCAGGACTGGGCGGCGGCCAAAGCGGTCGGACAGTGCTCCGAGAACGGGTGCGCATAGAAAT

TGCATCAACGCATATAGCGCTAGCAGCACGCCATAGTGACTGGCGATGCTGTCGGAATGGAC

GATATC

CCGC

AAGAGGCCCGGCAGTACCGGCATAACCAAGCCTATGCCTACAGCATCCAGGGTGACGGTGCCGAGGATGACG

ATGAGCGCATTGTTAGATTTCATACACGGTGCCTGACTGCGTTAGCAATTTAACTGTGATAAACTACCGCAT

TAAAGCTTATCGATGATAAGCTGTCAAACATGAGAATTC

TTG

AAGACGAAAGGGCCTCGTGATACGCCTATTTTTATAGGTTAATGTCATGATAATAATGGTTTCTTAGACGTC

*COD2320 was used to delete 7 amino acids from the C-teriminus of the O-link domain of TM by in vitro mutagenesis of pTHR511. This created an ACC1 site. Also, COD1689 was used to convert AMP sensitive to AMP resistant. This created a PST1 site.

APPENDIX A-continued pTHR511

AGCGAAGCGAGCAGGACTGGGCGGCGGCCAAAGCGGTCGGACAGTGCTCCCAGAACGGGTGCGCATAGAAAT

TGCATCAACGCATATAGCGCTAGCAGCACGCCATAGTGACTGGCGATGCTGTCGGAATGGAC

GATATC

CCGC

AAGAGGCCCGGCAGTACCGGCATAACCAAGCCTATGCCTACAGCATCCAGGGTGACGGTGCCGAGGATGACG

ATGAGCGCATTGTTAGATTTCATACACGGTGCCTGACTGCGTTAGCAATTTAACTGTGATAAACTACCGCAT

TAAAGCTTATCGATGATAAGCTGTCAAACATGAGAATTC

TTG

AAGACGAAAGGGCCTCGTGATACGCCTATTTTTATAGGTTAATGTCATGATAATAATGGTTTCTTAGACGTC

*MLU1-NOT1 fragment from pTHR491 containing the S474A, R456G and H457Q mutation
of the DNFL gene into the MLU1-NOT1 sites of pTHR235.

pTHR525.SEQ
AAAACGGCGG CTTCTGCTCC GGGGTGTGCC ACAACCTCCC CGGTACCTTC

GAGTGCATCT GCGGGCCCGA CTCGGCCCTT GCTGGCCAGA TTGGCACCGA

CTGTGACTCC GGCAAGGTGG ACGGTGGCGA CAGCGGCGCC GGCGAGCCCC

CGCCCAGCCC GACGCCCGGG TCTACCTTGA CTCCTCCGTG AGCGGCCGCT

GCAGATCGAT GCCGCGGCGA TATCGCTCGA GGAAGCTTCG ATCCAGACAT

GATAAGATAC ATTGATGAGT TTGGACAAAC CACAACTAGA ATGCAGTGAA

AAAAATGCTT TATTTGTGAA ATTTGTGATG CTATTGCTTT ATTTGTAACC

ATTATAAGCT GCAATAAACA AGTTAA pTHR525.seqA
TTTCCAGGGTGCCCCAAGGACCTGAAATGACCCTGTGCCTTATTTGAACTAACCAATCAGTTCGCTTCTCGC

TTCTGTTCGCGCGCTTCTGCTCCCCGAGCTCAATAAAAGAGCCCACAACCCCTCACTCGGCGCGCCAGTCCTC

CGATAGACTGCGTCGCCCGGGTACCGAGCTCGAATTGATCTCGAGGAACTGAAAAACCAGAAAGTTAACTGGT

AAGTTTAGTCTTTTTGTCTTTTATTTCAGGTCCCGGATCGGAATTCCCATCGCCGCGGCATCGATCGGGCCCG

AGATCTCGCGCGCCTGGGTAACATGCTTGGGGTCCTGGTCCTTGGCGCGCTGGCCCTGGCAGGCCTGGTCTTC

CCCGAGCCGCAGCCGGGTGGCAGCCAGTGCGTCGAGCACGACTGCTTCGCGCTCTACCCGGGCCCCGCGACCT

TCCTCAATGCCAGTCAGATCTGCGACGGACTGCGGGGCCACCTAATGACAGTGCGCTCCTCGGTGGCTGCCGA

TGTCATTTCCTTGCTACTGAACGGCGACGGCGGCGTTNNNNNNNNNNNNNNCTGGATCGGCCTGCAGCTGCCA

CCCGGCTGCGGCGACCCCAAGCGCCTCGGGCCCC

APPENDIX B

```
OLIGOMER SYNTHESIS REQUEST FORM           COD-2321
-------------------------------           --------
Oligomer size: 48                         Project: TM
Purpose: convert fourth Gly of TM signal sequence to Val and delete Ala of Ala of
signal.
               5'------------------------------------> 3'
   3   6   9  12  15  18  21  24  27  30  33  36  39  42  45  48
 CTG CCA CCC GGC TGC GGC TCG GGG AAG ACC AGG CCT GCC AGG GCC AGC
----------------------------------------------------------------------
Notes: Detect with STU1

Code  Meaning
----  -------
A     Adenine
C     Cytosine
```

APPENDIX B-continued

```
G     Guanine
T     Thymine

OLIGOMER SYNTHESIS REQUEST FORM              COD-2320
-------------------------------              --------
Oligomer size: 51                            Project: TM
Purpose: delete 7 amino acids from the 3' end of O-link region, by mutagenesis
                5'----------------------------------------> 3'
  3   6   9  12  15  18  21  24  27  30  33  36  39  42  45  48  51
CCC GAC GCC CGG GTC TAC CTT GAC TCC TCC GTG AGC GGC CGC CAG ATC CCC
------------------------------------------------------------------------
Notes: Detect with ACC1

Code  Meaning
----  -------
A     Adenine
C     Cytosine
G     Guanine
T     Thymine

OLIGOMER SYNTHESIS REQUEST FORM              COD-2218
-------------------------------              --------
Oligomer size: 35                            Project: tm
Purpose: mutagenic oligo to convert R456, H457 to G456, Q457 in DNFL. Screen with
BAL1.
                5'---------------------------------------- 3'
  3   6   9  12  15  18  21  24  27  30  33 35
SAC TCG GCC CTT GCT GGC CAG ATT GGC ACC GAC TG

Code  Meaning
----  -------
A     Adenine
C     Cytosine
G     Guanine
T     Thymine

OLIGOMER SYNTHESIS REQUEST FORM              COD-1886
-------------------------------              --------
Oligomer size: 27
Project: tm
Purpose: to destroy third potential gag site in olink domain by mutagenesis. This
creates an NAR1 site.
                5'---------------------------------------- 3'
  3   6   9  12  15  18  21  24  27
GGC GAC AGC GGC GCC GGC GAG CCC CCG
```

What is claimed is:

1. A thrombomodulin protein analog, wherein the amino acid sequence of a protease cleavage site is modified by substitution or deletion of an amino acid at the protease cleavage site, whereby the analog is resistant to protease cleavage at that site and wherein the analog has at least 50% of the ability to potentiate thrombin-mediated activation of protein C as said uncleaved protein without said modification at the protease cleavage site.

2. A thrombomodulin analog of claim 1, wherein the amino acid sequence of the unmodified protease cleavage site of the protein is between $Arg^{456}$ and $His^{457}$ of natural thrombomodulin.

3. A thrombomodulin analog of claim 2, wherein the amino acid sequence of the protease cleavage site has been modified to $Gly^{456}$-$Gln^{457}$.

4. A thrombomodulin protein analog, wherein the amino acid sequence of the N-terminus is modified by substitution or deletion of one or more amino acids at the N-terminus to prevent signal sequence cleavage heterogeneity, whereby the analog has a single N-terminus, and wherein the analog has at least 50% of the ability to potentiate thrombin-mediated activation of protein C as said protein having a native thrombomodulin N-terminus, wherein said analog comprises a polypeptide having an amino acid sequence corresponding to the lectin binding, EGF, and O-linked glycosylation domains of native thrombomodulin.

5. A thrombomodulin of claim 4, wherein the N-terminal amino acid is $Glu^4$ of natural thrombomodulin.

6. A pharmaceutical composition comprising an effective amount of a thrombomodulin analog of claim 4 and a pharmaceutically acceptable excipient.

7. A soluble thrombomodulin protein analog, wherein the amino acid sequence of the C-terminus is modified in the O-linked glycosylation domain by substitution or deletion of one or more amino acids to provide a C-terminus resistant to exoproteolytic cleavage, whereby the analog has a single C-terminus, and wherein the analog has at least 50% of the ability to potentiate thrombin-mediated activation of protein C as said protein having a native thrombomodulin C-terminus.

8. A pharmaceutical composition comprising an effective amount of a thrombomodulin analog of claim 7 and a pharmaceutically acceptable excipient.

9. A thrombomodulin of claim 7, wherein the C-terminal amino acids are -$Pro^{489}$-$Pro^{490}$ of natural thrombomodulin.

10. A process of preventing the loss of specific activity of a thrombomodulin protein, comprising preventing the cleavage by a protease of single-chain thrombomodulin protein by modifying the amino acid sequence of the protease site by substitution or deletion of an amino acid at the protease cleavage site, whereby the protease cleavage site cannot be cleaved by said protease and wherein the analog has at least 50% of the ability to potentiate thrombin-mediated activation of protein C as said uncleaved protein without said modification at the protease cleavage site.

11. A pharmaceutical composition comprising an effective amount of a thrombomodulin analog of claim 1 and a pharmaceutically acceptable excipient.

12. A thrombomodulin analog of claim 1, further wherein the amino acid sequence of the N-terminus is modified by substitution or deletion of one or more amino acids at the N-terminus to prevent signal sequence cleavage heterogeneity, whereby the analog has a single N-terminus, and wherein the analog has at least 50% of the ability to potentiate thrombin-mediated activation of protein C as said protein having a native thrombomodulin N-terminus, wherein said analog comprises a polypeptide having an amino acid sequence corresponding to the lectin binding, EGF, and O-linked glycosylation domains of native thrombomodulin.

13. A thrombomodulin analog of claim 1, further wherein the amino acid sequence of the C-terminus is modified by substitution or deletion of one or more amino acids to provide a C-terminus resistant to exoproteolytic cleavage, whereby the analog has a single C-terminus, and wherein the analog has at least 50% of the ability to potentiate thrombin-mediated activation of protein C as the protein having a native thrombomodulin C-terminus.

14. A thrombomodulin analog of claim 7, further wherein the amino acid sequence of the N-terminus is modified by substitution or deletion of one or more amino acids at the N-terminus to prevent signal sequence cleavage heterogeneity, whereby the analog has a single N-terminus, and wherein the analog has at least 50% of the ability to potentiate thrombin-mediated activation of protein C as said protein having a native thrombomodulin N-terminus, wherein said analog comprises a polypeptide having an amino acid sequence corresponding to the lectin binding, EGF, and O-linked glycosylation domains of native thrombomodulin.

15. A thrombomodulin analog of claim 14, further wherein the O-inked glycosylation domain is modified by substitution or deletion of an amino acid residue forming a glycosylation site, whereby addition of glycosaminoglycan to a serine or threonine residue in the O-linked glycosylation domain is attenuated, said analog having at least 50% of the ability to potentiate thrombin-mediated activation of protein C and a reduced ability to inactivate thrombin-mediated conversion of fibrinogen to fibrin, each ability as compared with native thrombomodulin.

16. A thrombomodulin analog of claim 15, further wherein an oxidation-sensitive methionine at a position corresponding to the methionine at position 388 of native thrombomodulin is modified by substitution or deletion, whereby the analog is resistant to oxidation inactivation at said methionine residue, and wherein the analog has at least 50% of the ability to potentiate thrombin-mediated activation of protein C as the unoxidized protein having a methionine residue at that position.

17. A thrombomodulin analog of claim 16, which has the amino acid sequence of native thrombomodulin modified at the following positions: removal of amino acids 1–3,

M388L,

R456G,

H457Q,

S474A, and terminating at P490.

18. A pharmaceutical composition comprising an effective amount of a thrombomodulin analog of claim 17 and a pharmaceutically acceptable excipient.

* * * * *